US006458162B1

(12) United States Patent
Koblish et al.

(10) Patent No.: US 6,458,162 B1
(45) Date of Patent: Oct. 1, 2002

(54) COMPOSITE SHAPED BODIES AND METHODS FOR THEIR PRODUCTION AND USE

(75) Inventors: Antony Koblish, Malvern, PA (US); Ronald S. Sapieszko, Woodbury, MN (US); David H. Dychala, West Chester; Eric M. Erbe, Berwyn, both of PA (US)

(73) Assignee: Vita Special Purpose Corporation, Wilmington, DE (US)

( * ) Notice: Subject to any disclaimer, the term of this patent is extended or adjusted under 35 U.S.C. 154(b) by 0 days.

(21) Appl. No.: 09/373,796

(22) Filed: Aug. 13, 1999

(51) Int. Cl.[7] ............................. A61F 2/36; B22B 5/16; C01B 15/16

(52) U.S. Cl. ..................... 623/23.51; 428/404; 423/305

(58) Field of Search ........................ 623/23.51, 23.55, 623/23.56, 23.58, 23.61, 23.62; 523/115, 116; 428/404; 427/2.26, 2.27; 423/305, 311

(56) References Cited

U.S. PATENT DOCUMENTS

| | | | |
|---|---|---|---|
| 3,090,094 A | 5/1963 | Schwartzwalder et al. | 25/156 |
| 3,679,360 A | 7/1972 | Rubin et al. | 23/109 |
| 3,833,386 A | 9/1974 | Wood et al. | 106/41 |
| 3,877,973 A | 4/1975 | Ravault | 264/44 |
| 3,907,579 A | 9/1975 | Ravault | 106/41 |
| 4,004,933 A | 1/1977 | Ravault | 106/40 R |
| 4,149,893 A * | 4/1979 | Aoki et al. | 106/35 |
| 4,328,034 A | 5/1982 | Ferguson | 106/75 |
| 4,612,053 A * | 9/1986 | Brown et al. | 706/35 |
| 4,673,355 A | 6/1987 | Farris et al. | 433/218 |
| 4,849,193 A | 7/1989 | Palmer et al. | 423/308 |
| 4,859,383 A | 8/1989 | Dillon | 264/43 |
| 4,880,610 A * | 11/1989 | Constantz | 423/305 |
| 4,897,250 A | 1/1990 | Sumita | 423/308 |
| 4,983,573 A | 1/1991 | Bolt et al. | 505/1 |
| 5,034,352 A | 7/1991 | Vit et al. | 501/1 |
| 5,047,031 A | 9/1991 | Constantz | 606/77 |
| 5,129,905 A | 7/1992 | Constantz | 606/76 |
| 5,219,829 A | 6/1993 | Bauer et al. | 505/1 |
| 5,296,261 A | 3/1994 | Bouet et al. | 427/123 |
| 5,298,205 A | 3/1994 | Hayes et al. | 264/25 |
| 5,322,675 A | 6/1994 | Hakamatsuka et al. | 423/311 |
| 5,338,334 A * | 8/1994 | Zhen et al. | 75/362 |
| 5,338,356 A | 8/1994 | Hirano et al. | 106/690 |
| 5,409,982 A | 4/1995 | Imura et al. | 524/417 |
| 5,427,754 A | 6/1995 | Nagata et al. | 423/308 |
| 5,496,399 A | 3/1996 | Ison et al. | 106/35 |
| 5,522,893 A * | 6/1996 | Chow et al. | 623/11 |
| 5,525,148 A * | 6/1996 | Chow et al. | 106/35 |
| 5,545,254 A | 8/1996 | Chow et al. | 106/35 |
| 5,681,872 A | 10/1997 | Erbe | 523/114 |
| 5,914,356 A | 6/1999 | Erbe | 523/114 |
| 5,939,039 A | 8/1999 | Sapieszko et al. | 423/311 |
| 6,136,029 A | 10/2000 | Johnson et al. | |
| 6,325,987 B1 * | 12/2001 | Sapieszko et al. | 423/305 |

FOREIGN PATENT DOCUMENTS

GB 2260538 4/1993

OTHER PUBLICATIONS

Abbona, F. et al., "Crystallization of calcium and magnesium phosphates from solutions of medium and low concentrations," *Cryst. Res. Technol.*, 1992, 27, 41–48.

Brown, P.W. et al., "Variations in solution chemistry during the low temperature formation of hydroxyapaptite," *J. Am. Ceram. Soc.*, 1991, 74(8), 1848–1854.

Chaair, H. et al., "Precipitation of stoichiometric apatitic tricalcium phosphate prepared by a continuous process," *J. Mater. Chem.*, 1995, 5(6), 895–899.

Driessens, F.C.M. et al., "Effective formulations for the preparation of calcium phosphate bone cements," *J. Mat. Sci.: Mat. Med.*, 1994, 5, 164–170.

Famery, R. et al., "Preparation of alpha–and beta–tricalcium phosphate ceramics, with and without magnesium addition," *Ceram. Int.*, 1994, 20, 327–336.

Fukase, Y. et al., "Setting reactions and compressive strengths of calcium phosphate cements," *J. Dent. Res.*, 1990, 69(12), 1852–1856.

Greenwood, N.N. et al., "Oxoacids of phosphorus and their salts," in *Chemistry of the Elements*, Pergamon Press, 1984, 586–595.

Ishikawa, K. et al., "Properties and mechanisms of fast–setting calcium phosphate cements," *J. Mat. Sci.: Mat. Med.*, 1995, 6, 528–533.

Kingery, W.D. et al. (eds.), *Introduction to Ceramics*, 2nd Edition, John Wiley & Sons, 1960, p. 416.

Koutsoukos, P. et al., "Crystallization of calcium phosphates. A constant composition study," *J. Am. Chem. Soc.*, 1980, 102, 1553–1557.

Lacout, J.L., "Calcium phosphate as bioceramics," in *Biomaterials—Hard Tissue Repair and Replacement*, Elsevier Science Publishers, 1992, 81–95.

LeGeros, R.Z., "Calcium Phosphates in Oral Biology and Medicine," *Monographs in Oral Science*, Meyers, H.M. (ed.), Karger Press, 1991, vol. 15, 108–129.

LeGeros, R.Z., "Biodegradation and bioresorption of calcium phospate ceramics," *Clin. Mat.*, 1993, 14(1), 65–88.

LeGeros, R.Z., "Preparation of octacalcium phosphate (OCP): A direct fast method," *Calcif. Tiss. Int.*, 1985, 37, 194–197.

(List continued on next page.)

Primary Examiner—Corrine McDermott
Assistant Examiner—A. Stewart
(74) Attorney, Agent, or Firm—Woodcock Washburn LLP

(57) ABSTRACT

Shaped, composite bodies are provided. One portion of the shaped bodies comprises an RPR-derived porous inorganic material, preferably a calcium phosphate. Another portion of the composite bodies is a different solid material, preferably metal, glass, ceramic or polymeric. The shaped bodies are especially suitable for orthopaedic and other surgical use.

45 Claims, 33 Drawing Sheets

OTHER PUBLICATIONS

Mirtchi, A. et al., "Calcium phosphate cements: Effect of fluorides on the setting and hardening of beta–tricalcium phosphate—dicalcium phosphate—calcite cements," *Biomat.*, 1991, 12, 505–510.

Monma, H. et al., "Properties of hydroxyapatite prepared by the hydrolysis of tricalcium phosphate," *J. Chem. Tech. Biotechnol.*, 1981, 31, 15–24.

Nancollas, G.H., "The involvement of calcium phosphates in biological mineralization and demineralization processes," *Pure Appl. Chem.*, 1992, 64(11), 1673–1678.

Nancollas, G.H., "In vitro studies of calcium phosphate crystallization," in *Biomineralization Chemical and Biochemical Perspectives*, 1989, 157–187.

Nancollas, G.H. et al., "Formation and dissolution mechanisms of calcium phosphates in aqueous systems," in *Hydroxyapatite and Related Materials*, CRC Press, Inc. 1994, 73–81.

Powell, S.J. et al., "The structure of ceramic foams prepared from polyurethane–ceramic suspension," *Materials & Manuf. Processes*, 1995, 10(4), 757–771.

Vereecke G. et al., "Calculation of the solubility diagrams in the system $Ca(OH)_2$—$H_3PO_4$—$KOH$—$HNO_3$—$CO_2$—$H_2O$," *J. Cryst. Growth*, 1990, 104, 820–832.

Wong, A.T.C. et al., "Prediction of precipitation and transformation behavior of calcium phosphate in aqueous media," in *Hydroxyapatite and Related Materials*, Brown, P.W. et al. (eds.), CRC Press, Inc., 1994, 189–196.

U.S. application No. 09/253,556, Sapieszko et al., filed Feb. 19, 1999.

* cited by examiner

COMPOSITE SHAPED BODIES AND METHODS FOR THEIR PRODUCTION AND USE

FIELD OF THE INVENTION

This invention relates to the preparation of composite shaped bodies, especially those having at least a portion comprising a calcium phosphate-containing material. This invention also relates to methods for preparing the bodies and to methods for use thereof. In accordance with certain embodiments of this invention, shaped bodies are provided which are at once, possessed of two or more portions having different properties. In accordance with other preferred embodiments, at least one portion of the composite is highly porous and uniform in composition. The shaped bodies can be produced in a wide range of geometric configurations through novel, low temperature techniques. The shaped bodies of the invention can have portions which are highly and uniformly porous while being self-supporting. They can be strengthened further using a variety of techniques, thereby forming porous composite structures. Such composite structures are useful as cell growth scaffolds, bone grafting materials, drug delivery vehicles, biological separation/purification media, catalysis and other supports and in a wide range of other uses. One of the most preferred uses for the composite structures of this invention is in the field of orthopaedic, restorative and reconstructive surgery. Thus the present invention provides shaped bodies having highly suitable combinations of properties which make those bodies extraordinarily useful for bone replacement, spinal repair, reconstructive, cosmetic and other surgeries.

BACKGROUND OF THE INVENTION

There has been a continuing need for improved methods for the preparation of mineral compositions, especially calcium phosphate-containing minerals. This long-felt need is reflected in part by the great amount of research found in the pertinent literature. While such interest and need stems from a number of industrial interests, the desire to provide materials which closely mimic mammalian bone for use in repair and replacement of such bone has been a major motivating force. Such minerals are principally calcium phosphate apatites as found in teeth and bones. For example, type-B carbonated hydroxyapatite $[Ca_5(PO_4)_{3-x}(CO_3)_x(OH)]$ is the principal mineral phase found in the body, with variations in protein and organic content determining the ultimate composition, crystal size, morphology, and structure of the body portions formed therefrom.

Calcium phosphate ceramics have been fabricated and implanted in mammals in various forms including, but not limited to, shaped bodies and cements. Different stoichiometric compositions such as hydroxyapatite (HAp), tricalcium phosphate (TCP), tetracalcium phosphate (TTCP), and other calcium phosphate salts and minerals, have all been employed to this end in an attempt to match the adaptability, biocompatibility, structure, and strength of natural bone. The role of pore size and porosity in promoting revascularization, healing, and remodeling of bone is now recognized as a critical property for bone replacement materials. Despite tremendous efforts directed to the preparation of porous calcium phosphate materials for such uses, significant shortcomings still remain. This invention overcomes those shortcomings and describes porous calcium phosphate and a wide variety of other inorganic materials which, in the case of calcium phosphates, closely resemble bone, and methods for the fabrication of such materials as shaped bodies for biological, chemical, industrial, and many other applications.

Early ceramic biomaterials exhibited problems derived from chemical and processing shortcomings that limited stoichiometric control, crystal morphology, surface properties, and, ultimately, reactivity in the body. Intensive milling and comminution of natural minerals of varying composition was required, followed by powder blending and ceramic processing at high temperatures to synthesize new phases for use in vivo.

A number of patents have issued which relate to ceramic biomaterials and are incorporated herein by reference. Among these are U.S. Pat. No. 4,880,610, B. R. Constantz ,"In situ calcium phosphate minerals—method and composition;" U.S. Pat. No. 5,047,031, B. R. Constantz, "In situ calcium phosphate minerals method;" U.S. Pat. No. 5,129,905, B. R. Constantz, "Method for in situ prepared calcium phosphate minerals;" U.S. Pat. No. 4,149,893, H. Aoki, et al, "Orthopaedic and dental implant ceramic composition and process for preparing same;" U.S. Pat. No. 4,612,053, W. E. Brown, et al, "Combinations of sparingly soluble calcium phosphates in slurries and pastes as mineralizers and cements;" U.S. Pat. No. 4,673,355, E. T. Farris, et al, "Solid calcium phosphate materials;" U.S. Pat. No. 4,849,193, J. W. Palmer, et al., "Process of preparing hydroxyapatite;" U.S. Pat. No. 4,897,250, M. Sumita, "Process for producing calcium phosphate;" U.S. Pat. No. 5,322,675, Y. Hakamatsuka, "Method of preparing calcium phosphate;" U.S. Pat. No. 5,338,356, M. Hirano, et al "Calcium phosphate granular cement and method for producing same;" U.S. Pat. No. 5,427,754, F. Nagata, et al., "Method for production of platelike hydroxyapatite;" U.S. Pat. No. 5,496,399, I. C. Ison, et al., "Storage stable calcium phosphate cements;" U.S. Pat. No. 5,522,893, L. C. Chow. et al., "Calcium phosphate hydroxyapatite precursor and methods for making and using same;" U.S. Pat. No. 5,545,254, L. C. Chow, et al., "Calcium phosphate hydroxyapatite precursor and methods for making and using same;" U.S. Pat. No. 3,679,360, B. Rubin, et al., "Process for the preparation of brushite crystals;" U.S. Pat. No. 5,525,148, L. C. Chow, et al., "Self-setting calcium phosphate cements and methods for preparing and using them;" U.S. Pat. No. 5,034,352, J. Vit, et al., "Calcium phosphate materials;" and U.S. Pat. No. 5,409,982, A. Imura, et al "Tetracalcium phosphate-based materials and process for their preparation."

Several patents describe the preparation of porous inorganic or ceramic structures using polymeric foams impregnated with a slurry of preformed ceramic particles. These are incorporated herein by reference: U.S. Pat. No. 3,833,386, L. L. Wood, et al, "Method of preparing porous ceramic structures by firing a polyurethane foam that is impregnated with inorganic material;" U.S. Pat. No. 3,877,973, F. E. G. Ravault, "Treatment of permeable materials;" U.S. Pat. No. 3,907,579, F. E. G. Ravault, "Manufacture of porous ceramic materials;" and U.S. Pat. No. 4,004,933, F. E. G. Ravault, "Production of porous ceramic materials." However, none of aforementioned art specifically describes the preparation of porous metal or calcium phosphates and none employs the methods of this invention.

The prior art also describes the use of solution impregnated-polymeric foams to produce porous ceramic articles and these are incorporated herein by reference: U.S. Pat. No. 3,090,094, K. Schwartzwalder, et al, "Method of making porous ceramic articles;" U.S. Pat. No. 4,328,034 C. N. Ferguson, "Foam Composition and Process;" U.S. Pat. No. 4,859,383, M. E. Dillon, "Process of Producing a Composite Macrostructure of Organic and Inorganic Materials;" U.S. Pat. No. 4,983,573, J. D. Bolt, et al, "Process for making 90° K superconductors by impregnating cellulosic article with precursor solution;" U.S. Pat. No. 5,219,829, G. Bauer, et al, "Process and apparatus for the preparation of pulverulent metal oxides for ceramic compositions;" GB 2,260,538, P. Gant, "Porous ceramics;" U.S. Pat. No. 5,296,261, J. Bouet, et al, "Method of manufacturing a sponge-type support for an electrode in an electrochemical cell;" U.S. Pat. No. 5,338,334, Y. S. Zhen, et al, "Process for preparing submicron/nanosize ceramic powders from precursors incorporated within a polymeric foam;" and S. J. Powell and J. R. G. Evans, "The structure of ceramic foams prepared from polyurethane-ceramic suspensions," Materials & Manufacturing Processes, 10(4):757 (1995). The focus of this art is directed to the preparation of either metal or metal oxide foams and/or particles. None of the disclosures of these aforementioned references mentions in situ solid phase formation via redox precipitation reaction from homogeneous solution as a formative method.

The prior art also discloses certain methods for fabricating, inorganic shaped bodies using natural, organic objects. These fabrication methods, however, are not without drawbacks which include cracking upon drying the green body and/or upon firing. To alleviate these problems, the fabrication processes typically involve controlled temperature and pressure conditions to achieve the desired end product. In addition, prior fabrication methods may include the additional steps of extensive material preparation to achieve proper purity, particle size distribution and orientation, intermediate drying and radiation steps, and sintering at temperatures above the range desired for employment in the present invention. For example, U.S. Pat. No. 5,298,205 issued to Hayes et. al. entitled "Ceramic Filter Process", incorporated herein by reference, discloses a method of fabricating a porous ceramic body from an organic sponge saturated in an aqueous slurry comprised of gluten and particulate ceramic material fired at a temperature range from 1,100° to 1,300° C. Hayes teaches that the saturated sponge must be dehydrated prior to firing via microwave radiation, and includes a pre-soak heating step, and a hot pressing step.

While improvements have been made in materials synthesis and ceramic processing technology leading to porous ceramics and ceramic biomaterials, improved preparative methods, and the final products these methods yield, are still greatly desired. Generation of controlled porosity in ceramic biomaterials generally, and in calcium phosphate materials in particular, is crucial to the effective in vitro and in vivo use of these synthetic materials for regenerating human cells and tissues. This invention provides both novel, porous calcium phosphate materials and methods for preparing them. Methods relating to calcium phosphate-containing biomaterials, which exhibit improved biological properties, are also greatly desired despite the great efforts of others to achieve such improvements.

In particular, this invention provides such novel, porous calcium phosphate and other materials in composite forms, especially in shaped bodies. Thus, the benefits of these novel materials are now enhanced through combining into such shaped bodies areas of the novel materials along with areas or portions comprising other materials.

Accordingly, it is a principal object of this invention to provide improved inorganic, porous, shaped bodies, especially those formed of calcium phosphate.

Such shaped bodies having a plurality of portions, one of which comprises the novel, inorganic, porous materials of this invention are also provide by this invention.

Another object is to provide shaped bodies for surgical, orthopaedic, reconstructive and restorative uses.

A further object of the invention is to provide methods for forming such materials with improved yields, lower processing temperatures, greater compositional flexibility, and better control of porosity.

Yet another object provides materials with micro-, meso-, and macroporosity, as well as the ability to generate shaped porous solids having improved uniformity, biological activity, catalytic activity, and other properties.

Another object is to provide porous materials which are useful in the repair and/or replacement of bone in orthopaedic and dental procedures.

An additional object is to prepare a multiplicity of high purity, complex shaped objects, formed at temperatures below those commonly used in traditional firing methods.

Further objects will become apparent from a review of the present specification.

SUMMARY OF THE INVENTION

The present invention is directed to new inorganic bodies, especially controllably porous bodies, which can be formed into virtually any geometric shape. The novel preparative methods of the invention utilize redox precipitation chemistry or aqueous solution chemistry, which is described in pending U.S. patent application Ser. No. 08/784,439 assigned to the present assignee and, incorporated herein by reference. In accordance with certain preferred embodiments, the redox precipitation chemistry is utilized in conjunction with a sacrificial, porous cellular support, such as an organic foam or sponge, to produce a porous inorganic product which faithfully replicates both the bulk geometric form as well as the macro-, meso-, and microstructure of the precursor organic support. The aqueous solution, because of its unique chemistry, has a high solids equivalent, yet can essentially be imbibed fully into and infiltrate thoroughly the microstructure of the sacrificial organic precursor material. This extent of infiltration allows the structural details and intricacies of the precursor organic foam materials to be reproduced to a degree heretofore unattainable. This great improvement can result in porous, inorganic materials having novel microstructural features and sufficient robustness to be handled as coherent bodies of highly porous solid.

The invention also gives rise to porous inorganic materials having improved compositional homogeneity, multiphasic character, and/or modified crystal structures at temperatures far lower than those required in conventional formation methods. In addition, the invention also gives rise to porous inorganic composites comprising mineral scaffolds strengthened and/or reinforced with polymers, especially film-forming polymers, such as gelatin.

The present invention is also directed to composite shaped bodies comprising two or more portions. One of the portions is the reaction product of a metal cation and an oxidizing agent together with a precursor anion oxidizable by the oxidizing agent. The reaction is one which gives rise to at least on gaseous product. Another portion of the composite shaped bodies of the invention is another solid. Such solid may be any of a wide range of materials such as metal, especially titanium, stainless steel and other surgical metals, ceramic, glass, polymer or other generally hard material. The composite shaped bodies are ideally suited for surgical use, especially in orthopaedics and in reconstructive and restorative surgery. The porous materials forming one portion of the composite bodies of the invention are high compatible with such surgical use and can give rise to osteogenesis or osteostimulation in some cases. This is especially true of calcium phosphate materials.

The new paradigm created by this invention is facilitated by a definition of terms used in the description of embodiments. The general method starts with infiltrant solutions produced from raw materials described herein as salts, aqueous solutions of salts, stable hydrosols or other stable dispersions, and/or inorganic acids. The sacrificial, porous organic templates used in some embodiments may be organic foams, cellular solids and the like, especially open-cell hydrophilic material which can imbibe the aqueous infiltrant solutions. Both the precursor organic templates, as well as the inorganic replicas produced in accordance within this invention, display a porosity range of at least 3 orders of magnitude. This range of porosity can be described as macro-, meso- and microporous. Within the scope of this invention, macroporosity is defined as having a pore diameter greater than or equal to 100 microns, mesoporosity is defined as having a pore diameter less than 100 microns but greater than or equal to 10 microns, and microporosity is defined as having a pore diameter less than 10 microns.

In addition to the controlled macro-, meso- and microporosity ranges, inorganic shaped bodies have been fabricated possessing pore volumes of at least about 30%. In preferred embodiments, pore volumes of over 50% have been attained and pore volumes in excess of 70% or 80% are more preferred. Materials having macro-, meso- and microporosity together with pore volumes of at least about 90% can be made as can those having pore volumes over 92% and even 94%. In some cases, pore volumes approaching 95% have been ascertained in products which, nevertheless, retain their structural integrity and pore structure.

The phases produced by the methods of this invention [Redox Precipitation Reaction (RPR) and HYdrothermal PROCESSING (HYPR)] initially are intermediate or precursor minerals, which can be easily converted to a myriad of pure and multiphasic minerals of previously known and, in some cases, heretofore undefined stoichiometry, generally via a thermal treatment under modest firing regimens compared to known and practiced conventional art.

In accordance with certain embodiments of the present invention, methods are provided for the restoration of bony tissue. In this regard, an area of bony tissue requiring repair as a result of disease, injury, desired reconfiguration and the like, is identified and preferably measured. A block of porous calcium phosphate material can be made to fit the dimensions of the missing or damaged bony tissue and implanted in place by itself or in conjunction with biocompatible bonding material compositions such as those disclosed in U.S. Pat. No. 5,681,872 issued in the name of E. M. Erbe on Oct. 28, 1997 and incorporated herein by reference. The calcium phosphate material can also be used as a "sleeve" or form for other implants, as a containment vessel for the bone grafting material which is introduced into the sleeve for the repair, and in many other contexts.

A major advantage of the restoration is that after polymerization, it has a significant, inherent strength, such that restoration of load-bearing bony sites can be achieved. While immobilization of the effected part will likely still be required, the present invention permits the restoration of many additional bony areas than has been achievable heretofore. Further, since the porous calcium phosphate scaffolding material of the present invention is biocompatible and, indeed, bioactive, osteogenesis can occur. This leads to bone infiltration and replacement of the calcium phosphate matrix with autologous bone tissue.

The calcium phosphate scaffolding material of the present invention may also be made into shaped bodies for a variety of uses. Thus, orthopaedic appliances such as joints, rods, pins, or screws for orthopaedic surgery, plates, sheets, and a number of other shapes may be formed from the material in and of itself or used in conjunction with conventional appliances that are known in the art. Such hardened compositions can be bioactive and can be used, preferably in conjunction with hardenable compositions in accordance with the present invention in the form of gels, pastes, or fluids, in surgical techniques. Thus, a screw or pin can be inserted into a broken bone in the same way that metal screws and pins are currently inserted, using conventional bone cements or restoratives in accordance with the present invention or otherwise. The bioactivity of the present hardenable materials give rise to osteogenesis, with beneficial medical or surgical results.

The methods of the invention are energy efficient, being performed at relatively low temperature; have high yields; and are amenable to careful control of product shape, macro- and microstructure, porosity, and chemical purity. Employment as bioactive ceramics is a principal, anticipated use for the materials of the invention, with improved properties being extant. Other uses of the porous minerals and processes for making the same are also within the spirit of the invention.

The present invention also provides exceptionally fine, uniform powders of inorganic materials. Such powders have uniform morphology, uniform composition and narrow size distribution. They may be attained through the comminution of shaped bodies in accordance with the invention and have wide utility in chemistry, industry, medicine and otherwise.

BRIEF DESCRIPTION OF THE DRAWINGS

FIGS. 20 and 22, together, demonstrate the presence of macro-, meso-, and microporosity simultaneously in a highly porous product.

FIG. 31 shows one embodiment of a synthetic cortical bone dowel in place. The dowel has a plurality of ports, some of which are shown 224.

FIG. 32 depicts another bone dowel for spinal fusion.

FIG. 33 shows a synthetic cortical interbody vertebral defect filling form.

FIG. 34 shows a cross section of a spinal fusion employing a shaped body of the invention potted in hardenable material.

FIGS. 35b and 35c are in the shape of rings.

DETAILED DESCRIPTION OF PREFERRED EMBODIMENTS

Figure 1:
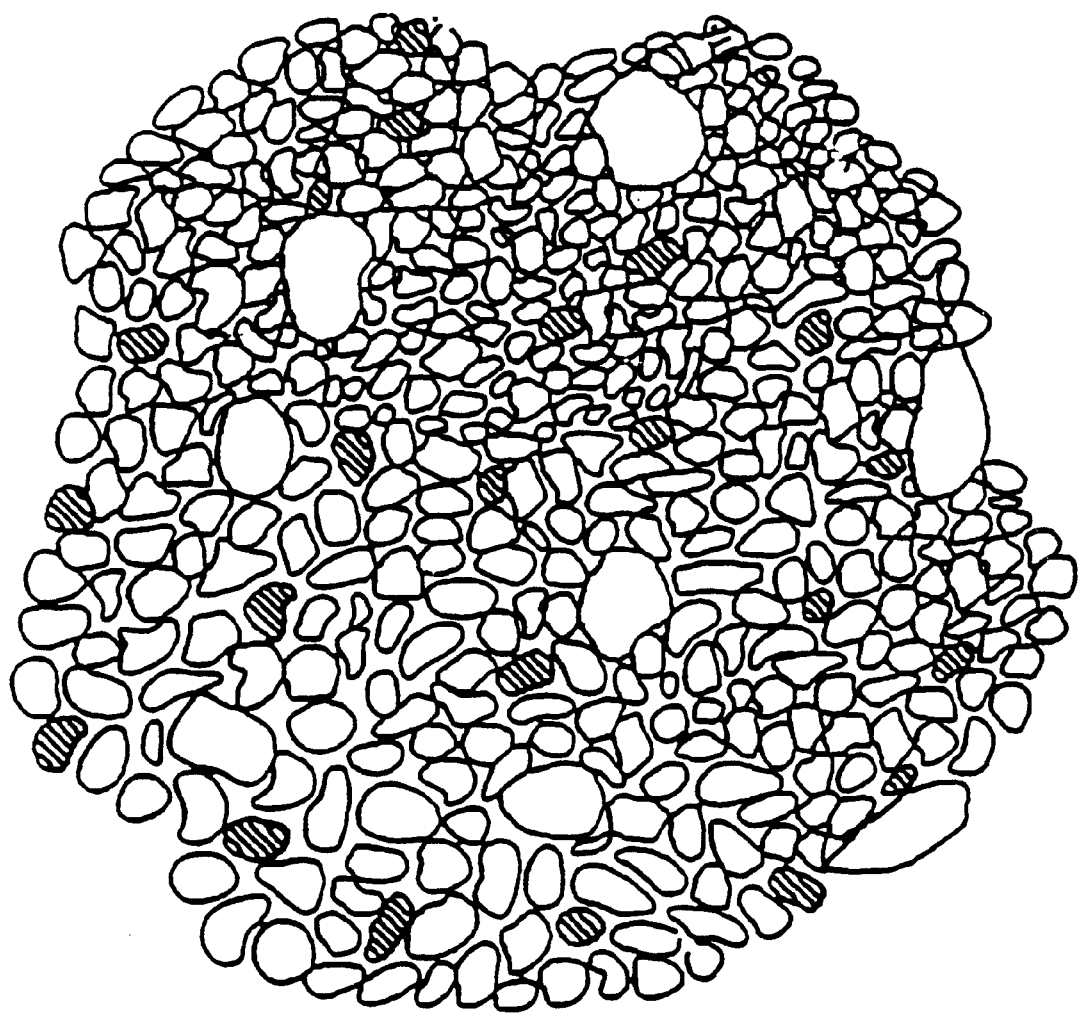
FIG. 1 depicts an aggregated physical structure of an RPR generated, multiphasic β-tricalcium phosphate (β-TCP)+ type-B carbonated apatite (c-HAp) [β-Ca3(PO4)2+Ca5(PO$_4$)3-x(CO3)x(OH)] prepared in accordance with one embodiment of this invention. The entire agglomerated particle is approximately 10 μm, and the individual crystallites are typically less than about 1 μm and relatively uniform in particle size and shape.

In accordance with this invention, composite shaped bodies are provided which are useful, e.g. in orthopaedic and other surgery. The bodies have a first portion which is a solid and which is attached to, adhered to, coformed with or in contact with a second portion. The second portion is reaction product of a blend comprising at least one metal cation at least one oxidizing agent; and at least one precursor anion oxidizable by said oxidizing agent to form an oxoanion. The reaction gives rise to at least one gaseous product and is generally of the type of reaction known as oxidation-reduction reactions. This results in what is termed an RPR-derived material. The resulting composite shaped bodies may be formed into nearly any shape, including shapes useful in orthopaedic and other surgery, especially when the RPR-derived material is a calcium phosphate.

The RPR-derived material is usually arrived at in two stages. Thus, a precursor mineral is formed from an immediate oxidation-reduction reaction, and then that material is consolidated or transformed into a final calcium phosphate or other material. In accordance with the present invention, methods are provided for preparing shapes comprising an intermediate precursor mineral of at least one metal cation and at least one oxoanion. These methods comprise preparing an aqueous solution of the metal cation and at least one oxidizing agent. The solution is augmented with at least one soluble precursor anion oxidizable by said oxidizing agent to give rise to the precipitant oxoanion. The oxidation-reduction reaction thus contemplated is conveniently initiated by heating the solution under conditions of temperature and pressure effective to give rise to said reaction. In accordance with preferred embodiments of the invention, the oxidation-reduction reaction causes at least one gaseous product to evolve and the desired intermediate precursor mineral to precipitate from the solution.

The intermediate precursor mineral thus prepared can either be used "as is" or can be treated in a number of ways. Thus, it may be heat treated in accordance with one or more paradigms to give rise to a preselected crystal structure or other preselected morphological structures therein. In accordance with preferred embodiments, the oxidizing agent is nitrate ion and the gaseous product is a nitrogen oxide, generically depicted as $NO_{x(g)}$. It is preferred that the precursor mineral provided by the present methods be substantially homogeneous. It is also preferred for many embodiments that the temperature reached by the oxidation-reduction reaction not exceed about 150° C. unless the reaction is run under hydrothermal conditions or in a pressure vessel.

In accordance with other preferred embodiments, the intermediate precursor mineral provided by the present invention is a calcium phosphate. It is preferred that such mineral precursor comprise, in major proportion, a solid phase which cannot be identified singularly with any conventional crystalline form of calcium phosphate. At the same time, the calcium phosphate mineral precursors of the present invention are substantially homogeneous and do not comprise a physical admixture of naturally occurring or conventional crystal phases.

In accordance with preferred embodiments, the low temperature processes of the invention lead to the homogeneous precipitation of high purity powders from highly concentrated solutions. Subsequent modest heat treatments convert the intermediate material to e.g. novel monophasic calcium phosphate minerals or novel biphasic β-tricalcium phosphate (β-TCP)+type-B, carbonated apatite (c-HAp) [β-Ca$_3$(PO$_4$)$_2$+Ca$_5$(PO$_4$)$_{3-x}$(CO$_3$)x(OH)] particulates.

In other preferred embodiments, calcium phosphate salts are provided through methods where at least one of the precursor anions is a phosphorus oxoanion, preferably introduced as hypophosphorous acid or a soluble alkali or alkaline-earth hypophosphite salt. For the preparation of such calcium phosphates, it is preferred that the initial pH be maintained below about 3, and still more preferably below about 1.

The intermediate precursor minerals prepared in accordance with the present methods are, themselves, novel and not to be expected from prior methodologies. Thus, such precursor minerals can be, at once, non-stoichiometric and possessed of uniform morphology.

It is preferred in connection with some embodiments of the present invention that the intermediate precursor minerals produced in accordance with the present methods be heated, or otherwise treated, to change their properties. Thus, such materials may be heated to temperatures as low as 300° C. up to about 800° C. to give rise to certain beneficial transformations. Such heating will remove extraneous materials from the mineral precursor, will alter its composition and morphology in some cases, and can confer upon the mineral a particular and preselected crystalline structure. Such heat treatment can be to temperatures which are considerably less than those used conventionally in accordance with prior methodologies to produce end product mineral phases. Accordingly, the heat treatments of the present invention do not, necessarily, give rise to the "common" crystalline morphologies of monetite, dicalcium or tricalcium phosphate, tetracalcium phosphate, etc., but, rather, they can lead to new and unobvious morphologies which have great utility in the practice of the present invention.

The present invention is directed to the preparation, production and use of shaped bodies of inorganic materials. It will be appreciated that shaped bodies can be elaborated in a number of ways, which shaped bodies comprise an inorganic material. A preferred method for giving rise to the shaped bodies comprising minerals is through the use of subject matter disclosed in U.S. Ser. No. 08/784,439 filed Jan. 16, 1997, assigned to the assignee of the present invention and incorporated herein by reference. In accordance with techniques preferred for use in conjunction with the present invention, a blend of materials are formed which can react to give rise to the desired mineral, or precursor thereof, at relatively low temperatures and under relatively flexible reaction conditions. Preferably, the reactive blends thus used include oxidizing agents and materials which can be oxidized by the oxidizing agent, especially those which can give rise to a phosphorus oxoanion. Many aspects of this chemistry are described hereinafter in the present specification. It is to be understood, however, that such reactive blends react at modest temperatures under modest reaction conditions, usually through the evolution of a nitrogen oxide gas, to give rise to the minerals desired for preparation or to materials which may be transformed such as through heating or sintering to form such minerals. A principal object of the present invention is to permit such minerals to be formed in the form of shaped bodies.

It will be appreciated that preferred compositions of this invention exhibit high degrees of porosity. It is also preferred that the porosity occur in a wide range of effective pore sizes. In this regard, persons skilled in the art will appreciate that preferred embodiments of the invention have, at once, macroporosity, mesoporosity and microporosity. Macroporosity is characterized by pore diameters greater than about 100 μm. Mesoporosity is characterized by pore diameters between about 100 and 10 μm, while microporosity occurs when pores have diameters below about 10 μm. It is preferred that macro-, meso- and microporosity occur simultaneously in products of the invention. It is not necessary to quantify each type of porosity to a high degree. Rather, persons skilled in the art can easily determine whether a material has each type of porosity through examination, such as through the preferred method of scanning electron microscopy. While it is certainly true that more than one or a few pores within the requisite size range are needed in order to characterize a sample as having a substantial degree of that particular form of porosity, no specific number or percentage is called for. Rather, a qualitative evaluation by persons skilled in the art shall be used to determine macro-, meso- and microporosity.

It is preferred that the overall porosity of materials prepared in accordance with this invention be high. This characteristic is measured by pore volume, expressed as a percentage. Zero percent pore volume refers to a fully dense material, which, perforce, has no pores at all. One hundred percent pore volume cannot meaningfully exist since the same would refer to "all pores" or air. Persons skilled in the art understand the concept of pore volume, however and can easily calculate and apply it. For example, pore volume may be determined in accordance with W. D. Kingery, *Introduction to Ceramics,* 1960 p. 416 (Wiley, 1060), who provides a formula for determination of porosity. Expressing porosity as a percentage yields pore volume. The formula is: Pore Volume=$(1-f_p)$ 100%, where $f_p$ is fraction of theoretical density achieved.

Pore volumes in excess of about 30% are easily achieved in accordance with this invention while materials having pore volumes in excess of 50 or 60% are also routinely attainable. It is preferred that materials of the invention have pore volumes of at least about 75%. More preferred are materials having pore volumes in excess of about 85%, with 90% being still more preferred. Pore volumes greater than about 92% are possible as are volumes greater than about 94%. In some cases, materials with pore volumes approaching 95% can be made in accordance with the invention. In preferred cases, such high pore volumes are attained while also attaining the presence of macro-, meso- and microporosity as well as physical stability of the materials produced. It is believed to be a great advantage to be able to prepare inorganic shaped bodies having macro-, meso- and microporosity simultaneously with high pore volumes as described above.

It has now been found that such shaped bodies may be formed from minerals in this way which have remarkable macro- and microstructures. In particular, a wide variety of different shapes can be formed and bodies can be prepared which are machinable, deformable, or otherwise modifiable into still other, desired states. The shaped bodies have sufficient inherent physical strength allowing that such manipulation can be employed. The shaped bodies can also be modified in a number of ways to increase or decrease their physical strength and other properties so as to lend those bodies to still further modes of employment. Overall, the present invention is extraordinarily broad in that shaped mineral bodies may be formed easily, inexpensively, under carefully controllable conditions, and with enormous flexibility. Moreover, the microstructure of the materials that can be formed from the present invention can be controlled as well, such that they may be caused to emulate natural bone, to adopt a uniform microstructure, to be relatively dense, relatively porous, or, in short, to adopt a wide variety of different forms. The ability to control in a predictable and reproducible fashion the macrostructure, microstructure, and mineral identity of shaped bodies in accordance with the present invention under relatively benign conditions using inexpensive starting materials lends the technologies of the present invention to great medical, chemical, industrial, laboratory, and other uses.

In accordance with certain preferred embodiments of the present invention, a reactive blend in accordance with the invention is caused to be imbibed into a material which is capable of absorbing it. It is preferred that the material have significant porosity, be capable of absorbing significant amounts of the reactive blend via capillary action, and that the same be substantially inert to reaction with the blend prior to its autologous oxidation-reduction reaction. It has been found to be convenient to employ sponge materials, especially cellulose sponges of a kind commonly found in household use for this purpose. Other sponges, including those which are available in compressed form such as Normandy sponges, are also preferred in certain embodiments. The substrate used to imbibe the reactive blend, however, are not limited to organic materials and can include inorganic materials such as fiberglass.

The sponges are caused to imbibe the reactive blend in accordance with the invention and are subsequently, preferably blotted to remove excess liquid. The reactive blend-laden sponge is then heated to whatever degree may be necessary to initiate the oxidation-reduction reaction of the reactive blend. Provision is generally made for the removal of by-product noxious gases, chiefly nitrogen oxide gases, from the site of the reaction. The reaction is exothermic, however the entire reacted body does not generally exceed a few hundred degrees centigrade. In any event, the reaction goes to completion, whereupon what is seen is an object in the shape of the original sponge which is now intimately comprised of the product of the oxidation reduction reaction. This material may either be the finished, desired mineral, or may be a precursor from which the desired product may be obtained by subsequent PROCESSING.

Following the initial oxidation-reduction reaction, it is convenient and, in many cases, preferred to heat treat the reacted product so as to eliminate the original sponge. In this way, the cellulosic component of the sponge is pyrolyzed in a fugitive fashion, leaving behind only the mineral and in some cases, a small amount of ash. The resulting shaped body is in the form of the original sponge and is self-supporting. As such, it may be used without further transformation or it may be treated in one or more ways to change its chemical and or physical properties. Thus, the shaped body following the oxidation-reduction reaction, can be heat treated at temperatures of from about 250° C. to about 1400° C., preferably from 500° C. to about 1000° C., and still more preferably from about 500° C. to about 800° C. Thus, a precursor mineral formed from the oxidation-reduction reaction may be transformed into the final mineral desired for ultimate use. A number of such transformations are described in the examples to the present application and still others will readily occur to persons skilled in the art.

It will be appreciated that temperatures in excess of 250° C. may be employed in initiating the oxidation-reduction reaction and, indeed, any convenient temperature may be so utilized. Moreover, methods of initiating the reaction where the effective temperature is difficult or impossible to determine, such a microwave heating, may also be employed. The preferred procedures, however, are to employ reaction conditions to initiate, and propagate if necessary, the reaction are below the temperature wherein melting of the products occur. This is in distinction with conventional glass and ceramic processing methods.

The shaped bodies thus formed may be used in a number of ways directly or may be further modified. Thus, either the as-formed product of the oxidation-reduction reaction may be modified, or a resulting, transformed mineral structure may be modified, or both. Various natural and synthetic polymers, pre-polymers, organic materials, metals and other adjuvants may be added to the inorganic structures thus formed. Thus, wax, glycerin, gelatin, pre-polymeric materials such as precursors to various nylons, acrylics, epoxies, polyalkylenes, and the like, may be caused to permeate all or part of the shaped bodies formed in accordance with the present invention. These may be used to modify the physical and chemical nature of such bodies. In the case of polymers, strength modifications may easily be obtained. Additionally, such materials may also change the chemical nature of the minerals, such as by improving their conductivity, resistance to degradation, electrolytic properties, electrochemical properties, catalytic properties, or otherwise. All such modifications are contemplated by the present invention.

As will be appreciated, the shaped bodies prepared in accordance with the present invention may be formed in a very large variety of shapes and structures. It is very easy to form cellulose sponge material into differing shapes such as rings, rods, screw-like structures, and the like. These shapes, when caused to imbibe a reactive blend, will give rise to products which emulate the original shapes. It is also convenient to prepare blocks, disks, cones, frustrums or other gross shapes in accordance with the present invention which shapes can be machined, cut, or otherwise manipulated into a final desired configuration. Once this has been done, the resulting products may be used as is or may be modified through the addition of gelatin, wax, polymers, and the like, and used in a host of applications.

When an inherently porous body such as a sponge is used as a substrate for the imbibition of reactive blend and the subsequent elaboration of oxidation-reduction product, the resulting product replicates the shape and morphology of the sponge. Modifications in the shape of the sponge, and in its microstructure can give rise to modifications in at least the intermediate structure and gross structures of the resulting products. It has been found, however, that the microstructure of shaped bodies prepared in accordance with the present invention frequently include complex and highly desirable features. Thus, on a highly magnified scale, microstructure of materials produced in accordance with the present invention can show significant microporosity. In several embodiments of the present invention, the microstructure can be custom-tailored based upon the absorbent material selected as the fugitive support. One particular embodiment, which used a kitchen sponge as the absorbent material, exhibited a macro- and microstructure similar to the appearance of ovine trabecular bone. This highly surprising, yet highly desirable result gives rise to obvious benefits in terms of the replication of bony structures and to the use of the present invention in conjunction with the restoration of bony tissues in animals and especially in humans.

Other macro- and microstructures may be attained through the present invention, however. Thus, through use of the embodiments of the present invention, great diversity may be attained in the preparation of mineral structures not only on a macroscopic but also on a microscopic level. Accordingly, the present invention finds utility in a wide variety of applications. Thus, the shaped bodies may be used in medicine, for example for the restoration of bony defects and the like. The materials may also be used for the delivery of medicaments internal to the body. In this way, the porosity of a material formed in accordance with the invention may be all or partially filled with another material which either comprises or carries a medicament such as a growth hormone, antibiotic, cell signaling material, or the like. Indeed, the larger porous spaces within some of the products of the present invention may be used for the culturing of cells within the human body. In this regard, the larger spaces are amenable to the growth of cells and can be permeated readily by bodily fluids such as certain blood components. In this way, growing cells may be implanted in an animal through the aegis of implants in accordance with the present invention. These implants may give rise to important biochemical or therapeutic or other uses.

The invention finds great utility in chemistry as well. Shaped bodies formed from the present invention may be formed to resemble saddles, rings, disks, honeycombs, spheres, tubes, matrixes, and, in short, a huge array of shapes, which shapes may be used for engineering purposes. Thus, such shapes may be made from minerals which incorporate catalytic components such as rare earths, precious and base metals, palladium, platinum, Raney nickel and the like for catalytic use. These shapes may also be used for column packing for distillation and other purposes. Indeed, the shapes may be capable of serving a plurality of uses at once, such as being a substrate for refluxing while acting as a catalyst at the same time.

The bodies of the present invention will also be suitable for chromatography and other separation and purification techniques. Thus, they may serve as substrates for mobile phases in the same way that a capillary suspends a gelatinous material for capillary gel electrophoresis.

The present invention also provides filtration media. As is apparent, the porous structures of the present invention may serve as filters. Due to the ability to formulate these shaped bodies in a wide variety of carefully controlled ways, some unique structures may be attained. Thus, an anisotropic membrane, as known to persons of ordinary skill in the art, and frequently referred to as a "Michaels" membrane may be used for the imbibation of reactive blend in accordance with the invention. Following redox reaction and removal of the membranous material as a fugitive phase, the resulting inorganic structure is also anisotropic. It is thus possible to utilize materials and shaped bodies in accordance with the present invention as an anisotropic but inorganic filtration media. Since it is also possible to include a number of inorganic materials therein, such filters may be caused to be inherently bacteriostatic and non-fouling. It has been shown, heretofore, that anisotropic membranes such as polysulfone and other membranes are capable of nurturing and growing cells for the purposes of delivering cellular products into a reaction screen. It is now possible to accomplish the same goals using wholly inorganic structures prepared in accordance with this invention.

In addition to the foregoing, it is possible to prepare and modify shaped bodies in accordance with the present invention in a variety of other ways. Thus, the shaped bodies may be coated, such as with a polymer. Such polymers may be any of the film forming polymers or otherwise and may be used for purposes of activation, conductivity, passivation, protection, or other chemical and physical modification. The bodies may also be contacted with a "keying agent" such as a silane, or otherwise to enable the grafting of different materials onto the surface of the polymer.

The shaped bodies of the invention may also be used for the growth of oligomers on their surfaces. This can be done in a manner analogous to a Merrifield synthesis, an oligonucleotide synthesis or otherwise. Such shaped bodies may find use in conjunction with automated syntheses of such oligomers and may be used to deliver such oligomers to the body of an animal, to an assay, to a synthetic reaction vessel, or otherwise. Since the mineral composition of the shaped bodies of this invention may be varied so widely, it is quite suitable to the elaboration of oligomers as suggested here and above. Grafting of other inorganic materials, silanes, especially silicones and similar materials, is a particular feature of the present invention. The grafting reactions, keying reactions, oligomer extension reactions and the like are all known to persons skilled in the art and will not be repeated here. Suffice it to say that all such reactions are included within the scope of the present invention.

The shaped bodies of the invention may also be coated through surface layer deposition techniques such as plasma coating, electroless plating, chemical vapor deposition (CVD), physical vapor deposition (PVD), or other methods. In such a way, the surface structure of the shaped bodies may be modified in carefully controlled ways for catalytic, electronic, and other purposes. The chemistry and physics of chemical vapor deposition and other coating techniques are known to persons of ordinary skill in the art whose knowledge is hereby assumed.

In accordance with other embodiments of the invention, the shaped bodies produced hereby may be comminuted to yield highly useful and unique powder materials finding wide utility. Thus, shaped bodies may be crushed, milled, etc. and preferably classified or measured, such as with a light scattering instrument, to give rise to fine powders. Such powders are very small and highly uniform, both in size, shape and chemical composition. Particles may be prepared having particle size number means less than about 0.1 $\mu$m or 100 nanometers. Smaller mean sized may also be attained. Thus, this invention provides highly uniform inorganic materials in powder form having particle sizes, measured by light scattering techniques such that the number mean size is between about 0.1 and 5.0 $\mu$m. Particle sizes between about 0.5 and 2.0 $\mu$m may also be attained. It may, in some embodiments, be desired to classify the powders in order to improve uniformity of size.

The morphology of the particles is highly uniform, deriving, it is thought, from the microporosity of the shaped bodies from which they arise. The particles are also highly uniform chemically. Since they arise from a chemical reaction from a fully homogenous solution, such uniformity is much greater than is usually found in glass or ceramic melts.

Particle size number means are easily determined with a Horiba LA-910 instrument. Number means refers to the average or mean number of particles having the size or size range in question.

Such powders are very useful, finding use in cosmetics, pharmaceuticals, excipients, additives, pigments, fluorescing agents, fillers, flow control agents, thixotropic agents, materials processing, radiolabels, and in may other fields of endeavor. For example, a molded golf ball may easily be made such as via the processes of Bartsch, including a calcium phosphate powder of this invention admixed with a crosslinked acrylic polymer system.

In conjunction with certain embodiments of the present invention, shaping techniques are employed on the formed, shaped bodies of the present invention. Thus, such bodies may be machined, pressed, stamped, drilled, lathed, or otherwise mechanically treated to adopt a particular shape both externally and internally. As will be appreciated, the internal microstructure of the bodies of the present invention can be altered thru the application of external force where such modifications are desired. Thus, preforms may be formed in accordance with the invention from which shapes may be cut or formed. For example, an orthopaedic sleeve for a bone screw may be machined from a block of calcium phosphate made hereby, and the same tapped for screw threads or the like. Carefully controllable sculpting is also possible such that precisely-machined shapes may be made for bioimplantation and other uses.

While many of the present embodiments rely upon the imbibation of reactive blends by porous, organic media such as sponges and the like, it should be appreciated that many other ways of creating shaped bodies in accordance with this invention also exist. In some of these embodiments, addition of materials, either organic or inorganic, which serve to modify the characteristic of the reactive blend may be beneficial. As an example of this, flow control agents may be employed. Thus, it may be desirable to admix a reactive blend in accordance with the invention together with a material such as a carboxymethyl or other cellulose or another binding agent to give rise to a paste or slurry. This paste or slurry may then be formed and the oxidation reduction reaction initiated to give rise to particular shapes. For example, shaped bodies may be formed through casting, extrusion, foaming, doctor blading, spin molding, spray forming, and a host of other techniques. It is possible to extrude hollow shapes in the way that certain forms of hollow pasta are extruded. Indeed, machinery useful for the preparation of certain food stuffs may also find beneficial use in conjunction with certain embodiments of the present invention. To this end, food extrusion materials such as that used for the extrusion of "cheese puffs" or puffed cereals may be used. These combine controllable temperature and pressure conditions with an extrusion apparatus. Through careful control of the physical conditions of the machinery, essentially finished, oxidation-reduction product may be extruded and used as-is or in subsequently modified form.

In accordance with certain embodiments, a film of reactive blend may be doctored onto a surface, such as stainless steel or glass, and the film caused to undergo an oxidation-reduction reaction. The resulting material can resemble a potato chip in overall structure with variable porosity and other physical properties.

In addition to the use of sponge material, the present invention is also amenable to the use of other organic material capable of imbibing reactive blend. Thus, if a gauze material is used, the resulting oxidation reduction product assumes the form of the gauze. A flannel material will give rise to a relatively thick pad of inorganic material from which the organic residue may be removed through the application of heat. Cotton or wool may be employed as may be a host of other organic materials.

It is also possible to employ inorganic materials and even metals in accordance with the present invention. Thus, inclusion of conductive mesh, wires, or conductive polymers in materials which form the substrate for the oxidation reduction of the reactive blend can give rise to conductive, mineral-based products. Since the minerals may be formed or modified to include a wide variety of different elements, the same may be caused to be catalytic. The combination of a porous, impermeable, catalytic material with conductivity makes the present invention highly amenable to use in fuel cells, catalytic converters, chemical reaction apparatus and the like.

In this regard, since the conductive and compositional character of the shaped bodies of the present invention may be varied in accordance with preselected considerations, such shapes may be used in electronic and military applications. Thus, the ceramics of the invention may be piezoelectric, may be transparent to microwave radiation and, hence, useful in radomes and the like. They may be ion responsive and, therefore, useful as electrochemical sensors, and in many other ways. The materials of the invention may be formulated so as to act as pharmaceutical excipients, especially when comminuted, as gas scrubber media, for pharmaceutical drug delivery, in biotechnological fermentation apparatus, in laboratory apparatus, and in a host of other applications.

As will be apparent from a review of the chemistry portion of the present specification, a very large variety of mineral species may be formed. Each of these may be elaborated into shaped bodies as described here and above. For example, transition metal phosphates including those of scandium, titanium, chromium, manganese, iron, cobalt, nickel, copper, and zinc may be elaborated into pigments, phosphors, catalysts, electromagnetic couplers, microwave couplers, inductive elements, zeolites, glasses, and nuclear waste containment systems and coatings as well as many others.

Rare earth phosphates can form intercalation complexes, catalysts, glasses, ceramics, radiopharmaceuticals, pigments and phosphors, medical imaging agents, nuclear waste solidification media, electro-optic components, electronic ceramics, surface modification materials and many others. Aluminium and zirconium phosphates, for example, can give rise to surface protection coatings, abrasive articles, polishing agents, cements, filtration products and otherwise.

Alkali and alkaline earth metal phosphates are particularly amenable to low temperature glasses, ceramics, biomaterials, cements, glass-metal sealing materials, glass-ceramic materials including porcelains, dental glasses, electro-optical glasses, laser glasses, specific refractive index glasses, optical filters and the like.

In short, the combination of easy fabrication, great variability in attainable shapes, low temperature elaboration, wide chemical composition latitude, and the other beneficial properties of the present invention lend it to a wide variety of applications. Indeed, other applications will become apparent as the full scope of the present invention unfolds over time.

In accordance with the present invention, the minerals formed hereby and the shaped bodies comprising them are useful in a wide variety of industrial, medical, and other fields. Thus, calcium phosphate minerals produced in accordance with preferred embodiments of the present invention may be used in dental and orthopaedic surgery for the restoration of bone, tooth material and the like. The present minerals may also be used as precursors in chemical and ceramic processing, and in a number of industrial methodologies, such as crystal growth, ceramic processing, glass making, catalysis, bioseparations, pharmaceutical excipients, gem synthesis, and a host of other uses. Uniform microstructures of unique compositions of minerals produced in accordance with the present invention confer upon such minerals wide utility and great "value added."Indeed, submicron microstructure can be employed by products of the invention with the benefits which accompany such microstructures.

Improved precursors provided by this invention yield lower formation temperatures, accelerated phase transition kinetics, greater compositional control, homogeneity, and flexibility when used in chemical and ceramic processes. Additionally, these chemically-derived, ceramic precursors have fine crystal size and uniform morphology with subsequent potential for very closely resembling or mimicking natural tissue structures found in the body.

Controlled precipitation of specific phases from aqueous solutions containing metal cations and phosphate anions represents a difficult technical challenge. For systems containing calcium and phosphate ions, the situation is further complicated by the multiplicity of phases that may be involved in the crystallization reactions as well as by the facile phase transformations that may proceed during mineralization. The solution chemistry in aqueous systems containing calcium and phosphate species has been scrupulously investigated as a function of pH, temperature, concentration, anion character, precipitation rate, digestion time, etc. (P. Koutsoukos, Z. Amjad, M. B. Tomson, and G. H. Nancollas, "Crystallization of calcium phosphates. A constant composition study," J. Am. Chem. Soc. 102: 1553 (1980); A. T. C. Wong. and J. T. Czernuszka, "Prediction of precipitation and transformation behavior of calcium phosphate in aqueous media," in Hydroxyapatite and Related Materials, pp 189–196 (1994), CRC Press, Inc.; G. H. Nancollas, "In vitro studies of calcium phosphate crystallization," in Biomineralization—Chemical and Biochemical Perspectives, pp 157–187 (1989)).

Solubility product considerations impose severe limitations on the solution chemistry. Furthermore, methods for generating specific calcium phosphate phases have been described in many technical articles and patents (R. Z. LeGeros, "Preparation of octacalcium phosphate (OCP): A direct fast method," Calcif. Tiss. Int. 37: 194 (1985)). As discussed above, none of this aforementioned art employs the present invention.

Several sparingly soluble calcium phosphate crystalline phases, so called "basic" calcium phosphates, have been characterized, including alpha- and beta-tricalcium phosphate ($\alpha$-TCP, $\beta$-TCP, $Ca_3(PO_4)_2$), tetracalcium phosphate (TTCP,$Ca_4(PO_4)_2O$), octacalcium phosphate (OCP, $Ca_4H(PO_4)_3.$-$nH_2O$, where 2<n<3), and calcium hydroxyapatite (HAp, $Ca_5(PO_4)_3(OH)$). Soluble calcium phosphate phases, so called "acidic" calcium phosphate crystalline phases, include dicalcium phosphate dihydrate (brushite -DCPD, $CaHPO_4.H_2O$), dicalcium phosphate anhydrous (monetite-DCPA, $CaHPO_4$), monocalcium phosphate monohydrate (MCPM, $Ca(H_2PO_4)_2$—$H_2O$), and monocalcium phosphate anhydrous (MCPA, $Ca(H_2PO_4)_2$). These calcium phosphate compounds are of critical importance in the area of bone cements and bone grafting materials. The use of DCPD, DCPA, ($\alpha$-TCP, $\beta$-TCP, TTCP, OCP, and HAp, alone or in combination, has been well documented as biocompatible coatings, fillers, cements, and bone-forming substances (F. C. M. Driessens, M. G. Boltong, O. Bermudez, J. A. Planell, M. P. Ginebra, and E. Fernandez, "Effective formulations for the preparation of calcium phosphate bone cements," J. Mat. Sci.: Mat. Med. 5: 164 (1994); R. Z. LeGeros, "Biodegradation and bioresorption of calcium phosphate ceramics," Clin. Mat. 14(1): 65 (1993); K. Ishikawa, S. Takagi, L. C. Chow, and Y. Ishikawa, "Properties and mechanisms of fast-setting calcium phosphate cements," J. Mat. Sci.: Mat. Med. 6: 528 (1995); A. A. Mirtchi, J. Lemaitre, and E. Munting, "Calcium phosphate cements: Effect of fluorides on the setting and hardening of beta-tricalcium phosphate-dicalcium phosphate-calcite cements," Biomat. 12: 505 (1991); J. L. Lacout, "Calcium phosphate as bioceramics," in Biomaterials—Hard Tissue Repair and Replacement, pp 81–95 (1992), Elsevier Science Publishers).

Generally, these phases are obtained via thermal or hydrothermal conversion of (a) solution-derived precursor calcium phosphate materials, (b) physical blends of calcium salts, or (c) natural coral. Thermal transformation of synthetic calcium phosphate precursor compounds to TCP or TTCP is achieved via traditional ceramic processing regimens at high temperature, greater than about 800° C. Thus, despite the various synthetic pathways for producing calcium phosphate precursors, the "basic" calcium phosphate materials used in the art (Ca/P$\geq$1.5) have generally all been subjected to a high temperature treatment, often for extensive periods of time. For other preparations of "basic" calcium phosphate materials, see also H. Monma, S. Ueno, and T. Kanazawa, "Properties of hydroxyapatite prepared by the hydrolysis of tricalcium phosphate," J. Chem. Tech. Biotechnol. 31: 15 (1981); H. Chaair, J. C. Heughebaert, and M. Heughebaert, "Precipitation of stoichiometric apatitic tricalcium phosphate prepared by a continuous process," J. Mater. Chem. 5(6): 895 (1995); R. Famery, N. Richard, and P. Boch, "Preparation of alpha- and beta-tricalcium phosphate ceramics, with and without magnesium addition," Ceram. Int. 20: 327 (1994); Y. Fukase, E. D. Eanes, S. Takagi, L. C. Chow, and W. E. Brown, "Setting reactions and compressive strengths of calcium phosphate cements," J. Dent. Res. 69(12): 1852 (1990).

The present invention represents a significant departure from prior methods for synthesizing metal phosphate minerals and porous shaped bodies of these materials, particularly calcium phosphate powders and materials, in that the materials are formed from homogeneous solution using a novel Redox Precipitation Reaction (RPR). They can be subsequently converted to TCP, HAp and/or combinations thereof at modest temperatures and short firing schedules. Furthermore, precipitation from homogeneous solution (PFHS) in accordance with this invention, has been found to be a means of producing particulates of uniform size and composition in a form heretofore not observed in the prior art.

The use of hypophosphite [$H_2PO_2^-$] anion as a precursor to phosphate ion generation has been found to be preferred since it circumvents many of the solubility constraints imposed by conventional calcium phosphate precipitation chemistry and, furthermore, it allows for uniform precipitation at high solids levels. For example, reactions can be performed in accordance with the invention giving rise to product slurries having in excess of 30% solids. Nitrate anion is the preferred oxidant, although other oxidizing agents are also useful.

The novel use of nitrate anion under strongly acidic conditions as the oxidant for the hypophosphite to phosphate reaction is beneficial from several viewpoints. Nitrate is readily available and is an inexpensive oxidant. It passivates stainless steel (type 316 SS) and is non-reactive to glass processing equipment. Its oxidation byproducts ($NO_x$) are manageable via well-known pollution control technologies, and any residual nitrate will be fugitive, as $NO_x$ under the thermal conversion schedule to which the materials are usually subjected, thus leading to exceedingly pure final materials.

Use of reagent grade metal nitrate salts and hypophosphorous acid, as practiced in this invention, will lead to metal phosphate phases of great purity.

Methods for producing useful calcium phosphate-based materials are achieved by reduction-oxidation precipitation reactions (RPR) generally conducted at ambient pressure and relatively low temperatures, usually below 250° C. and preferably below 200° C., most preferably below 150° C. The manner of initiating such reactions is determined by the starting raw materials, their treatment, and the redox electrochemical interactions among them.

The driving force for the RPR is the concurrent reduction and oxidation of anionic species derived from solution precursors. Advantages of the starting solutions can be realized by the high initial concentrations of ionic species, especially calcium and phosphorus species. It has been found that the use of reduced phosphorus compounds leads to solution stability at ionic concentrations considerably greater than if fully oxidized $[PO_4]^{-3}$ species were used. Conventional processing art uses fully oxidized phosphorus oxoanion compounds and is, consequently, hindered by pH, solubility, and reaction temperature constraints imposed by the phosphate anion.

Typical reducible species are preferably nitric acid, nitrate salts (e.g. $Ca(NO_3)_2 4H_2O$), or any other reducible nitrate compound, which is highly soluble in water. Other reducible species include nitrous acid ($HNO_2$) or nitrite ($NO2^-$) salts.

Among the oxidizable species which can be used are hypophosphorous acid or hypophosphite salts [e.g. $Ca(H_2PO_2)_2$] which are highly soluble in water. Other oxidizable species which find utility include acids or salts of phosphites ($HPO_3^{2-}$), pyrophosphites ($H_2P_2O_5^{2-}$), thiosulfate ($S_2O_3^{2-}$), tetrathionate ($S_4O_6^{2-}$), dithionite ($S_2O_4^{2-}$) trithionate ($S_3O_6^{2-}$), sulfite ($SO_3^{2-}$), and dithionate ($S_2O_6^{2-}$). In consideration of the complex inorganic chemistry of the oxoanions of Groups 5B, 6B, and 7B elements, it is anticipated that other examples of oxidizable anions can be utilized in the spirit of this invention.

The cation introduced into the reaction mixture with either or both of the oxidizing or reducing agents are preferably oxidatively stable (i.e. in their highest oxidation state). However, in certain preparations, or to effect certain reactions, the cations may be introduced in a partially reduced oxidation state. Under these circumstances, adjustment in the amount of the oxidant will be necessary in order to compensate for the electrons liberated during the oxidation of the cations during RPR.

It is well known in the art that for solutions in equilibrium with ionic precipitates, the solute concentrations of the reactant ions are dictated by solubility product relationships and supersaturation limitations. For the $Ca^{2+}-[PO_4]^{-3}$ system, these expressions are exceedingly complicated, due in large part to the numerous pathways (i.e., solid phases) for relieving the supersaturation conditions. Temperature, pH, ionic strength, ion pair formation, the presence of extraneous cations and anions all can affect the various solute species equilibria and attainable or sustainable supersaturation levels (F. Abbona, M. Franchini-Angela, and R. Boistelle, "Crystallization of calcium and magnesium phosphates from solutions of medium and low concentrations," Cryst. Res. Technol. 27: 41 (1992); G. H. Nancollas, "The involvement of calcium phosphates in biological mineralization and demineralization processes," Pure Appl. Chem. 64(11): 1673 (1992); G. H. Nancollas and J. Zhang, "Formation and dissolution mechanisms of calcium phosphates in aqueous systems," in Hydroxyapatite and Related Materials, pp 73–81 (1994), CRC Press, Inc.; P. W. Brown, N. Hocker, and S. Hoyle, "Variations in solution chemistry during the low temperature formation of hydroxyapatite," J. Am. Ceram. Soc. 74(8): 1848 (1991); G. Vereecke and J. Lemaitre, "Calculation of the solubility diagrams in the system $Ca(OH)_2$—$H_3PO_4$—$KOH$—$HNO_3$—$CO_2$—$H_2O$," J. Cryst. Growth 104: 820 (1990); A. T. C. Wong and J. T. Czernuszka, "Prediction of precipitation and transformation behavior of calcium phosphate in aqueous media," in Hydroxyapatite and Related Materials, pp 189–196 (1994), CRC Press, Inc.; G. H. Nancollas, "In vitro studies of calcium phosphate crystallization," in Biomineralization—Chemical and Biochemical Perspectives, pp 157–187 (1989)).

Additionally, while thermodynamics will determine whether a particular reaction is possible, kinetic effects may be very much more important in explaining the absence or presence of particular calcium phosphate phases during precipitation reactions.

In the practice of certain preferred embodiments of this invention to give rise to calcium phosphates, soluble calcium ion is maintained at concentrations of several molar in the presence of soluble hypophosphite anion which is, itself, also at high molar concentrations. The solution is also at a very low pH due to the presence of nitric and hypophosphorous acids. Indeed, such solutions of calcium and hypophosphite ions can be stable indefinitely with respect to precipitation, at room temperature or below. In contrast, it is impossible (in the absence of ion complexation or chelating agents) to simultaneously maintain calcium ions and phosphate anions at similar concentrations as a solid phase would immediately precipitate to relieve the supersaturation. Upon oxidation of the hypophosphite ion to phosphite and, subsequently, to phosphate, calcium phosphate phases are rapidly precipitated from homogeneous solution under solution conditions unique (concentration, pH, ionic strength) for the formation of such materials. The combination of homogeneous generation of precipitating anion, rapid precipitation kinetics, and unique thermodynamic regime results in the formation of calcium phosphate precursors having unique size and morphological characteristics, surface properties, and reactivities.

The foregoing consideration will also apply to minerals other than the calcium phosphates. Perforce, however, the phase diagrams, equilibrium conditions and constituent mineral phases will differ in each family of minerals.

Uniformly sized and shaped particles of metal salts comprised of one or more metal cations in combination with one or more oxoacid anions can result from the present general method for the controlled precipitation of said metal salts from aqueous solutions. These proceed via the in situ homogeneous production of simple or complex oxoacid anions of one or more of the nonmetallic elements, Group 5B and 6B (chalcogenides), and 7B (halides). The first oxoacid anion undergoes oxidation (increase in chemical oxidation state) to generate the precipitant anionic species along with concurrent reduction (decrease in chemical oxidation state) of the nonmetallic element of a second, dissimilar oxoacid anion, all oxoacid anions initially being present in solution with one or more metal cations known to form insoluble salts with the precipitant anion. The metal cations are, preferably, oxidatively stable, but may undergo oxidation state changes themselves under certain conditions.

RPR is induced preferably by heating a homogeneous solution, so as to promote the onset and continuation of an exothermic redox reaction. This exothermic reaction results in the generation of gases, usually various nitrogen oxide gases such as $NO_x$, where $0.5<x<2$, as the soluble reduced phosphorus species are converted to precipitating anions which then homogeneously precipitate the calcium ions from the reaction medium. At this stage, the reaction is substantially complete, resulting in an assemblage of ultrafine precipitated particles of the predetermined calcium-phosphate stoichiometry. The reaction yield is high as is the purity of the reaction products.

The use of alternate heating methods to initiate and complete the RPR reaction may offer utility in the formation of scaffold structures. One such power source is microwave energy, as found in conventional 600–1400 W home microwave ovens. The benefit of the use of microwaves is the uniformity of the heating throughout the entire reaction mass and volume as opposed to the external-to-internal, thermal gradient created from traditional conduction/convection/radiant heating means. The rapid, internal, uniform heating condition created by the use of microwave energy provides for rapid redox reaction initiation and drying. The excess RPR liquid is expelled to the outer surface of the cellulose body and flashes off to form an easily removed deposit on the surface. The rapid rate of heating and complete removal of the fugitive substructure alters the particulate structure resulting in greater integral strength. The speed of heating and initiation of the RPR reaction may also minimize crystal grain growth.

Figure 2:
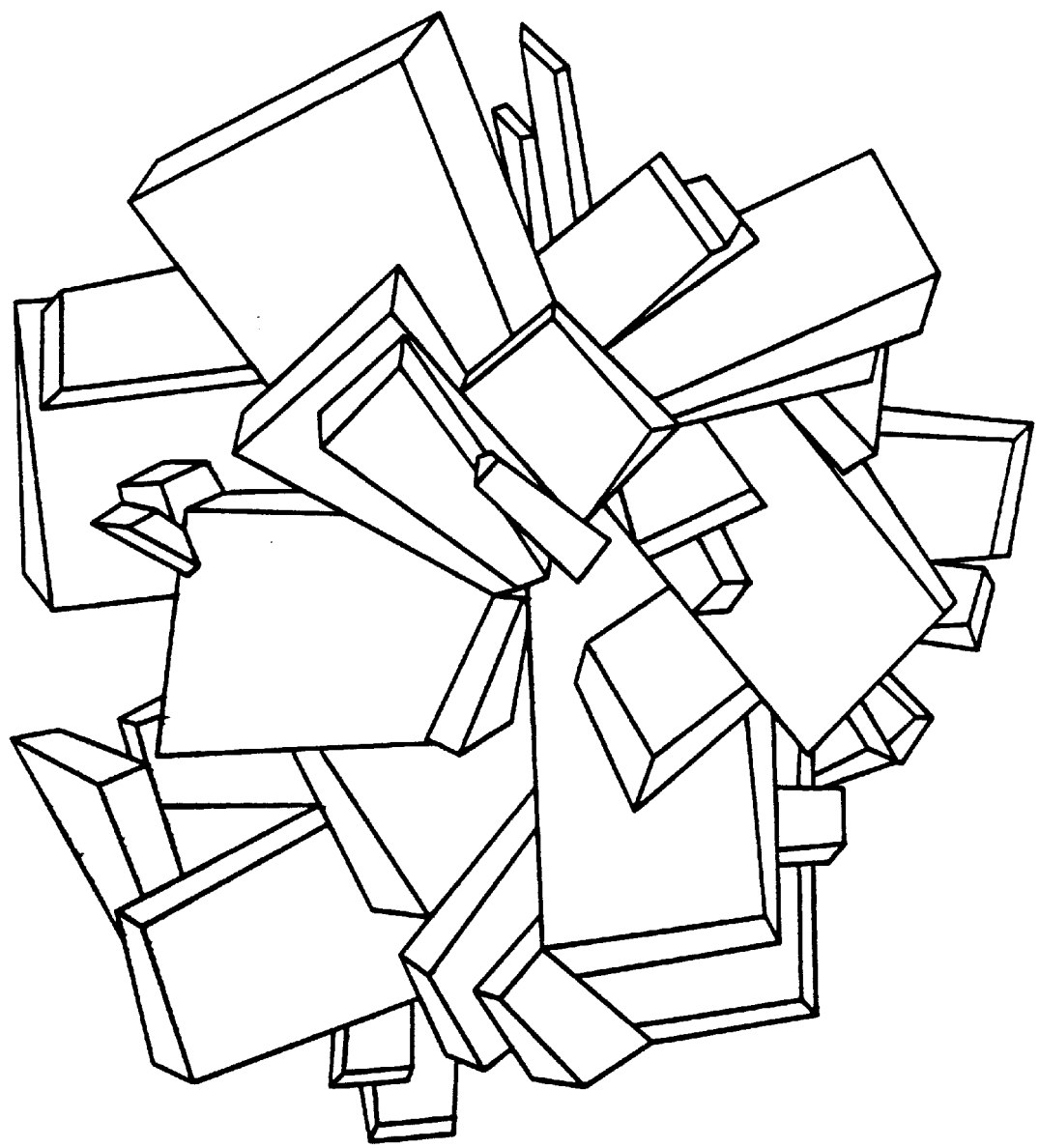
FIG. 2 represents assembled monetite, CaHPO$_4$ particles formed from a hydrothermal precipitation in accordance with certain methods taught by this invention. The entire particle assemblage is typically about 30 μm and is comprised of relatively uniformly rectangular cubes and plate-like crystallites of various sizes and aspect ratios.

Intermediate precursor mineral powders are homogeneously precipitated from solution. Moderate heat treatments at temperatures <500° C., can be used to further the transformation to various phosphate containing phases. Proper manipulations of chemistry and process conditions have led to mono- and multiphasic compounds with unique crystal morphologies, see, e.g. FIGS. 1 and 2.

The nitrate/hypophosphite redox system involves a hypophosphite oxidation to phosphate ($P^{+1}$ to $P^{+5}$, a $4e^-$ oxidation) as depicted in the following equations ($E_o$/V from N. N. Greenwood and A. Earnshaw, "Oxoacids of phosphorus and their salts," in Chemistry of the Elements, pp 586–595 (1984), Pergamon Press):

| Reaction | Reduction potential at pH 0, 25° C. $E_o$/V | | |
|---|---|---|---|
| $H_3PO_3 + 2H^+ + 2e^- = H_3PO_2 + H_2O$ | −0.499 | | (1) |
| $H_3PO_4 + 2H^+ + 2e^- = H_3PO_3 + H_2O$ | −0.276 | | (2) |
| $H_3PO_4 + 4H^+ + 4e^- = H_3PO_2 + H_2O$ | −0.775 | Overall | (3) | and a nitrate reduction to $NO_x$ ($N^{+5}$ to $N^{+3}$ or $N^{+2}$, either a $2e^-$ or a $3e^-$ reduction) as depicted in the following equations:

| Reaction | Reduction potential at pH 0, 25° C. $E_O/V$ | |
|---|---|---|
| $2ON_3^- + 4H^+ + 2e^- = N_2O_4 + 2H_2O$ | 0.803 | (4) |
| $NO_3^- + 3H^+ + 2e^- = HNO_2 + H_2O$ | 0.94 | (5) |
| $NO_3 + 4H^+ + 3e^- = NO + 2H_2O$ | 0.957 | (6) |

Chemical reactions are conveniently expressed as the sum of two (or more) electrochemical half-reactions in which electrons are transferred from one chemical species to another. According to electrochemical convention, the overall reaction is represented as an equilibrium in which the forward reaction is stated as a reduction (addition of electrons), i.e.:

Oxidized species+ne⁻=Reduced species

For the indicated equations at pH=0 and 25° C., the reaction is spontaneous from left to right if $E_o$ (the reduction potential) is greater than 0, and spontaneous in the reverse direction if $E_o$ is less than 0.

From the above reactions and associated electrochemical potentials, it is apparent that nitrate is a strong oxidant capable of oxidizing hypophosphite ($p^{+1}$) to phosphite ($P^{+3}$) or to phosphate ($P^{+5}$) regardless of the reduction reaction pathway, i.e., whether the reduction process occurs according to Equation 4, 5, or 6. If an overall reaction pathway is assumed to involve a combination of oxidation reaction (Eq.3) (4e⁻ exchange) and reduction reaction (Eq.6) (3e⁻ exchange), one can calculate that in order for the redox reaction to proceed to completion, 4/3 mole of $NO_3^-$ must be reduced to NO per mole of hypophosphite ion to provide sufficient electrons. It is obvious to one skilled in the art that other redox processes can occur involving combinations of the stated oxidation and reduction reactions.

Different pairings of oxidation and reduction reactions can be used to generate products according to the spirit of this invention. Indeed, the invention generally allows for the in situ homogeneous production of simple or complex oxoacid anions in aqueous solution in which one or more nonmetallic elements such as Group 5B and 6B (chalcogenides), and 7B (halides) comprising the first oxoacid anion undergoes oxidation to generate the precipitant anionic species along with concurrent reduction of the nonmetallic element of a second, dissimilar oxoacid anion.

In each of the above scenarios, the key is the reduction-oxidation reaction at high ionic concentrations leading to the homogenous precipitation from solution of novel calcium phosphate powders. Never before in the literature has the ability to form such phases, especially calcium-phosphate phases, been reported under the conditions described in this invention.

Specific embodiments of the invention utilize the aforementioned processes to yield unique calcium phosphate precursor minerals that can be used to form a self-setting cement or paste. Once placed in the body, these calcium phosphate cements (CPC) will be resorbed and remodeled (converted) to bone. A single powder consisting of biphasic minerals of varying Ca/P ratio can be mixed to yield self-setting pastes that convert to type-B carbonated apatite (bone mineral precursor) in vivo.

The remodeling behavior of a calcium phosphate bioceramic to bone is dictated by the energetics of the surface of the ceramic and the resultant interactions with osteoclastic cells on approach to the interface. Unique microstructures can yield accelerated reactivity and, ultimately, faster remodeling in vivo. The compositional flexibility in the fine particles of this invention offers adjustable reactivity in vivo. The crystallite size and surface properties of the resultant embodiments of this invention are more similar to the scale expected and familiar to the cells found in the body. Mixtures of powders derived from the processes of this invention have tremendous utility as calcium phosphate cements (CPCs).

An aqueous solution can be prepared in accordance with the present invention and can be imbibed into a sacrificial organic substrate of desired shape and porosity, such as a cellulose sponge. The solution-soaked substrate is subjected to controlled temperature conditions to initiate the redox precipitation reaction. After the redox precipitation reaction is complete, a subsequent heating step is employed to combust any remaining organic material and/or promote phase changes. The resultant product is a porous, inorganic material which mimics the shape, porosity and other aspects of the morphology of the organic substrate.

Figure 3:
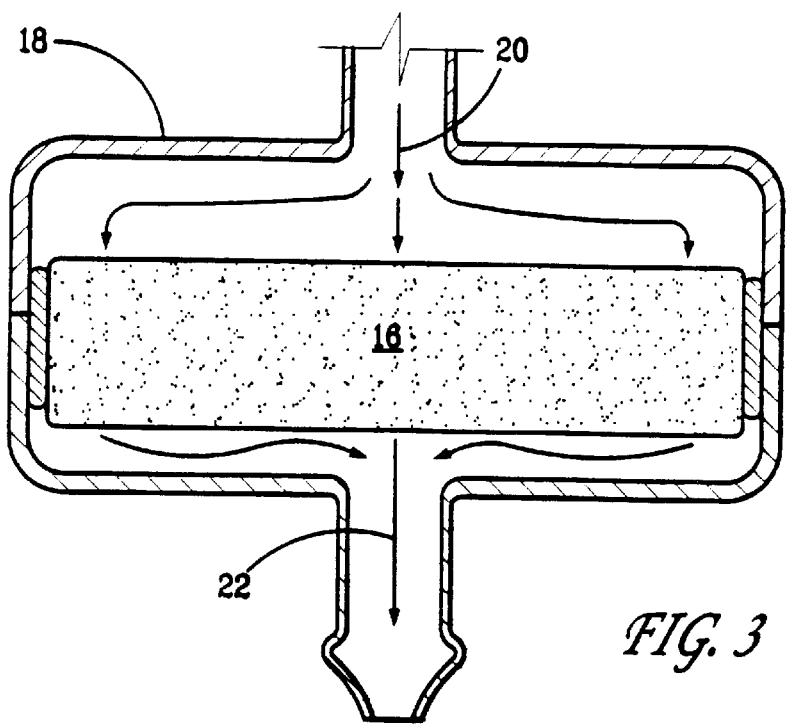
FIG. 3 illustrates a water purification disk that is comprised of the porous inorganic material of the present invention and is contained within an exterior housing for filtration or separation purposes.

It is anticipated that the porous inorganic materials of the present invention would be suitable for a variety of applications. FIG. 3 depicts a discoidal filter scaffold 16, which is prepared in accordance with the present invention, and enclosed within an exterior filter housing 18 for filtration or bioseparation applications. Depending upon its end use, discoidal filter scaffold 16 can be a biologically active, impregnated porous scaffold. Arrow 20 represents the inlet flow stream. Arrow 22 represents the process outlet stream after passing through discoidal filter scaffold 16.

Figure 4:
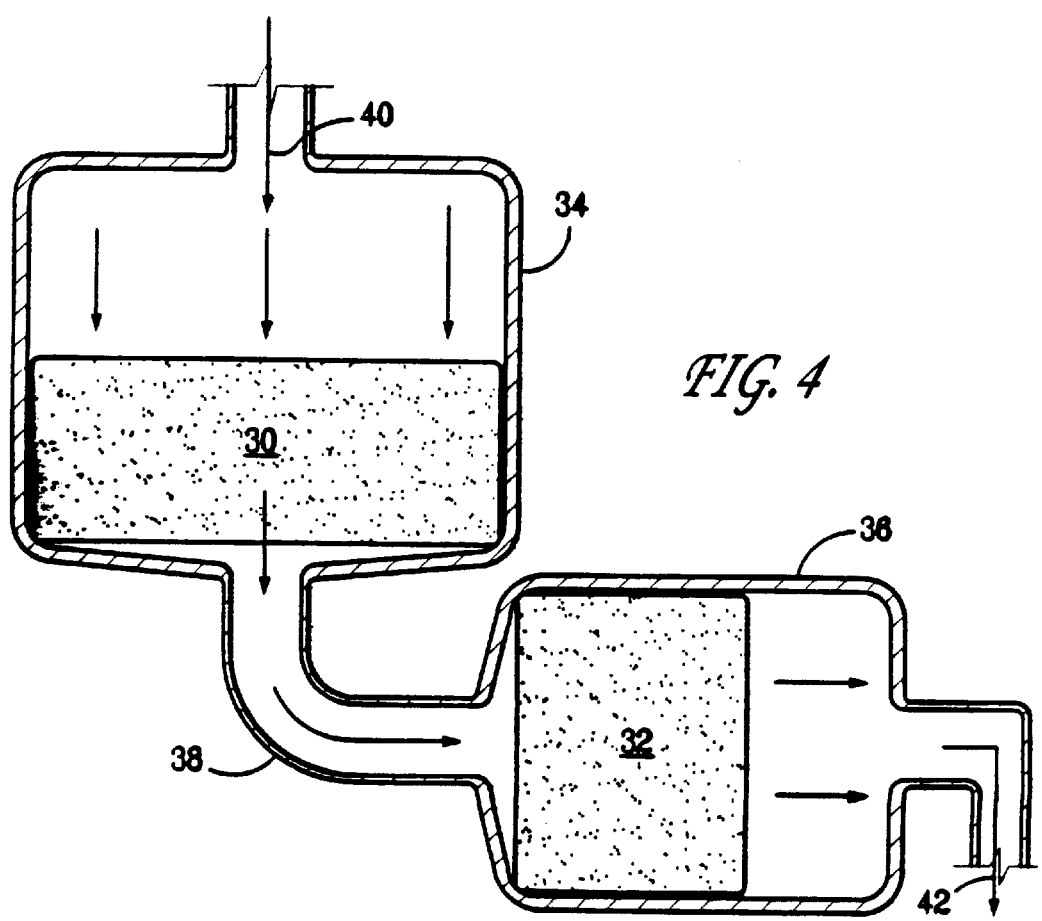
FIG. 4 illustrates shaped bodies of porous inorganic material of the present invention used as a catalyst support within a hot gas reactor or diffusor.

FIG. 4 illustrates a block of the porous inorganic material that is used as a catalyst support within a two stage, three way hot gas reactor or diffusor. Items 30 and 32 illustrate blocks of the porous material used as catalytically impregnated scaffolds. Items 30 and 32 may be composed of the same or different material. Both 30 and 32, however, are prepared in accordance with an embodiment of the present invention. Item 34 depicts the first stage catalyst housing, which may be comprised of a ferrous-containing material, and encloses item 30. Item 36 depicts the second stage catalyst housing, which may be comprised of a ferrous-containing material, and encloses item 32. Item 38 represents the connector pipe, which is comprised of the same material as the housings 34 and 36, and connects both 34 and 36. Arrow 40 represents the raw gas inlet stream prior to passing through both blocks of catalytically impregnated scaffold (items 30 and 32). Arrow 42, lastly, represents the processed exhaust gas stream.

Figure 5:
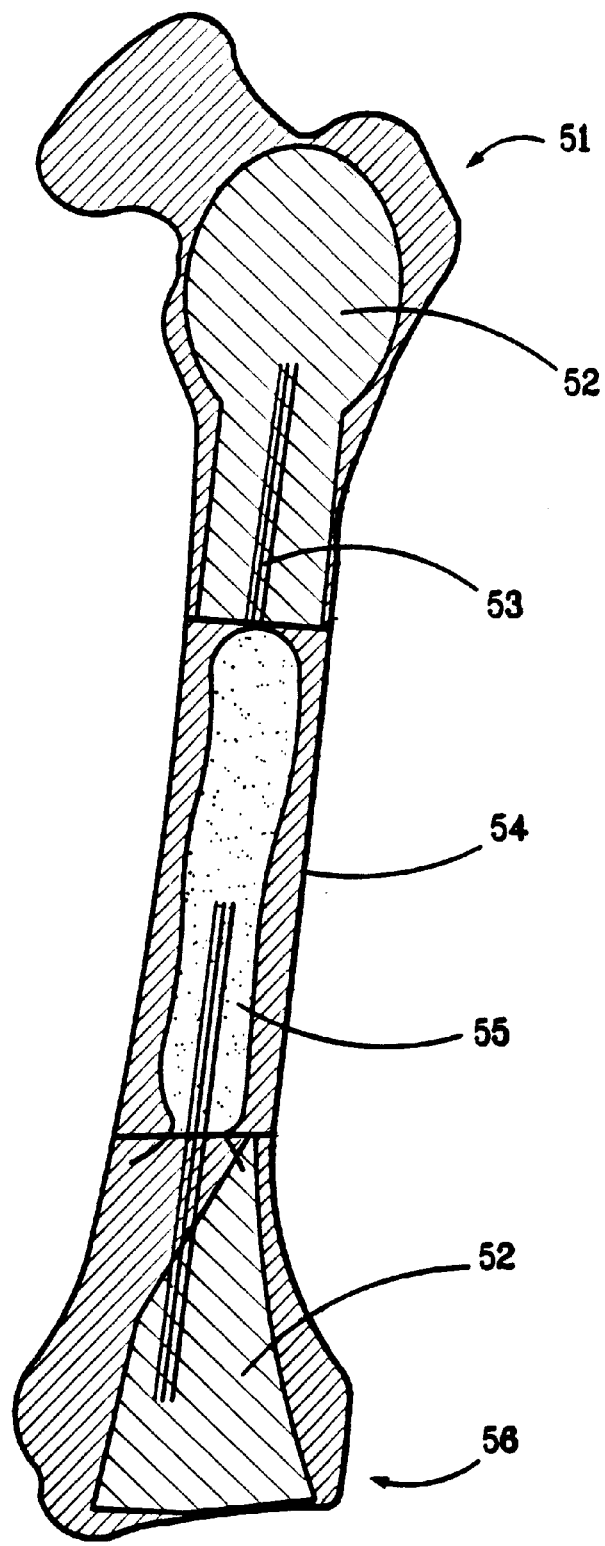
FIG. 5 illustrates shaped bodies of porous calcium phosphate material of the present invention implanted at several sites within a human femur for cell seeding, drug delivery, protein adsorption, or growth factor scaffolding purposes.

In other embodiments of the present invention, the inorganic porous material is a calcium phosphate scaffolding material that may be employed for a variety of uses. FIG. 5 illustrates a block of the calcium phosphate scaffolding material 55 that may be inserted into a human femur and used for cell seeding, drug delivery, protein adsorption, growth factor introduction or other biomedical applications. Femoral bone 51 is comprised of metaphysis 52, Haversian canal 53, diaphysis 54 and cortical bone 56. The calcium phosphate scaffolding material 55 is inserted into an excavation of the femoral bone as shown and ties into the Haversian canal allowing cell seeding, drug delivery, or other applications. Scaffolding material 55 can be used in the same manner in a variety of human or mammalian bones.

Figure 6A:
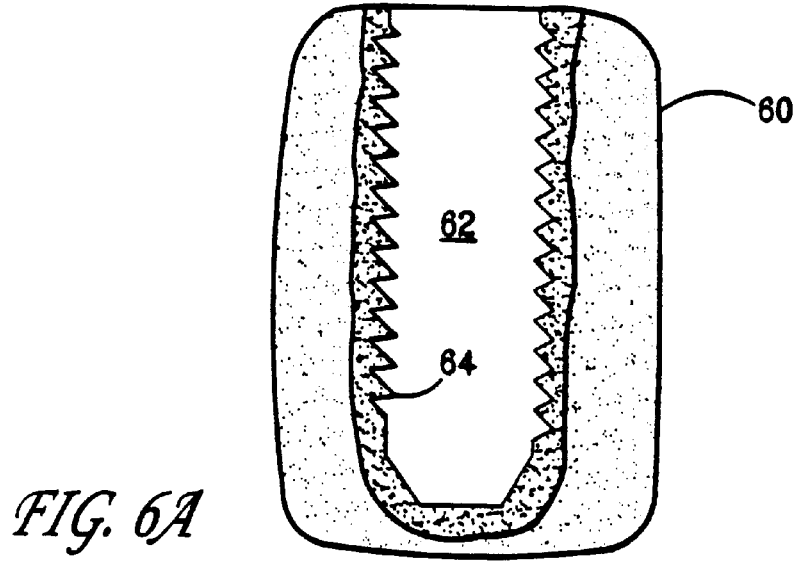
FIG. 6A and FIG. 6B illustrate one embodiment of porous calcium phosphate scaffolding material of the present invention used as an accommodating sleeve in which a tooth is screwed, bonded, cemented, pinned, anchored, or otherwise attached in place.
Figure 6B:
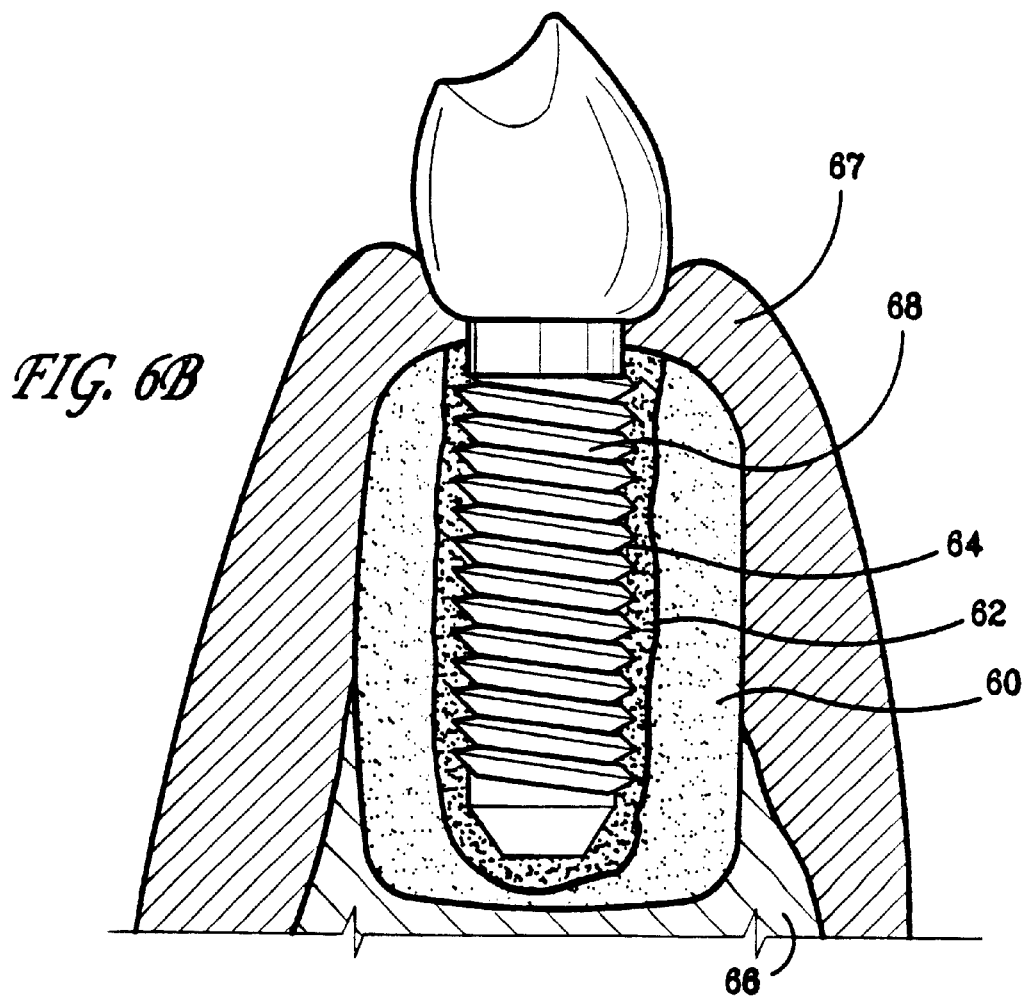

FIG. 6A shows the calcium phosphate material of the present invention formed into the shape of a calcium phosphate sleeve 60. Item 62 depicts the excavated cavity which can be formed via machining or other means. Item 64 presents a plurality of threads which can be coated with bioactive bone cement. FIG. 6B shows the calcium phosphate sleeve 60 inserted into the jaw bone 66 and gum 67. The calcium phosphate sleeve 60 may be fixed in place via pins, bone cement, or other mechanical means of adhesion. An artificial tooth or dental implant 68 can then be screwed into sleeve 60 by engaging threads 64.

Figure 7B:
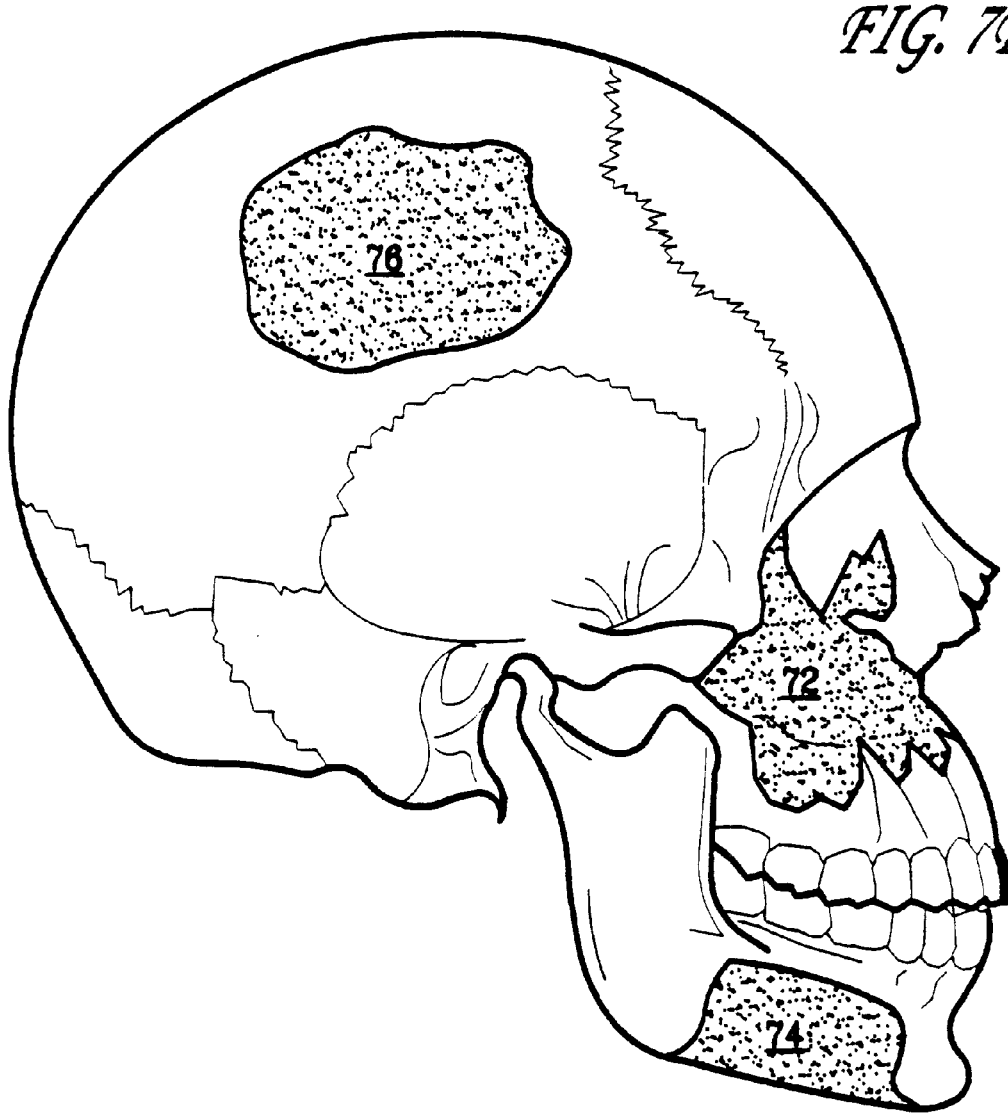
FIGS. 7 and 7A illustrate another embodiment of the porous calcium phosphate scaffolding material of the present invention used as a cranio-maxillofacial, zygomatic reconstruction and mandibular implant.
Figure 7A:
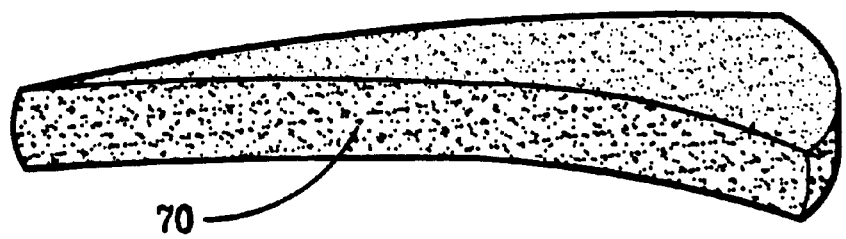

FIG. 7A shows the porous, calcium phosphate scaffolding material 70, prepared in accordance with an embodiment of the present invention, which is machined or molded to patient specific dimensions. FIG. 7B depicts the use of the material 70 that is formed into the shape of craniomaxillofacial implant 76, a zygomatic reconstruction 72, or a mandibular implant 74.

Figure 8A:
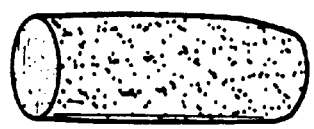
FIGS. 8A and 8B illustrate one embodiment of the porous calcium phosphate scaffolding material of the present invention shaped into a block form and used as a tibial plateau reconstruction that is screwed, bonded, cemented, pinned, anchored, or otherwise attached in place.
Figure 8B:
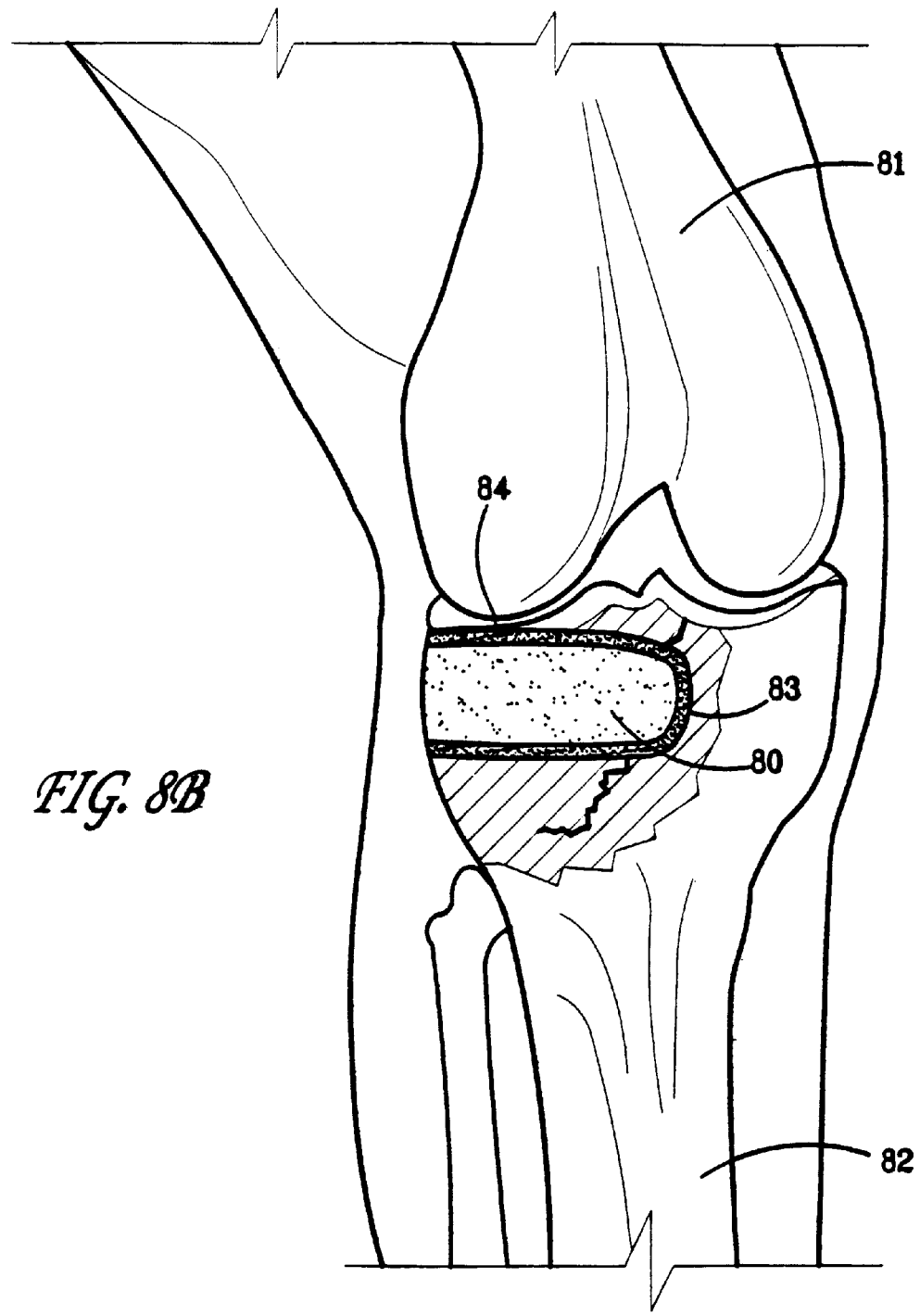

FIG. 8A depicts a plug of the porous, calcium phosphate scaffolding material 80. FIG. 8B illustrates plug 80 which is inserted into an excavation site 83 within a human knee, below the femur 81 and above the tibia 82, for use in a tibial plateau reconstruction. Plug 80 is held in place or stabilized via a bone cement layer 84.

Figure 9:
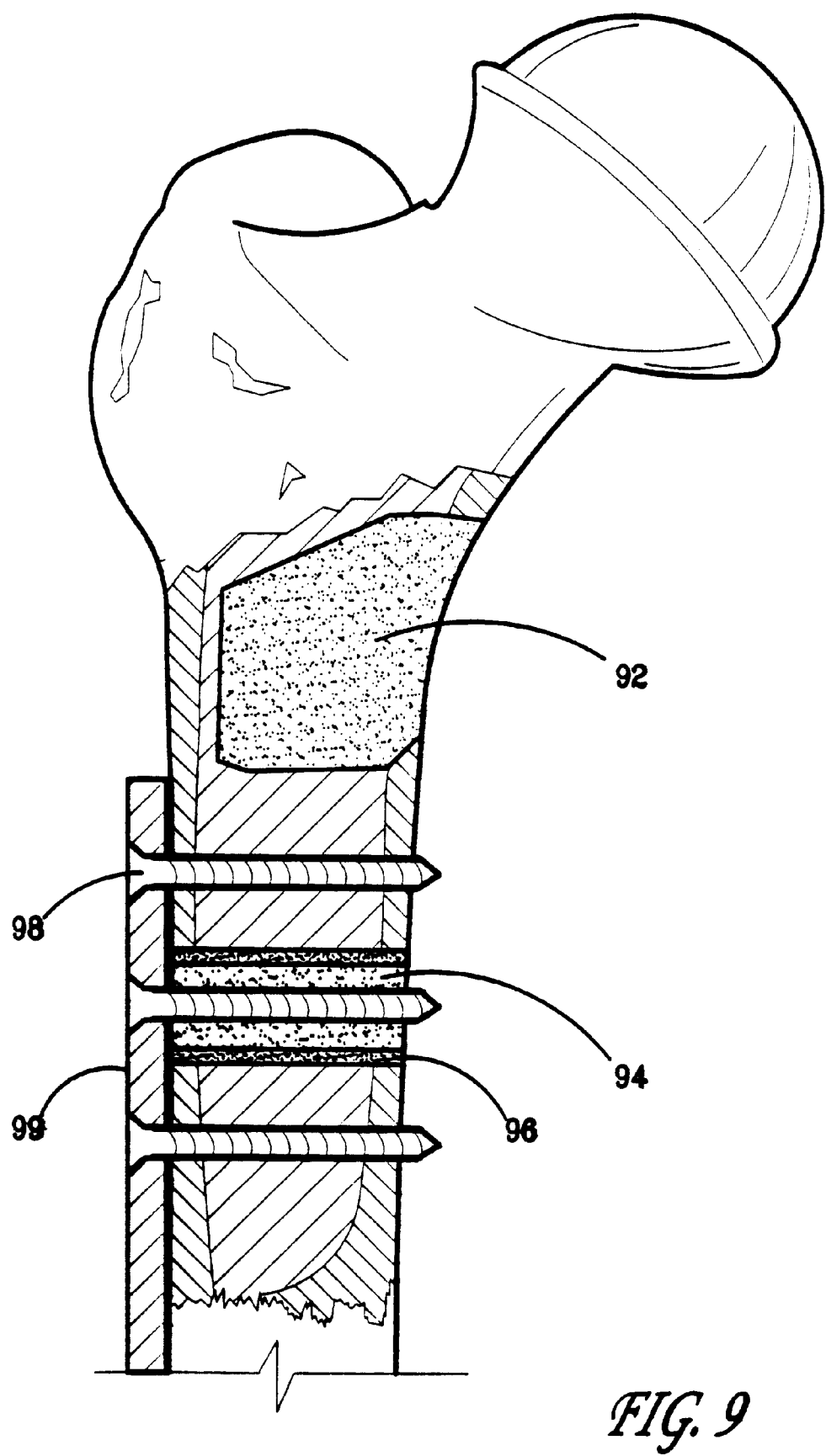
FIG. 9 illustrates an embodiment of the porous calcium phosphate scaffolding material of the present invention shaped into a block or sleeve form and used for the repair or replacement of bulk defects in metaphyseal bone, oncology defects or screw augmentation.

FIG. 9 shows the calcium phosphate scaffolding material within a human femur that is used as a block 92 for bulk restoration or repair of bulk defects in metaphyseal bone or oncology defects, or as a sleeve 94 for an orthopaedic screw, rod or pin 98 augmentation. Item 99 depicts an orthopaedic plate anchored by the orthopaedic device item 98. Bone cement layer 96 surrounds and supports sleeve 94 in place.

Figure 10B:
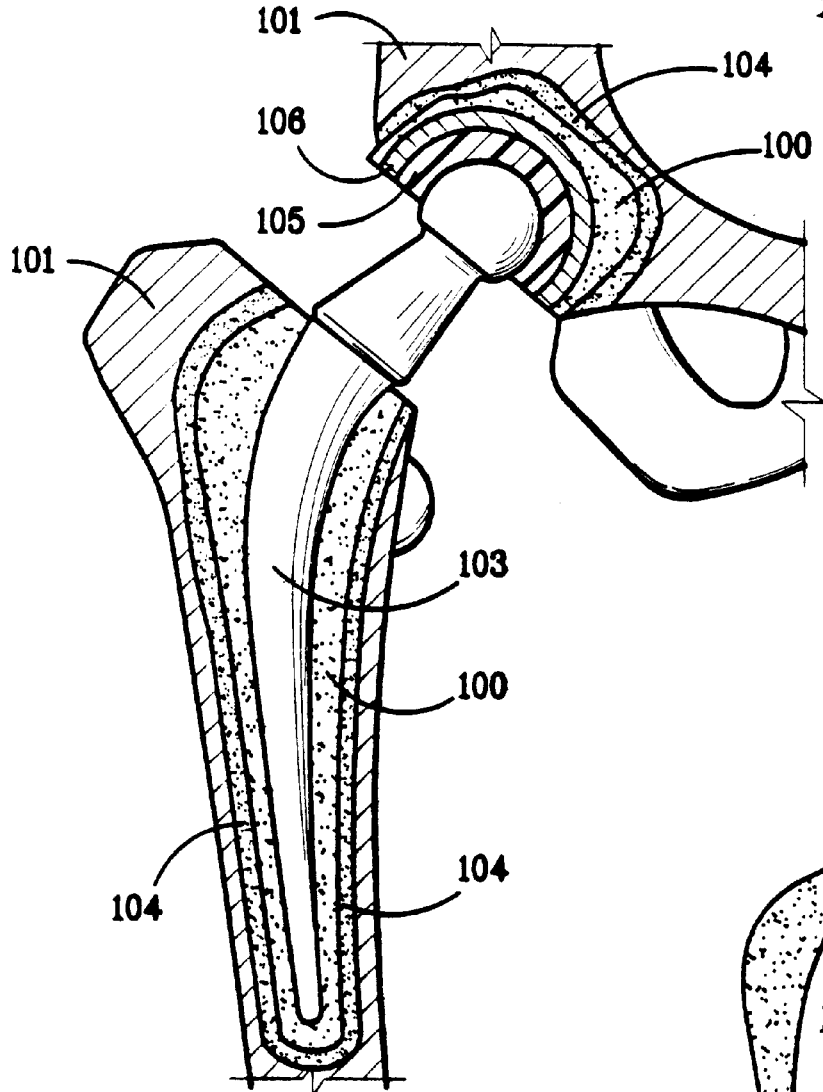
FIGS. 10A and 10B illustrate an embodiment of the porous calcium phosphate scaffolding material of the present invention shaped into a sleeve form and used for impaction grafting to accommodate an artificial implant said sleeve form being screwed, bonded, pinned or otherwise attached in place.
Figure 10A:
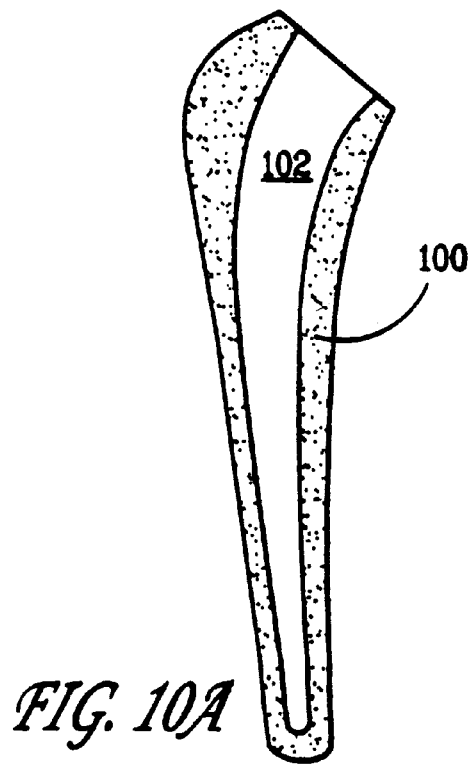

Lastly, FIGS. 10A and 10B depict the use of the calcium phosphate scaffolding material as a receptacle sleeve 100 that is inserted into the body to facilitate a bipolar hip replacement. Cavity 102 is machined to accommodate the insertion of a metallic ball joint implant or prosthesis 103. An orthopaedic surgeon drills a cavity or furrow into the bone 101 to receive sleeve 100. Sleeve 100 is then affixed to the surrounding bone via a bioactive or biocompatible bone cement layer 104 or other means. On the acetabular side, a femoral head articulation surface 106 is cemented to a bone cement layer 104 that resides within a prepared cavity with material of the present invention, 100. A high molecular weight polyethylene cup, 105 is used to facilitate articulation with the head of the prosthesis 103. The metallic ball joint implant or prosthesis 103 is thus inserted into a high molecular weight polyethylene cup 105 to facilitate joint movement.

Orthopaedic appliances such as joints, rods, pins, sleeves or screws for orthopaedic surgery, plates, sheets, and a number of other shapes may be formed from the calcium phosphate scaffolding material in and of itself or used in conjunction with conventional appliances that are known in the art. Such porous inorganic bodies can be bioactive and can be used, preferably, in conjunction with biocompatible gels, pastes, cements or fluids and surgical techniques that are known in the art. Thus, a screw or pin can be inserted into a broken bone in the same way that metal screws and pins are currently inserted, using conventional bone cements or restoratives in accordance with the present invention or otherwise. The bioactivity of the calcium phosphate scaffolding material will give rise to osteogenesis with beneficial medical or surgical results. For example, calcium phosphate particles and/or shaped bodies prepared in accordance with this invention can be used in any of the orthopaedic or dental procedures known for the use of calcium phosphate; the procedures of bone filling defect repair, oncological defect filling, craniomaxillofacial void filling and reconstruction, dental extraction site filling, and potential drug delivery applications.

The scaffold structures of this invention, calcium phosphate in particular, can be imbibed with blood, cells (e.g. fibroblasts, mesenchymal, stromal, marrow and stem cells), protein rich plasma other biological fluids and any combination of the above. Experiments have been conducted with ovine and canine blood (37° C.) showing the ability of the scaffold to maintain its integrity while absorbing the blood into its pores. This capability has utility in cell-seeding, drug delivery, and delivery of biologic molecules as well as in the application of bone tissue engineering, orthopaedics, and carriers of pharmaceuticals. This makes the Ca-P scaffold ideal for the use as an autograft extender or replacement graft material.

The scaffold structures, especially calcium phosphate, can be imbibed with any bioabsorbable polymer or film-forming agent such as polycaprolactones (PCL), polyglycolic acid (PGA), poly-L-Lactic acid (PL-LA), polysulfones, polyolefins, polyvinyl alcohol (PVA), polyalkenoics, polyacrylic acids (PAA), polyesters and the like. Experiments have been conducted with PCL, by solubilizing the PCL in an evaporative solvent and saturating a plug of calcium phosphate scaffold structure, allowing the structure to dry, and thus fixing the PCL onto the surface and throughout the body of the scaffold. The resultant mass is strong, carveable, and somewhat compressible. Experiments showed that the PCL coated material still absorbs blood.

Numerous other uses for these minerals and shaped bodies comprised thereof are anticipated. The oxidizing agents, reducing agents, ratios, co-reactants and other adducts, products and exemplary uses will be understood by inorganic chemists from a review of the aforementioned chemical reactions. Calcium phosphates are indicated for biological restorations, dental restorations, bioseparations media, and ion or protein chromatography. Transition metal phosphates (Sc, Ti, V, Cr, Mn, Fe, Co, Ni, Cu, and Zn) and shaped, porous articles thereof have numerous potential uses as pigments, phosphors, catalysts, electromagnetic couplers, microwave couplers, inductive elements, zeolites, glasses, nuclear waste containment systems, radomes and coatings. Addition of rare-earths phosphates can lead to uses as intercalation compounds, catalysts, catalyst support material, glasses and ceramics, radiopharmaceuticals, pigments and phosphors, medical imaging agents, nuclear waste solidification, electro-optics, electronic ceramics, and surface modifications.

Aluminum and zirconium phosphates and shaped, porous articles thereof are ideal candidates for surface protective coatings, abrasive particles, polishing agents, cements, and filtration products in either granular form or as coatings. The alkali (Na, K, Rb, Cs) and alkaline-earth (Be, Mg, Ca, Sr, Ba) phosphates and shaped, porous articles thereof would generate ideal low temperature glasses, ceramics, biomaterials, cements, glass to metal seals, and other numerous glass-ceramic materials, such as porcelains, dental glasses, electro-optic glasses, laser glasses, specific refractive index glasses and optical filters. It is to be understood that the diverse chemistries set forth herein may be applied to the creation of shaped bodies of the invention.

It will be appreciated that, in accordance with certain embodiments of this invention, RPR-derived materials will be caused to exist on or in a first solid portion of material. The resulting composite structures offer highly desirable properties and are useful for a very wide range of applications. The RPR-derived portions of the composite shaped bodies of the invention form one portion of those bodies. The other portion of the shaped bodies is comprised of another, solid material. The materials which can make up the non-RPR-derived portion or portions of the shaped bodies can be any of a wide variety of compositions which are consistent with the overall objects of this invention. Thus, such materials may be metal, such as stainless steel, titanium, amalgam, silver, gold and the like. Metals stable to the human body are preferred although for non-surgical uses others can be employed as well. These materials may be ceramic or glass. In this context, bioactive glasses and ceramics are preferred. 45S5 glass materials are osteostimulatory and osteogenetic and can be used profitably in certain restorations. Many ceramics are biostable, strong and well suited to use in this invention. Plastic materials may be the most flexible, however and will be preferred in many applications. In any event, any solid material can form the non-RPR-derived portion or portions of the shaped bodies of the invention so long as they are stable to the intended use and to the RPR-derived material and can be formed or adhered therewith.

Of the polymers, the acrylics are preferred. Chief among this class for use with the present invention are acrylic polymers including inorganic fillers. Any of this class, which is known per se, may be used. The preferred material is known as Orthocomp™ sold by Orthovita Corporation of Malvern, Pennsylvania. Orthocomp™ is an acrylic having inorganic filler. As part of the inorganic filler, the mineral Combeite is included. This filler system has been found to be biostable and bioactive. U.S. Pat. Nos. 5,681,872 and 5,914,356, assigned to the assignee of this invention, are directed to materials of this class and are incorporated herein by reference as if set forth in full. These polymers are easily worked with, are hard, strong and bioactive.

It will be appreciated that during formation, RPR-derived materials may, indeed, be formed in conjunction with another solid material, e.g. sponge, glass or metal surfaces and the like. In general, the RPR material is removed from such solid material prior to further employment. Thus, the sponge can be pyrolyzed, the RPR material removed from metal or glass plates after formation and the like. The solid materials used in this fashion are used to facilitate formation of the RPR material. While, in some cases, direct formation of RPR material in contact with a solid portion of dissimilar material may be performed in connection with this invention, solid materials, such as spongiform materials, used solely for formation of RPR, which materials are removed prior to final fabrication or use, are not the kind of solid materials contemplated hereby. Thus, the solid materials upon which the RPR-derived materials are to be found exclude solid materials which are merely transitory.

The composite shaped bodies of the invention may be prepared in any convenient way. Thus a shape of RPR-derived material may be sprayed, dipped, brushed or otherwise coated with a polymerizable material, especially the Orthocomp™ material, and the same caused to polymerize. Alternatively, the RPR material may be formed around a core or layer of other material such a polymer, metal, etc. A further option is for a polymeric, metallic ceramic or other shape to be prepared and filled with RPR-derived material. Since the RPR-derived material does not require the application of high temperatures, this procedure is easily applicable to a host of embodiments.

Figure 45:
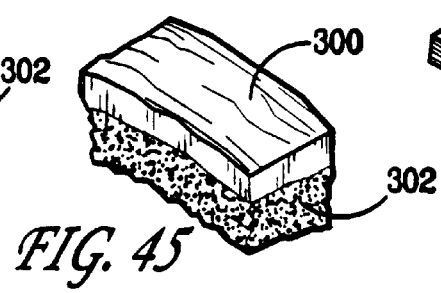
FIG. 45 depicts a cortico-cancellous "crouton" for orthopaedic surgery.

Complex structures can be made. Thus, shaped bodies having three, four and more portions are useful for some embodiments of the invention. For example, a metal strut may be surrounded by RPR-derived calcium phosphate and the whole coated with Orthocomp™ or other polymer. The resulting shaped body may be used in orthopaedic and other applications. Sandwich constructs like the "crouton" showed in FIG. 45 are also easily prepared. Persons of skill in the art will have no difficulty in preparing shaped bodies with the composite nature of the present invention.

Figure 29:
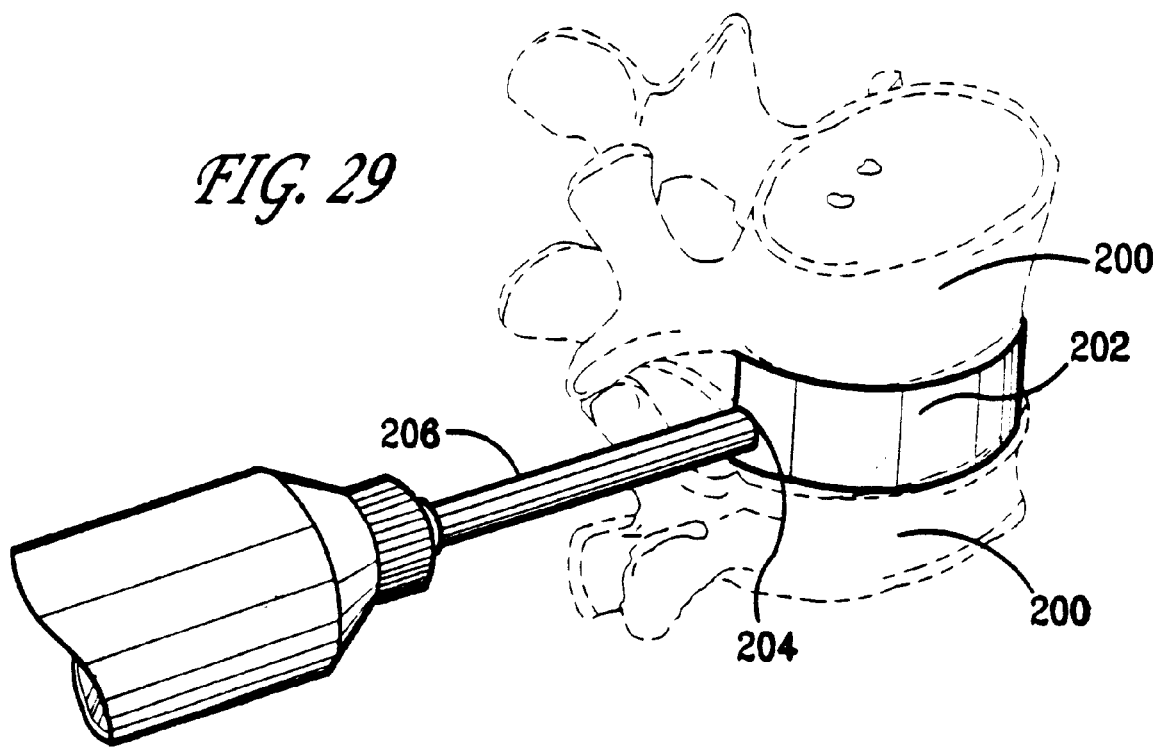
FIG. 29 depicts a synthetic cortical vertebral ring inserted between a pair of vertebrae in a spine. The injection of hardenable material, such as bone cement, into a port in the cortical ring is shown.

Exemplary composite shaped bodies are shown in the drawings. FIG. 29 depicts a pair of vertebrae 200 in a spine having a synthetic cortical ring 202 inserted therebetween. The vertebral ring has one or more access ports 204 present an in communication with the interior of the ring. Injection of hardenable material via a syringe device 206 can be accomplished via the port or ports. The hardenable material may be organic, inorganic or mixed and is generally a bone cement or polymeric bonding material.

Figure 30:
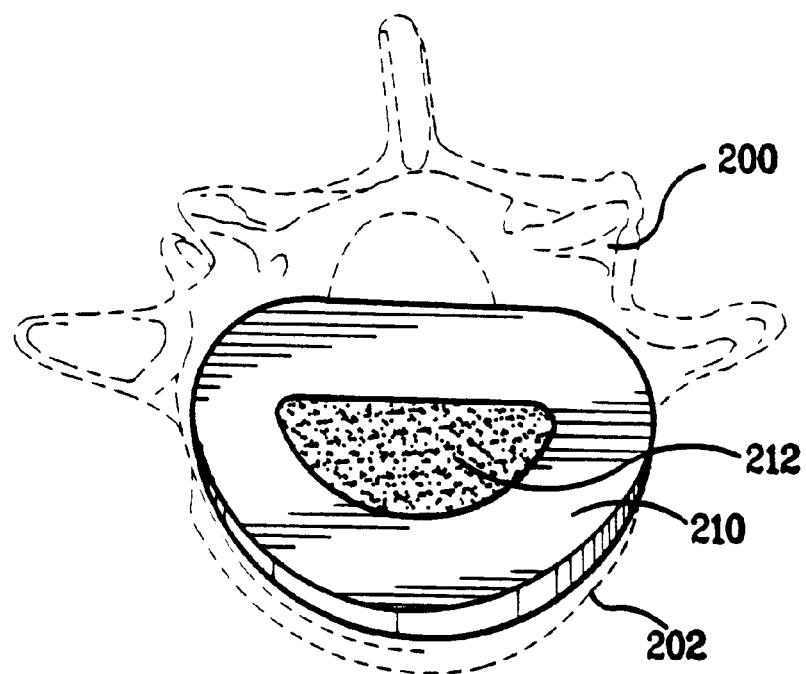
FIG. 30 is a lateral view of a synthetic cortico-cancellous vertebral ring or interbody fusion device. The composite nature of the device is shown to comprise first and second portions comprising different materials.
Figure 31:
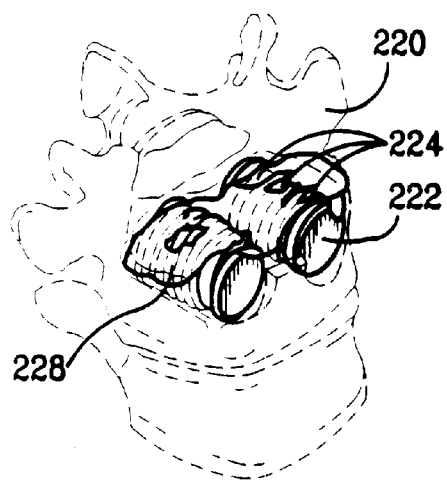
FIGS. 31 through 34 all depict spinal surgical applications with vertebrae depicted in phantom, 220.
Figure 32:
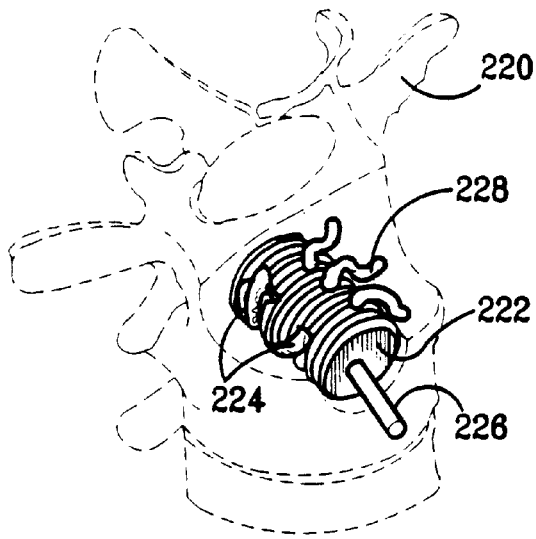

FIG. 30 is a lateral view of a synthetic cortico-cancellous vertebral ring or interbody fusion device 202. In this embodiment, the ring is composite, having a first portion 210 comprised of a first material and a second portion 212 comprised of a second material. The material of the internal portion 212 is preferably RPR derived porous, inorganic calcium phosphate. FIG. 31 shows one embodiment of a synthetic cortical bone dowel in place. The dowel has a plurality of ports, some of which are shown 224. Hardenable material such as bone cement is injected into the dowel, emerging from the ports to form a partial surround of the dowel 228. FIG. 32 depicts another bone dowel for spinal fusion. The end of an injection device or syringe 226 is shown. Bone cement 224 is shown as well emerging from access ports 228 in the dowel.

Figure 33:
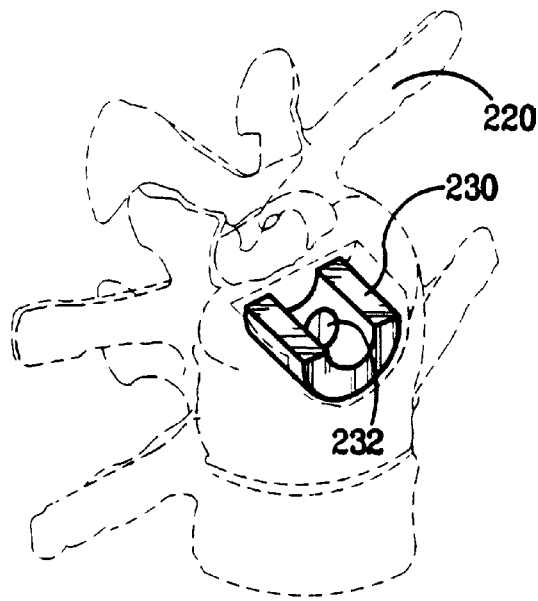
Figure 34:
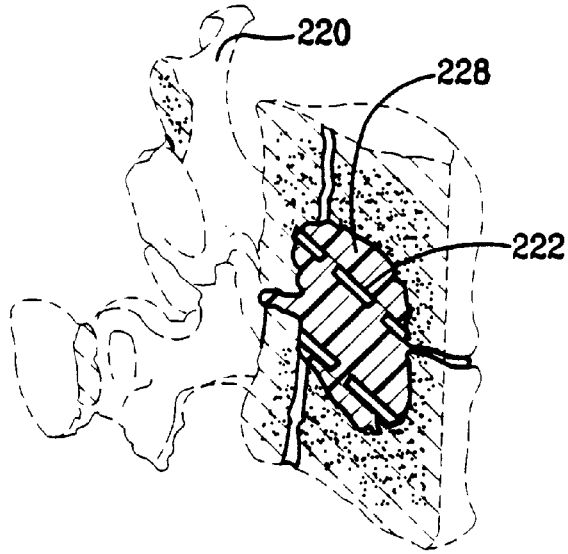

FIG. 33 shows a synthetic cortical interbody vertebral defect filling form. It, too may be employed with bone cement or otherwise. FIG. 34 is a cross sectional view of a bone dowel in place to accomplish spinal fusion. The dowel itself, 222, is shown potted within hardenable material 228 injected around and/or through the dowel.

Figure 35A:
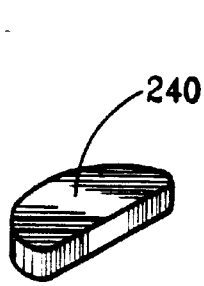
FIGS. 35a, 35b and 35c depict synthetic cortical vertebral spacers or interbody devices.
Figure 35B:
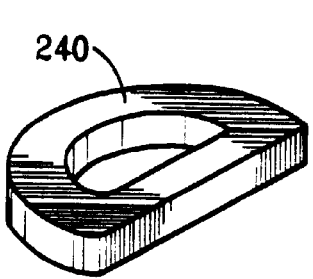
Figure 35C:
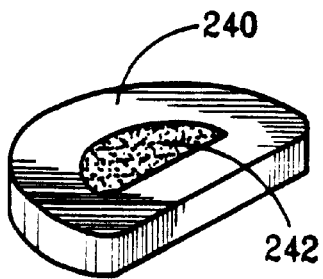

FIGS. 35a through c depict synthetic cortical vertebral spacers or interbody devices. Hard material, 240 preferably composite material in accordance with the invention, forms the spacers and rings. In preferred embodiments a plurality of regions form a composite shaped body as illustrated in FIG. 35c. Hard material such as filled acrylic polymer 240 forms an outer portion of the ring, while porous RPR-derived material, especially a calcium phosphate 242 forms an inner portion of the body.

Figure 36A:
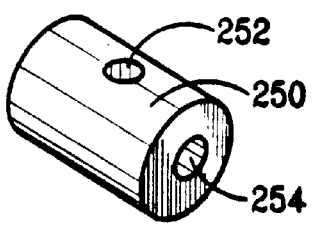
FIGS. 36a through c depict synthetic cortical bone dowels or interbody devices.
Figure 36B:
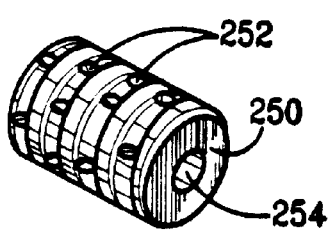
Figure 36C:
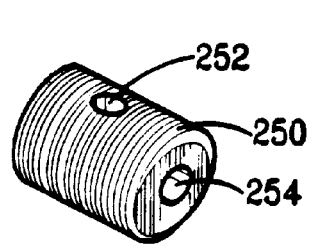
Figure 37:
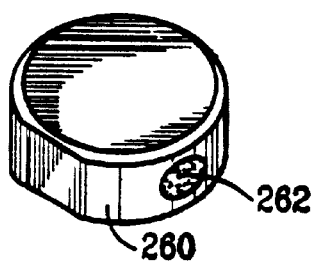
FIG. 37 is another form of cortical spacer.
Figure 38:
FIG. 38 is of a synthetic cancellous bone dowel.

FIGS. 36a through c depict synthetic cortical bone dowels or interbody devices 250. The dowels may have access ports 252 for emergence of hardenable material when such material is injected into orifice 254 with a syringe device. The dowels and devices may be composite as set forth herein. FIG. 37 is another form of cortical spacer. The spacer has a relatively hard outer portion 260 and RPR derived inner portion 262. FIG. 38 is of a synthetic cancellous bone dowel. The dowel as depicted preferably had a heterogenous core material such as a hard plastic, ceramic or metal.

Figure 39:
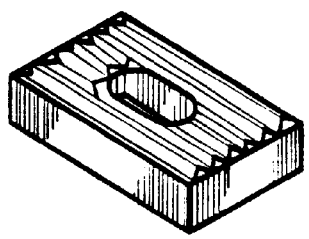
FIG. 39 is a synthetic cortical vertebral interbody device.
Figure 40A:
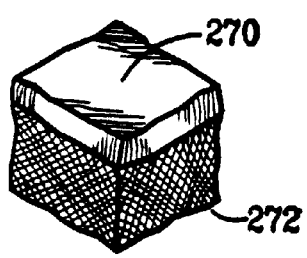
FIGS. 40a, and 40c are of synthetic cortico-cancellous defect filling forms for bone restoration.
Figure 40B:
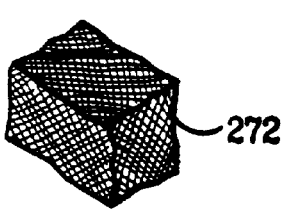
FIG. 40b shows a cancellous defect filling form.
Figure 40C:
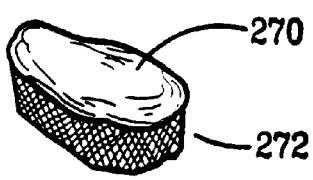
Figure 41A:
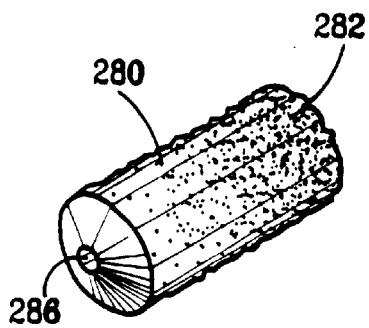
FIGS. 41a and 41b are drawn to bone dowels.

FIG. 39 is a synthetic cortical vertebral interbody device of another form. An inner portion is formed of RPR derived calcium phosphate. FIGS. 40a and c are of synthetic cortico-cancellous defect filling forms for bone restoration. Hard portion 270 is combined with an RPR-derived calcium phosphate portion 272 to give rise to these composite shaped bodies. FIG. 40b is a cancellous defect filling form for restoration. It is preferably formed from RPR-derived calcium phosphate 272 and preferably has a metallic, polymeric or ceramic underlayment of support, not shown. FIG. 41a is drawn to a cortico-cancellous bone dowel 280. Roughened area 282 is preferably derived from RPR material. A port for access to the interior of the dowel 286 is provided. The Dowel preferably has heterogeneous support portions in the interior.

Figure 41B:
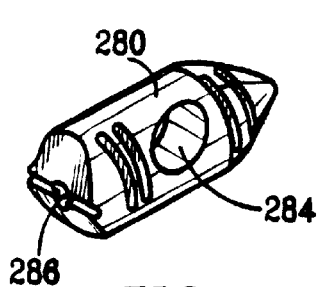

FIG. 41b is another bone dowel 280 in different conformation. Injection port 286 communicate with the interior. Orifice 284 and other structure facilitates spread of bone cement.

Figure 42:
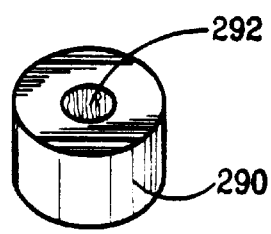
FIG. 42 is a synthetic cortical ring

FIG. 42 is a synthetic cortical ring. Hard outer ring structure may either surround a void 292 or the void may be filled, e.g. with RPR-derived calcium phosphate material. The ring may also have inner portion formed from a heterogeneous material.

Figure 43:
FIG. 43 is a cortical rod for orthopaedic restoration
Figure 44:
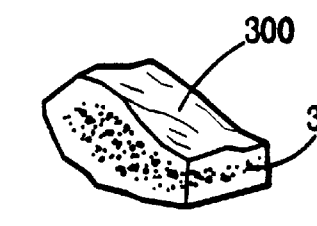
FIG. 44 is a synthetic cortico-cancellous "tri-cortical" device
Figure 46:
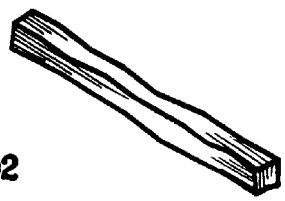
FIG. 46 is a "match stick" orthopaedic surgical splint.
Figure 47A:
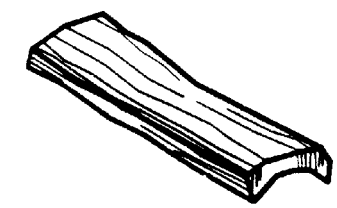
FIG. 47a and 47b are cortical struts for surgical use.
Figure 47B:
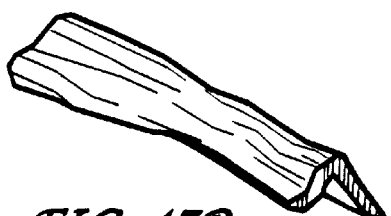

FIG. 43 is a cortical rod for orthopaedic restoration. FIG. 44 is a synthetic cortico-cancellous "tri-cortical" device for orthopaedic reconstructive surgery. Hard, preferably polymeric outer portion substantially 300 surrounds a porous inner structure 302, preferably derived from RPR calcium phosphate. FIG. 45 depicts a cortico-cancellous "crouton" for orthopaedic surgery. Polymeric shell, preferably one formed from bioactive polymer, 300, overlays a layer of RPR-derived calcium phosphate to form this composite shaped body. FIG. 46 is a "match stick" orthopaedic surgical splint. FIG. 47a and 47b are cortical struts. They are preferably comprised of a plurality of portions, one of which is an RPR-derived calcium phosphate.

Figure 48:
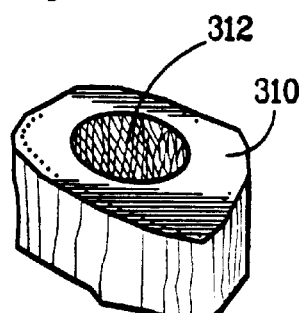
FIGS. 48, 49, 50a and 50b are cortical rings.
Figure 49:
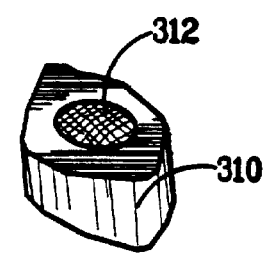
Figure 50A:
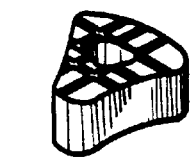
Figure 50B:
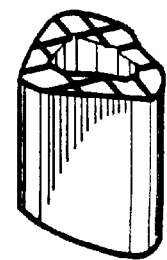
Figure 51:
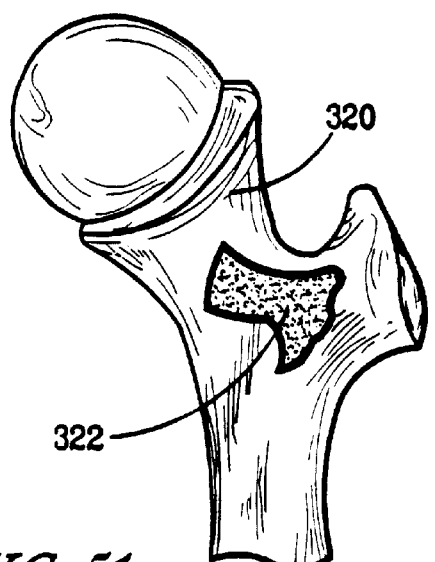
FIG. 51 depicts an artificial femur head for reconstructive surgery.
Figure 52:
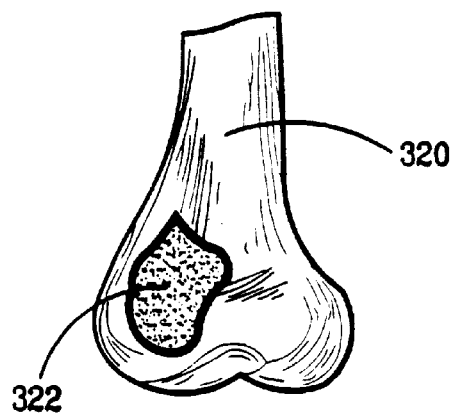
FIG. 52 is an artificial bone portion
Figure 53:
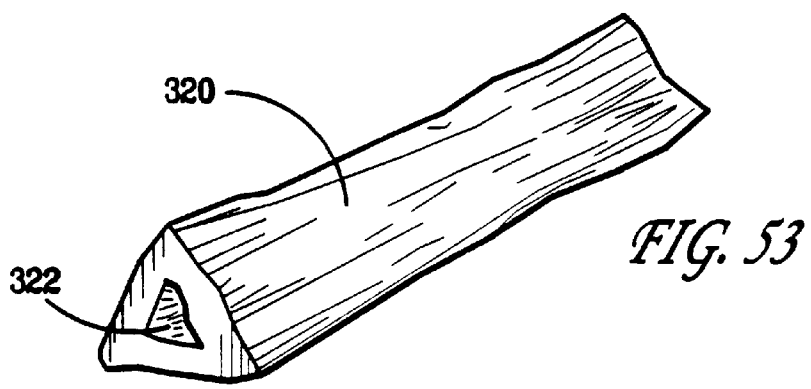
FIG. 53 is a strut or tube for reconstruction.
Figure 54:
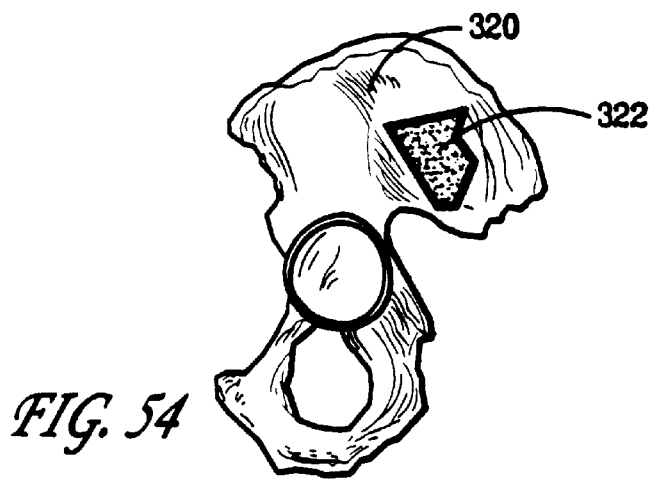
FIG. 54 is an acetabular/pelvic form for orthopaedic reconstruction.

FIGS. 48 and 49 show cortical rings having bioactive polymeric outer portion 310 and RPR-derived calcium phosphate inner portion 312. FIGS. 50a and 50b are cortical rings. These preferably have heterogenous inner support or reinforcement portions. FIG. 51 depicts an artificial femur head for reconstructive surgery. Outer portion 320 is preferably formed from hardened polymer while an inner portion 322 is RPR-derived calcium phosphate. This structure mimics natural bone FIG. 52 is an artificial bone portion having hard outer portion and RPR-derived calcium phosphate inner portion. FIG. 53 is a strut or tube showing RPR-derived inner portion 322 surrounded by hardened polymer 320. FIG. 54 is an acetabular/pelvic form for orthopaedic reconstruction. The inner RPR structure 322 and outer polymeric portions 320 are shown.

Figure 55A:
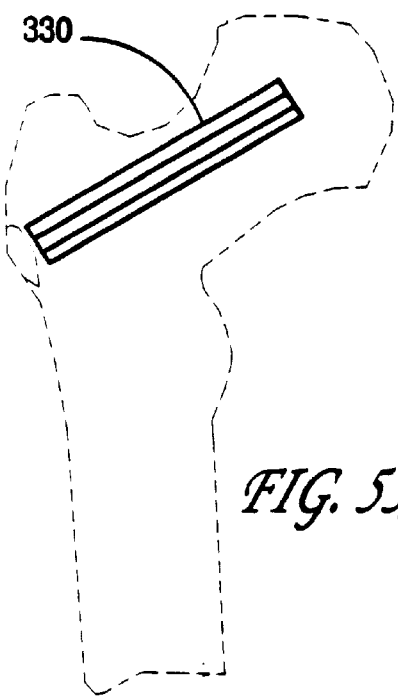
FIG. 55a and b depict insertion of a femoral hip dowel into a femur.
Figure 55B:
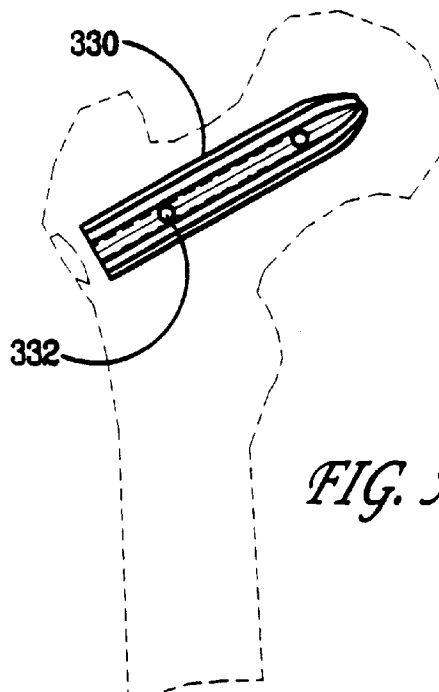
Figure 56A:
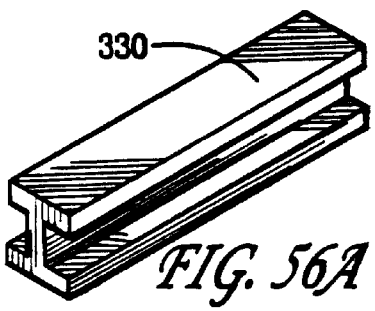
FIGS. 56a through *d* are different forms of dowels for orthopaedic use.
Figure 56B:
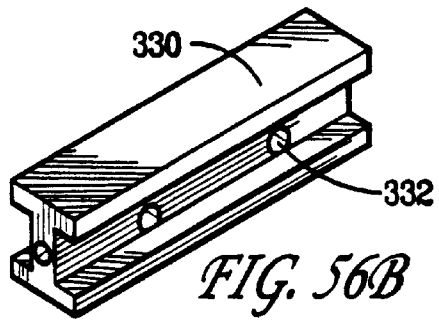
Figure 56C:
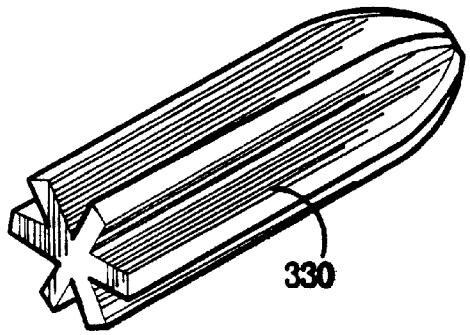
Figure 56D:
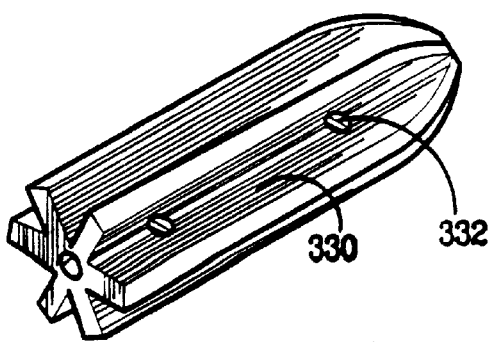

FIGS. 55a and b depict insertion of a femoral hip dowel 330 into a femur, shown in phantom, requiring restoration. Access ports 332 permit the injection of hardenable material, such as bone cement, into the dowel and, via the ports, around the dowel to effect fixation in the femur head. FIGS. 56a through d are different forms of dowels 330 of the type useful for hip or other reconstruction. Optional access ports 332 are present in FIGS. 56b and 56d.

EXAMPLES

Example 1

Low Temperature Calcium Phosphate Powders

An aqueous solution of 8.51 g 50 wt % hypophosphorous acid, $H_3PO_2$ (Alfa/Aesar reagent #14142, CAS #6303-21-5), equivalent to 71.95 wt % $[PO_4]^{-3}$ was combined with 8.00 g distilled water to form a clear, colorless solution contained in a 250 ml Pyrex beaker. To this solution was added 22.85 g calcium nitrate tetrahydrate salt, $Ca(NO_3)_2 \cdot 4H_2O$ (ACS reagent, Aldrich Chemical Co., Inc. #23,712-4, CAS #13477-34-4), equivalent to 16.97 wt % Ca. The molar ratio of Ca/phosphate in this mixture was 3/2 and the equivalent solids level [as $Ca_3(PO_4)_2$] was 25.4 wt %. Endothermic dissolution of the calcium nitrate tetrahydrate proceeded under ambient temperature conditions, eventually forming a homogeneous solution. Warming of this solution above 25° C. initiated a reaction in which the solution vigorously bubbled while evolving red-brown acrid fumes characteristic of $NO_{x(g)}$. The sample turned into a white, pasty mass which foamed and pulsed with periodic expulsion of $NO_{x(g)}$. After approximately two minutes, the reaction was essentially complete, leaving a white, pasty mass which was warm to the touch. After cooling to room temperature, the solid (A) was stored in a polyethylene vial.

Three days after its preparation, a few grams of the damp, pasty solid were immersed in 30 ml distilled water in order to "wash out" any unreacted, water soluble components. The solid was masticated with a spatula in order to maximize solid exposure to the water. After approximately 15 minutes, the solid was recovered on filter paper and the damp solid (B) stored in a polyethylene vial.

X-ray diffraction (XRD) patterns were obtained from packed powder samples using the Cu-Kα line ($\lambda$=1.7889 Angstrom) from a Rigaku Geigerflex instrument (Rigaku/USA, Inc., Danvers, Mass. 01923) run at 45 kV/30 mA using a 2 degree/minute scan rate over the 2θ angular range from 15–50° or broader. Samples were run either as prepared or following heat treatment in air in either a Thermolyne type 47900 or a Ney model 3-550 laboratory furnace. XRD analysis of the samples yielded the following results:

| Sample | Heat treatment | Major phase | Minor phase |
|---|---|---|---|
| Unwashed (A) | As prepared | Undetermined | — |
| Unwashed (A) | 300° C., 1 hour | Monetite [$CaHPO_4$] | — |
| Unwashed (A) | 500° C., 1 hour | Whitlockite [$\beta$-$Ca_3(PO_4)_2$] | $CaH_2P_2O_7$ |
| Unwashed (A) | 700° C., 1 hour | Whitlockite [$\beta$-$Ca_3(PO_4)_2$] + $HA_p[Ca_5(PO_4)_3(OH)]$ | |
| Washed (B) | As prepared | Monetite [$CaHPO_4$] | |
| Washed (B) | 100° C., 1 hour | Monetite [$CaHPO_4$] | |

Additional amounts of $NO_{x(g)}$ were evolved during firing of the samples at or above 300° C.

A sample of the powder produced according to this Example was submitted to an outside laboratory for analysis (Corning, Inc., CELS-Laboratory Services, Corning, N.Y. 14831). The results of this outside lab analysis confirmed that the powder fired at 700° C. was comprised of whitlockite and hydroxyapatite.

Example 2

Low Temperature Calcium Phosphate Powder

Example 1 was repeated using five times the indicated weights of reagents. The reactants were contained in a 5½ diameter Pyrex crystallizing dish on a hotplate with no agitation. Warming of the homogeneous reactant solution above 25° C. initiated an exothermic reaction which evolved red-brown acrid flumes characteristic of $NO_{x(g)}$. Within a few seconds following onset of the reaction, the sample turned into a white, pasty mass which continued to expel $NO_{x(g)}$ for several minutes. After approximately five minutes, the reaction was essentially complete leaving a damp solid mass which was hot to the touch. This solid was cooled to room temperature under ambient conditions for approximately 20 minutes and divided into two portions prior to heat treatment.

Heat treatment and X-ray diffraction of this solid were conducted as described in Example 1. Following heat treatment in air, XRD indicated the fired solids to be composed of:

| Sample | Heat treatment | Major phase | Minor phase |
|---|---|---|---|
| A | 500° C., 1 hour | Whitlockite [β-Ca$_3$(PO$_4$)$_2$] | HAp [Ca$_5$(PO$_4$)$_3$(OH)] |
| B | 700° C., 1 hour | HAp [Ca$_5$(PO$_4$)$_3$(OH)] | Whitlockite [β-Ca$_3$(PO$_4$)$_2$] |

Example 3

Low Temperature Calcium Phosphate Powders

An aqueous solution of 8.51 g 50 wt % H$_3$PO$_2$ was combined with 8.00 g of 25.0 wt % aqueous solution of calcium acetate monohydrate, Ca(O$_2$CCH$_3$)$_2$.H$_2$O (ACS reagent, Aldrich Chemical Co., Inc. #40,285-0, CAS 5743-26-0), equivalent to 5.69 wt % Ca, to give a clear, colorless solution contained in a 250 ml Pyrex beaker. To this solution was added 20.17 g Ca(NO$_3$)$_2$.4H$_2$O salt. The molar ratio of Ca/phosphate in this mixture was 3/2 and the equivalent solids level [as Ca$_3$(PO$_4$)$_2$] was 27.3 wt %. Endothermic dissolution of the calcium nitrate tetrahydrate salt proceeded giving a homogeneous solution once the sample warmed to room temperature. Further warming of this solution to >25° C. on a hotplate initiated a reaction which proceeded as described in Example 1. After approximately three minutes, the reaction was essentially complete leaving a moist, white, crumbly solid which was hot to the touch and which smelled of acetic acid. After cooling to room temperature, the solid was stored in a polyethylene vial.

Heat treatment and X-ray diffraction analysis of this solid were conducted as described in Example 1. Following heat treatment in air at 500° C. for either 0.5 or 1 hour, XRD indicated the solid to be composed of whitlockite as the primary phase along with hydroxyapatite as the secondary phase. XRD results indicate that the relative ratio of the two calcium phosphate phases was dependent on the duration of the heat treatment and the presence of the acetate anion, but no attempts were made to quantify the dependence.

Heated to 500° C., 1 hour (Major) Whitlockite [β-Ca$_3$(PO$_4$)$_2$] (minor) Ca$_5$(PO$_4$)$_{3-x}$(CO$_3$)$_x$(OH)

Comparing the XRD spectra from these results in Example 3 with XRD spectra from Example 1 shows the difference in the amount of HAp- Ca$_5$(PO$_4$)$_{3-x}$(CO$_3$)$_x$(OH) phase present for each minor phase. The samples in Example 1 exhibited no acetate whereas the samples in Example 3 showed acetate present. This is indicative of the counteranion effect on crystal formation.

Fourier Transform Infrared (FTIR) spectra were obtained using a Nicolet model 5DXC instrument (Nicolet Instrument Co., 5225 Verona Rd. Madison, Wis. 53744) run in the diff-use reflectance mode over the range of 400 to 4000 cm$^{-1}$. The presence of the carbonated form of HAp is confirmed by the FTIR spectra, which indicated the presence of peaks characteristic of [PO$_4$]$^{-3}$ (580–600, 950–1250 cm$^{-1}$) and of [CO$_3$]$^{-2}$ (880, 1400, & 1450 cm$^{-1}$). The P=O stretch, indicated by the strong peak at 1150–1250 cm$^{-1}$, suggests a structural perturbation of hydroxyapatite by the carbonate ion.

Example 4

Colloidal SiO$_2$ added to calcium phosphate mixtures via RPR

An aliquot of 8.00 g 34.0 wt % SiO$_2$ hydrosol (Nalco Chemical Co., Inc. #1034A, batch #B5G453C) was slowly added to 8.51 g 50 wt % aqueous solution of H$_3$PO$_2$ with rapid stirring to give a homogeneous, weakly turbid colloidal dispersion. To this dispersion was added 22.85 g Ca(NO$_3$)$_2$.4H$_2$O salt such that the molar ratio of calcium/phosphate in the mixture was 3/2. Endothermic dissolution of the calcium nitrate tetrahydrate proceeded giving a homogeneous colloidal dispersion once the sample warmed to room temperature. The colloidal SiO$_2$ was not flocculated despite the high acidity and ionic strength in the sample. Warming of the sample on a hotplate to >25° C. initiated a reaction as described in Example 1. The resultant white, pasty solid was stored in a polyethylene vial.

Heat treatment and X-ray diffraction of this solid were conducted as described in Example 1. Following heat treatment in air at 500° C. for 1.0 hour, XRD indicated the solid to be composed of whitlockite plus hydroxyapatite.

| | | |
|---|---|---|
| Heated to 300° C., 2 hours | (Major) | Calcium pyrophosphate [Ca$_2$P$_2$O$_7$] |
| | (minor) | Octacalcium phosphate [Ca$_4$H(PO$_4$)$_3$.2H$_2$O] |
| Heated to 500° C., 1 hour | (Major) | Whitlockite [b-Ca$_3$(PO$_4$)$_2$] |
| | (minor) | HAp [Ca$_5$(PO$_4$)$_3$(OH)] |

Example 5

Low Temperature Calcium Phosphate Powder

Example 1 was repeated with the addition of 10.00 g dicalcium phosphate dihydrate, DCPD, CaHPO4.2H$_2$O (Aldrich Chemical Co., Inc. #30,765-3, CAS #7789-77-7) to the homogeneous solution following endothermic dissolution of the calcium nitrate salt. The DCPD was present both as suspended solids and as precipitated material (no agitation used). Warming of the sample to >25° C. initiated an exothermic reaction as described in Example 1, resulting in the formation of a white, pasty solid. Heat treatment and X-ray diffraction of this solid were conducted as described in Example 1. Following heat treatment in air at 500° C. for 1 hour, XRD indicated the solid to be composed of whitlockite as the primary phase along with calcium pyrophosphate (Ca$_2$P$_2$O$_7$) as the secondary phase.

| | | |
|---|---|---|
| Heated to 500° C., 1 hour | (Major) | Whitlockite [β-Ca$_3$(PO$_4$)$_2$] |
| | (minor) | Ca$_2$P$_2$O$_7$ |

Example 6

Low Temperature Zinc Phosphate Powder Preparation

An aqueous solution of 8.51 g 50 wt % H$_3$PO$_2$ in 8.00 g distilled water was prepared as described in Example 1. To this solution was added 28.78 g zinc nitrate hexahydrate salt, Zn(NO$_3$)$_2$.6H$_2$O (ACS reagent, Aldrich Chemical Co., Inc. #22,873-7, CAS #10196-18-6), equivalent to 21.97 wt % Zn. The molar ratio of Zn/phosphate in this mixture was 3/2 and the equivalent solids level [as Zn$_3$(PO$_4$)$_2$] was 27.5 wt %. Endothermic dissolution of the zinc nitrate hexahydrate proceeded giving a homogeneous solution once the sample warmed to room temperature. Further warming of this solution to >25° C. on a hotplate initiated a reaction in which the solution vigorously evolved red-brown acrid fumes of NO$_{x(g)}$, The reaction continued for approximately 10 minutes while the sample remained a clear, colorless solution, abated somewhat for a period of five minutes, then vigorously resumed finally resulting in the formation of a mass of moist white solid, some of which was very adherent to the walls of the Pyrex beaker used as a reaction vessel. The hot solid was allowed to cool to room temperature and was stored in a polyethylene vial.

Heat treatment and X-ray diffraction of this solid were conducted as described in Example 1. Following heat treatment in air at 500° C. for 1 hour, XRD indicated the solid to be composed of $Zn_3(PO_4)_2$ (PDF 30-1490).

Heated to 500° C., 1 hour (Major) $Zn_3(PO_4)_2$

Example 7

Low Temperature Iron Phosphate Powders

An aqueous solution of 17.50 g 50 wt % $H_3PO_2$ was combined with 15.00 g distilled water to form a clear, colorless solution contained in a 250 ml Pyrex beaker on a hotplate/stirrer. To this solution was added 53.59 g ferric nitrate nonahydrate salt, $Fe(NO_3)_3 \cdot 9H_2O$ (ACS reagent, Alfa/Aesar reagent #33315, CAS #7782-61-8), equivalent to 13.82 wt % Fe. The molar ratio of Fe/phosphate in this mixture was 1/1 and the equivalent solids level [as $FePO_4$] was 23.2 wt %. Endothermic dissolution of the ferric nitrate nonahydrate salt proceeded partially with gradual warming of the reaction mixture, eventually forming a pale lavender solution plus undissolved salt. At some temperature >25° C., an exothermic reaction was initiated which evolved $NO_{x(g)}$. This reaction continued for approximately 15 minutes during which time the reaction mixture became syrup-like in viscosity. With continued reaction, some pale yellow solid began to form at the bottom of the beaker. After approximately 40 minutes of reaction, the sample was allowed to cool to room temperature. The product consisted of an inhomogeneous mixture of low density yellow solid at the top of the beaker, a brown liquid with the consistency of caramel at the center of the product mass, and a sand colored solid at the bottom of the beaker. The solids were collected as separate samples insofar as was possible.

Heat treatment and X-ray diffraction of the solid collected from the top of the beaker were conducted as described in Example 1. Following heat treatment in air at 500° C. for 1 hour, XRD indicated the solid to be composed of graftonite [$Fe_3(PO_4)_2$] (PDF 27-0250) plus some amorphous material, suggesting that the heat treatment was not sufficient to induce complete sample crystallization as illustrated below:

Heated to 500° C., 1 hour (Major) Graftonite [$Fe_3(PO_4)_2$] Some mechanism apparently occurs by which $Fe^{3+}$ was reduced to $Fe^{2+}$.

Example 8

Low Temperature Calcium Phosphate Powders

An aqueous solution of 19.41 g 50 wt % $H_3PO_2$ was combined with 5.00 g distilled water to form a clear, colorless solution contained in a 250 ml Pyrex beaker. To this solution was added 34.72 g $Ca(NO_3)_2 \cdot 4H_2O$. The molar ratio of Ca/phosphate in this mixture was 1/1 and the equivalent solids level [as $CaHPO_4$] was 33.8 wt %. Endothermic dissolution of the calcium nitrate tetrahydrate proceeded under ambient temperature conditions, eventually forming a homogeneous solution once the sample warmed to room temperature. Warming of this solution above 25° C. initiated a vigorous exothermic reaction which resulted in the evolution of $NO_{x(g)}$, rapid temperature increase of the sample to >100° C., and extensive foaming of the reaction mixture over the beaker rim, presumably due to flash boiling of water at the high reaction temperature. After cooling to room temperature, the reaction product was collected as a dry, white foam which was consolidated by crushing to a powder.

Heat treatment and X-ray diffraction of this solid were conducted as described in Example 1. Results are as follows:

| | | |
|---|---|---|
| Heated to 300° C., 2 hours | (Major) | $Ca_2P_2O_7$ |
| | (minor) | Octacalcium phosphate [$Ca_4H(PO_4)_3 \cdot 2H_2O$] |
| Heated to 500° C., 1 hour | (Major) | $Ca_2P_2O_7$ |

Example 9

Low Temperature Calcium Phosphate Powders

Example 3 was repeated using ten times the indicated weights of reagents. The reactants were contained in a 5½ diameter Pyrex crystallizing dish on a hotplate/stirrer. The reactants were stirred continuously during the dissolution and reaction stages. The chemical reaction initiated by heating the solution to >25° C. resulted in the evolution of $NO_{x(g)}$ for several minutes with no apparent effect on the stability of the system, i.e. the solution remained clear and colorless with no evidence of solid formation. After abating for several minutes, the reaction resumed with increased intensity resulting in the voluminous generation of $NO_{x(g)}$ and the rapid appearance of a pasty white solid material. The reaction vessel and product were both hot from the reaction exotherm. The product was cooled in air to a white crumbly solid which was stored in a polyethylene vial.

Heat treatment and X-ray diffraction of this solid were conducted as described in Example 1. Following heat treatment in air at 500° C. for either 0.5 or 1 hour, XRD indicated the solid to be composed of whitlockite as the primary phase along with hydroxyapatite as the secondary phase. XRD results indicate that the relative ratio of the two calcium phosphate phases was dependent on the duration of the heat treatment, but no attempts were made to quantify the dependence.

| | | |
|---|---|---|
| Heated to 500° C., 1 hour | (Major) | Whitlockite [b-$Ca_3(PO_4)_2$] |
| | (minor) | $Ca_5(PO_4)_{3-x}(CO_3)_x(OH)$ |

Example 10

Low Temperature Aluminum Phosphate Powders

An aqueous solution of 10.82 g 50 wt % $H_3PO_2$ was combined with 2.00 g distilled water to form a clear, colorless solution contained in a 250 ml Pyrex beaker. To this solution was added 30.78 g aluminum nitrate nonahydrate salt, $Al(NO_3)_3 \cdot 9H_2O$ (ACS reagent, Alfa/Aesar reagent #36291, CAS #7784-27-2), equivalent to 7.19 wt % Al. The molar ratio of Al/phosphate in this mixture was 1/1 and the equivalent solids level [as $AlPO_4$] was 22.9 wt %. Endothermic dissolution of the aluminum nitrate nonahydrate proceeded giving a homogeneous solution once the sample warmed to room temperature. Further warming of this solution to >25° C. on a hotplate initiated a reaction in which the solution vigorously evolved red-brown acrid fumes of $NO_{x(g)}$. Reaction continued for approximately 15 minutes during which the solution viscosity increased considerably prior to formation of a white solid.

Heat treatment and X-ray diffraction of this solid were conducted as described in Example 1. Following heat treatment in air at 500° C. for 0.5 hour, XRD analysis indicated the solid to be composed of $AlPO_4$(PDF 11-0500) plus some amorphous material, suggesting that the heat treatment was not sufficient to induce complete sample crystallization.

Example 11

Low Temperature Calcium Phosphate Powders

An aqueous solution of 8.06 g 50 wt % $H_3PO_2$ reagent was combined with 6.00 g distilled water to form a clear, colorless solution in a 250 ml Pyrex beaker on a hotplate/stirrer. To this solution was added 19.23 g $Ca(NO_3)_2.4H_2O$. The molar ratio of Ca/phosphate in this sample was 4/3 and the equivalent solids [as octacalcium phosphate, $Ca_8H_2(PO_4)_6\text{-}5H_2O$] was 30.0 wt %. Endothermic dissolution of the calcium nitrate tetrahydrate proceeded under ambient conditions, eventually forming a homogeneous solution once the sample warmed to room temperature. Warming of the solution above 25° C. initiated a vigorous exothermic reaction as described in Example 1. After approximately three minutes, the reaction was essentially complete leaving a moist, white, pasty solid.

Heat treatment and X-ray diffraction of this solid were conducted as described in Example 1. Following heat treatment in air at 500° C. for 0.5 hour, XRD indicated the solid to be composed of whitlockite as the primary phase along with hydroxyapatite as the secondary phase. There was no evidence for the formation of octacalcium phosphate (OCP), despite the initial sample stoichiometry. This result suggests that (a) alternate heat treatments are necessary to crystallize OCP and/or (b) excess Ca is present in the intermediate powder.

| Heated to 500° C., 0.5 hour | (Major) | Whitlockite [b-$Ca_3(PO_4)_2$] |
|---|---|---|
| | (minor) | HAp $Ca_5(PO_4)_3(OH)$ |

Example 12

Low Temperature Calcium Phosphate Powders

Example 11 was repeated except that no distilled water was used in preparation of the reaction mixture. Warming of the homogeneous solution above 25° C. initiated an exothermic reaction as described in Example 11. After approximately three minutes, the reaction was essentially complete leaving a moist, pasty, white solid.

Heat treatment and X-ray diffraction of this solid were conducted as described in Example 1. Following heat treatment in air at 500° C. for 0.5 hour, XRD indicated the solid to be composed of calcium pyrophosphate ($Ca_2P_2O_7$).

Heated to 500° C., 0.5 hour (Major) $Ca_2P_2O_7$

Example 13

Low Temperature Hydrothermal (HYPR) Calcium Phosphates

An aqueous solution of 50 wt % calcium nitrate tetrahydrate, $Ca(NO_3)_2\text{-}4H_2O$ (ACS reagent, Aldrich Chemical Co., Inc. #23,712-4, CAS #13477-34-4) was prepared by dissolving 250.0 g of the salt in 250.0 g distilled water. This solution was equivalent to 8.49 wt % Ca. A total of 47.0 g of this solution was added, with rapid agitation, to an aqueous solution of 50 wt % sodium hypophosphite monohydrate, $NaH_2PO_2\text{—}H_2O$ (Alfa/Aesar reagent #14104, CAS #10039-56-2) also prepared by dissolving 250.0 g of the salt in 250.0 g distilled water. The sodium hypophosphite solution was equivalent to 44.80 wt % $[PO_4]^{-3}$. The clear, colorless solution of calcium nitrate and sodium hypophosphite was then diluted with 40.3 g distilled water. The molar ratio of Ca/phosphate in this mixture was 5/3, and the equivalent solids level [as $Ca_5(PO_4)_3(OH)$ (hydroxyapatite)] was 10.0 wt %. The sample was hydrothermally treated using a 300 cc volume stirred high pressure bench reactor (Model no. 4561 Mini Reactor, Parr Instrument Co., Moline, Ill. 61265) equipped with a temperature controller/digital tachometer unit (Model no. 4842, Parr Instrument Co.) and dial pressure gauge. All wetted parts of the reactor were fabricated from type 316 stainless steel. Ordinarily, type 316SS is not the material of choice for inorganic acid systems such as the solution precursors used in this invention, since phosphoric acid can attack stainless steel at elevated temperatures and pressures. However, in the practice of this invention, direct contact (i.e. wetting) of the reactor surfaces was avoided through the use of a Pyrex glass liner. Only the stirrer and thermocouple sheath were immersed in the reactant solutions and no corrosion was observed. In addition, it is assumed that the high nitrate ion concentration in the reactant mixture provided a passivating environment for the type 316SS.

One hundred grams (approximately 100 ml) of the calcium nitrate—sodium hypophosphite solution was placed in the Pyrex liner of the reactor and the intervening space between the glass liner and the reactor vessel was filled with distilled water to the level of the sample. This ensured maximum heat transfer to the sample since the reactor was externally heated by an electric mantle. The approx. 100 ml sample volume left sufficient head space in the reactor to accommodate solution expansion at elevated temperatures. The reactor was sealed by compression of a Teflon gasket. Heating of the reactor was performed at the maximum rate of the controller to a set point of 202° C. with constant stirring (500 r.p.m.). The heating profile, as monitored by a thermocouple immersed in the reactant mixture, was as follows:

| REACTOR THERMAL PROFILE | | | | | | | | | |
|---|---|---|---|---|---|---|---|---|---|
| Time (min) | 0 | 5 | 10 | 15 | 20 | 25 | 30 | 35 | 36 |
| Temp. (° C.) (+/−2° C.) | 22 | 49 | 103 | 122 | 145 | 155 | 179 | 197 | 200 (hold) |
| Pressure (psi) | — | — | — | — | — | — | 160 | 210 | 220 |

After holding at 200+/−3° C. for 12 minutes, the temperature rapidly increased to 216° C. with a resultant increase in reactor pressure to approximately 330 psi. This exothermic event quickly subsided as evidenced by the rapid drop in reactor temperature to 208° C. within two minutes as the Parr reactor approached thermal equilibrium via a near-adiabatic process. After 15 minutes at 200° C., the reactor was removed from the heating mantle, quenched in a cold water bath, and opened after the head space was vented to ambient pressure.

A white precipitate was present in the glass liner. The solid was collected by vacuum filtration on a 0.45 micron membrane filter (Millipore, Inc., Bedford, Mass., 01730), washed several times with distilled water, and dried at approximately 55° C. in a forced convection oven. X-ray diffraction of this solid was conducted as described in Example 1.

X-Ray diffraction results indicate a unique, unidentifiable diffraction pattern.

Example 14

Low Temperature Hydrothermal (HYPR) Calcium Phosphate Powders

Example 13 was repeated except that 40.3 g of 1.0 M NaOH solution was added with rapid stirring to the homogeneous solution of calcium nitrate and sodium hypophosphite instead of the distilled water. This base addition resulted in the formation of a milk white dispersion, presumably due to precipitation of $Ca(OH)_2$.

The sample was hydrothermally processed as described in Example 13 with the temperature set point at 207° C.. The temperature ramp to 160° C. (25 minutes) was as indicated for Example 13. At 30 minutes into the run, an exotherm occurred causing the temperature of the reaction mixture to rise to a maximum of 221° C. within five minutes with a corresponding pressure increase to 370 psi. At 38 minutes into the experiment, the reactor was quenched to room temperature.

The reaction product consisted of a small amount of white precipitate. The material was collected as described in Example 13. X-ray diffraction of the dried sample was conducted as described in Example 1. XRD results indicated the solid to be comprised of the same unidentifiable pattern (crystal phase) found in Example 13 and minor amounts of HAp-$[Ca_5(PO_4)_3(OH)]$.

Example 15

Low Temperature Hydrothermal (HYPR) Calcium Phosphate Powders

A total of 47.0 g of a 50 wt % aqueous solution of calcium nitrate tetrahydrate was diluted with 53.0 g distilled water. Then, 6.00 g calcium hypophosphite salt, $Ca(H_2PO_2)_2$ (Alfa/Aesar reagent #56168, CAS #7789-79-9), equivalent to 23.57 wt Ca and 111.7 wt % $[PO_4]^{-3}$, was slurried into the $Ca(NO_3)_2$ solution using rapid agitation. An unknown amount of the calcium hypophosphite remained undissolved in the room temperature sample. The solubility behavior of $Ca(H_2PO_2)_2$ in the $Ca(NO_3)_2$ solution at elevated temperatures is unknown. The molar ratio of Ca/phosphate in this system was 1.91.

This sample was hydrothermally processed as described in Example 13 with the temperature set point at 212° C.. The temperature ramp to 200° C. was as indicated for Example 13. At 39 minutes into the run, an exotherm occurred causing the temperature of the reaction mixture to rise to a maximum of 252° C. within three minutes with a corresponding pressure increase to 640 psi. At 44 minutes into the experiment, the reactor was quenched to room temperature.

The reaction product appeared as a voluminous white precipitate plus some suspended solids. The material was collected as described in Example 13. X-ray diffraction of the dried solid was conducted as described in Example 1. XRD showed the major peak at position 30.2° (2-theta) which indicated the solid to be monetite, $CaHPO_4$. The unique crystal morphology is depicted in the scanning electron micrograph representation in FIG. 2.

Mixtures of the above described RPR and HYPR powders are useful in the formation of self-setting calcium phosphate cements for the repair of dental and orthopaedic defects. The addition of specific components and solubilizing liquids can also be added to form the precursor bone mineral constructs of this invention.

Example 16

Cement Compositions

Approximately 1.4 g of an alkaline solution (7 molar) formed using NaOH and distilled water, was mixed with 1.1 g of HYPR monetite [Example 15] and 1.1 g of RPR β-TCP-HAp($CO_3$) [Example 3] in a glass mortar and pestle for ~45 seconds. After mixing, a smooth paste was formed, which was scooped into a 3 ml polypropylene syringe and sealed for 20 minutes without being disturbed. Room temperature setting was observed after 20 minutes, which was indicated by the use of a 454 gram Gilmore needle. The hardened cement analyzed by X-ray diffraction showed peaks which revealed a conversion to primarily type-B, carbonated apatite which is the desired bone mineral precursor phase:

| Cement XRD revealed | (Major) | $Ca_5(PO_4)_{3-x}(CO_3)_x(OH)$ |
|---|---|---|
| | (minor) | Whitlockite [b-$Ca_3(PO_4)_2$] |

Example 17

Cement Compositions

A stock solution was formed with the approximately 7 M NaOH solution used in Example 1 and 1.0% polyacrylic acid (PAA). PAA is used as a chelating setting additive and wetting agent. The above solution was used with several powder combinations to form setting cements. A 50/50 powder mix of HYPR monetite [Example 15] and RPR β-TCP-HAp($CO_3$) [Example 3], approximately 0.7 g, was mixed with a glass spatula on a glass plate with 0.39 g of the 1% PAA-NaOH solution (powder to liquid ratio=1.73). The cement was extruded through a 3 ml syringe and was set after being left undisturbed for 20 minutes at room temperature (23° C.).

Examples 18–34

| Example | Powder | Liquid | Powder/ Powder/ Liquid ratio (Consistency) | Set Time (min.) Gilmore Needle (454 grams) # = (1200 grams) |
|---|---|---|---|---|
| 18 | HYPR monetite + RPR (Ex.1) 500 ° C. | 7M NaOH Alkaline Sol'n | 1/1/1.2 (slightly wet paste) | <20 min (#) |
| 19 | HYPR monetite (Ex.15) + RPR (Ex.1) 700 ° C. | 7M NaOH Alkaline Sol'n | 1/1/1.2 (wet paste) | <20 min (#) |

-continued

| Example | Powder | Liquid | Powder/ Powder/ Liquid ratio (Consistency) | Set Time (min.) Gilmore Needle (454 grams) # = (1200 grams) |
|---|---|---|---|---|
| 20 | HYPR monetite (Ex.15) + −50 μm 45S5# glass | 7M NaOH Alkaline Sol'n | 1/1/1 (sl. wet paste) | 15—min |
| 21 | RPR(Ex.1) 500 °C. 'neat' | 7M NaOH Alkaline Sol'n | 1.5/1 (wet paste) | >40 min |
| 22 | RPR (Ex.1) 300 °C. + RPR (Ex.9) 500° C. | 7M NaOH Alkaline Sol'n | 1.7/1 (sl. wet paste) | 40 min |
| 23 | HYPR monetite (Ex.15) + Commercial β-TCP | 7M NaOH Alkaline Sol'n | 1/1/1.4 (v.gritty,wet) | No Set up to 24 hrs. |
| 24 | HYPR monetite (Ex.15) + RPR (Ex.2) 500 °C. | 7M NaOH Alkaline Sol'n | 1/1/1.4 (slightly wet paste) | 20 min (#) |
| 25 | HYPR monetite (Ex.15) + RPR (Ex.2) 500 °C. | 7M NaOH Alk. Sol'n + 20% PAA | 1/1/1 (claylike paste) | <30 min sl. set |
| 26 | HYPR monetite (Ex.15) + RPR (Ex.2) 500 °C. | 7M NaOH Alk. Sol'n + 5% PAA | 1/1/1 (claylike paste) | 35 min |
| 27 | HYPR monetite (Ex.15) + RPR (Ex.11)500 ° C. | 7M NaOH Alk. Sol'n + 1% PAA | 1/1/1.2 (slightly dry paste) | 12–15 min |
| 28 | HYPR monetite (Ex. 15) + RPR (Ex.1) 500 °C. | 10 wt % $Ca(H_2PO_2)_2$ (aq) | 1/1/1.2 (very wet paste) | 1 hr 15 min |
| 29 | RPR (Ex.11)500 °C. 'neat' | 10 wt % $Ca(H_2PO_2)_2$ (aq) | 1.7/1 (very wet paste) | 45 min |
| 30 | RPR (Ex.11)500 °C. 'neat' | 10 wt % $Ca(H_2PO_2)_2$ (aq) | 2.5/1 (sl. dry paste/putty) | 20 min |
| 31 | RPR (Ex.11)500° C. 'neat' | 10 wt % $Ca(H_2PO_2)_2$ + 1 wt % $H_2PO_2$ (aq) | 2.25/1 (very good paste/putty) | 15 min |
| 32 | HYPR monetite (Ex.15) + RPR (Ex.11)500° C. | 3.5 M NaOH Alk. Sol'n. | 1/1/1 (good paste/putty) | 35 min. *12 min. |
| 33 | HYPR monetite (Ex.15) + RPR (Ex.11)500° C. | 3.5 M NaOH Alk. Sol'n. | 1/3/2 (paste/putty) | 38 min. *15 min. |
| 34 | HYPR monetite (Ex.15) + RPR (Ex.11)500° C. | Saline, EDTA buffered | 1/1/1 (good paste/putty) | 43 min. *20 min. |

*Set Time at 37° C., 98% Relative Humidity.
HYPR monetite = HYdrothermally PROCESSED monetite ($CaHPO_4$).
RPR = Reduction-oxidation Precipitation Reaction.
45S5 glass = {24.5% CaO-24.5% $Na_2O$-6% $P_2O_5$-45% $SiO_2$ (wt %)}.
PAA = Polyacrylic acid.
Commercial β-TCP from Clarkson Chromatography Products, Inc. (S. Williamsport, PA)

Example 35
Low Temperature Neodymium Phosphate Powders

An aqueous solution of 11.04 g of 50 wt. % $H_3PO_2$ was diluted with 5.00 g distilled water to form a clear, colorless solution contained in a 250 ml fluoropolymer resin beaker on a hotplate/magnetic stirrer. Added to this solution was 36.66 g neodymium nitrate hexahydrate salt, $Nd(NO_3)_3 \cdot 6H_2O$ (Alfa/Aesar reagent #12912, CAS #16454-60-7), equivalent to 32.90 wt % Nd. The molar ratio of the Nd/P in this mixture was 1/1 and the equivalent solids level (as $NdPO_4$) was 38.0 wt. %. Endothermic dissolution of the neodymium nitrate hexahydrate salt proceeded with gradual warming of the reaction mixture, eventually forming a clear, homogeneous lavender solution at room temperature. Heating of this solution with constant agitation to approximately 70° C. initiated a vigorous endothermic reaction which resulted in the evolution of $NO_{x(g)}$, rapid temperature increase of the sample to approximately 100° C., and finally, formation of a pasty lavender mass. Heat treatment of the pasty solid and subsequent X-ray diffraction analysis of the fired solid were conducted as described in Example 1. Results of the analysis are as follows:

| | |
|---|---|
| Heated to 500° C., 45 minutes (Major) | Neodymium phosphate hydrate [NdPO$_4$-0.5H$_2$O](PDF 34-0535) |
| Heated to 700° C., 45 minutes (Major) | Monazite-Nd [NdPO$_4$] (PDF 46-1328) |

Example 36

Low Temperature Cerium Phosphate Powders

An aqueous solution of 11.23 g of 50 wt. % $H_3PO_2$ was diluted with 5.00 g distilled water to form a clear, colorless solution contained in a 250 ml fluoropolymer resin beaker on a hotplate/magnetic stirrer. Added to this solution was 36.94 g cerium nitrate hexahydrate salt, $Ce(NO_3)_3\cdot 6H_2O$ (Johnson-Matthey reagent #11329-36), equivalent to 32.27 wt % Ce. The molar ratio of the Ce/P in this mixture was 1/1 and the equivalent solids level (as $CePO_4$) was 37.6 wt %. Endothermic dissolution of the neodymium nitrate hexahydrate salt proceeded with gradual warming of the reaction mixture, eventually forming a clear, homogeneous colorless solution at room temperature. Heating of this solution with constant agitation to approximately 65° C. initiated a vigorous endothermic reaction which resulted in the evolution of $NO_{x(g)}$, rapid temperature increase of the sample to approximately >100° C., and finally, formation of a pasty light grey mass. Heat treatment of the pasty solid and subsequent X-ray diffraction analysis of the fired solid were conducted as described in Example 1. Results of the XRD analysis are as follows:

Heated to 700° C., 45 minutes (Major) Monazite-Ce [$CePO_4$] (PDF 32-0199)

Example 37

Low Temperature Yttrium Phosphate Powders

An aqueous solution of 14.36 g of 50 wt. % $H_3PO_2$ was diluted with 5.00 g distilled water to form a clear, colorless solution contained in a 250 ml fluoropolymer resin beaker on a hotplate/magnetic stirrer. Added to this solution was 41.66 g yttrium nitrate hexahydrate salt, $Y(NO_3)_3\cdot 6H_2O$ (Alfa/Aesar reagent #12898, CAS #13494-98-9), equivalent to 23.21 wt % Y. The molar ratio of the Y/P in this mixture was 1/1 and the equivalent solids level (as $YPO_4$) was 32.8 wt %. Endothermic dissolution of the yttrium nitrate hexahydrate salt proceeded with gradual warming of the reaction mixture, eventually forming a clear, homogeneous colorless solution at room temperature. Heating of this solution with constant agitation to approximately 75° C. initiated a vigorous endothermic reaction which resulted in the evolution of $NO_{x(g)}$, rapid temperature increase of the sample to approximately >100° C., and finally, formation of a pasty white mass. Heat treatment of the pasty solid and subsequent X-ray diffraction analysis of the fired solid were conducted as described in Example 1. Results of the XRD analysis are as follows: Heated to 700° C., 45 minutes (Major) Xenotime [$YPO_4$] (PDF 11-0254)

Example 38

Broad Applicabililty

A wide variety of minerals can be made in accordance with the present invention. In the following two tables, oxidizing and reducing agents are listed. Any of the listed oxidants can be reacted with any of the listed reducing agents and, indeed, blends of each may be employed. Appropriate stoichiometry will be employed such that the aforementioned reaction is caused to proceed. Also specified are possible additives and fillers to the reactions. The expected products are given as are some of the expected fields of application for the products. All of the following are expected generally to follow the methodology of some or all of the foregoing Examples.

| Oxidizing Agents | Reducing Agents | Additives | Product(s) |
|---|---|---|---|
| Compounds of the form $XNO_3$, where X = H, Li, Na, K, Rb, Cs, Cu, Ag, and Hg. | Oxoacids of Group 5B, 6B, and 7B, (where 5B includes N, P, and As; 6B includes S, Se, and Te; 7B includes Cl, Br, and I). | $Al_2O_3$, $ZrO_2$, $TiO_2$, $SiO_2$, $Ca(OH)_2$, DCPD, DCPA, HAp, TCP, TTCP, MCMP, $ZrSiO_4$, W-metal, Fe metal, Ti metal, Carbon black, C-fiber or flake, $CaF_2$, NaF, carbides, nitrides, glass fibers, glass particulate, glass-ceramics, alumina fibers, ceramic fibers, bioactive ceramic fibers and particulates, polyacrylic acid, polyvinyl alcohol, polymethyl-methacrylate, polycarbonate, and other stable polymeric compounds. Acetates, formates, lactates, simple carboxylates, and simple sugars. | $XY(PO_4)$, $XY(SO_4)$, $XY(PO_4)(SO_4)$, $WXYZ(PO_4)(SO_4)(CO_3)$, $WXYZ(PO_4)(SO_4)(CO_3)(F,Cl,Br,I)$, $WXYZ(PO_4)(SO_4)$ $(CO_3)(F,Cl,Br,I)(OCl, OF, OBr, OI)$, in the form of fiber, flake, whisker, granule, coatings, agglomerates and fine powders. |
| Compounds of the form $X(NO_3)_2$, where X = Be, Mg, Ca, Sr, Ba, Cr, Mn, Fe, Co, Ni, Cu, Zn, Rh, Pd, Cd, Sn, Hg, and Pb | Phosphorous oxoacid compounds: Hypophosphite ($H_3PO_2$); Hypophosphoric acid ($H_4P_2O_6$); Isohypophosphoric acid ($H_4P_2O_6$); Phosphonic acid or phosphorus acid ($H_3PO_3$); Diphosphonic acid ($H_4P_2O_5$); Phosphinic acid or hypophosphorous acid ($H_3PO_2$). Sulfur oxoacid compounds: | | |
| Compounds of the form $X(NO_3)_3$ or $XO(NO_3)$, where X = Al, Cr, Mn, Fe, Co, Ni, Ga, As, Y, | Thiosulfuric acid ($H_2S_2O_3$); Dithionic acid ($H_2S_2O_6$); Polythionic acid ($H_2S_{n+2}O_6$); Sulfurous acid ($H_2SO_3$); | | |

-continued

| Oxidizing Agents | Reducing Agents | Additives | Product(s) |
| --- | --- | --- | --- |
| Nb, Rh, In, La, Tl, Bi, Ac, Ce, Pr, Nd, Steven Meyer, Eu, Gd, Tb, Dy, Ho, Er, Tm, Yb, Lu, U, and Pu Compounds of the form $X(NO_3)_4$ or $XO(NO_3)_2$, where X = Mn, Sn, Pd, Zr, Pb, Ce, Pr, Tb, Th, Pa, U and Pu. Halogen oxoacids: perhalic acid ($HOClO_3$, $HOBrO_3$, $HOIO_3$); halic acid ($HOClO_2$, $HOBrO_2$, $HOIO_2$); halous acid (HOClO, HOBrO, HOIO) | Disulfurous acid ($H_2S_2O_5$); Dithionous acid ($H_2S_2O_4$). | | |

The minerals prepared above may be used in a wide variety of applications. Examples of these applications may include, but are not limited to, use as pigments, phosphors, fluorescing agents, paint additives, synthetic gems, chromatography media, gas scrubber media, filtration media, bioseparation media, zeolites, catalysts, catalytic supports, ceramics, glasses, glass-ceramics, cements, electronic ceramics, piezoelectric ceramics, bioceramics, roofing granules, protective coatings, barnacle retardant coating, waste solidification, nuclear waste solidification, abrasives, polishing agents, polishing pastes, radiopharmaceuticals, medical imaging and diagnostics agents, drug delivery, excipients, tabletting excipients, bioactive dental and orthopaedic materials and bioactive coatings, composite fillers, composite additives, viscosity adjustment additives, paper finishing additives, optical coatings, glass coatings, optical filters, fertilizers, soil nutrient(s) additives.

Example 39

Porous Shaped Bodies of Calcium Phosphates

An aqueous solution of 17.02 g 50 wt % hypophosphorous acid, $H_3PO_2$ (Alfa/Aesar reagent #14142, CAS #6303-21-5), equivalent to 71.95 wt % $[PO_4]^{-3}$ was combined with 5.00 g deionized water to form a clear, colorless solution contained in a 250 ml Pyrex beaker. To this solution was added 45.70 g calcium nitrate tetrahydrate salt, $Ca(NO_3)_2 \cdot 4H_2O$ (ACS reagent, Aldrich Chemical Co., Inc. #23,712-4, CAS #13477-34-4), equivalent to 16.97 wt % Ca. The molar ratio of $[Ca]^{2+}/[PO_4]^{-3}$ in this mixture was 3/2 and the equivalent solids level [as $Ca_3(PO_4)_2$] was 29.53 wt %. Endothermic dissolution of the calcium nitrate tetrahydrate proceeded under ambient temperature conditions, eventually forming a homogeneous solution. The viscosity of this solution was water-like, despite the high salt concentration.

A piece of damp (as removed from the packaging) cellulose sponge (O-Cel-O™, 3M Home and Commercial Care Division, P.O. Box 33068, St. Paul. Minn. 55133), trimmed to a block approximately 1.5"×1.5"×2.0", was immersed in the calcium nitrate+hypophosphorous acid solution and kneaded (alternately compressed and decompressed) to fully imbibe the reactant solution into the sponge. The approximately 4.5 cubic inch sponge block (approximately 3.5 g), thoroughly saturated with reactant solution (liquid uptake approximately 7 to 8 times the virgin sponge weight), was placed on a platinum plate in a laboratory furnace (Vulcan model 3-550, NEYTECH, Inc., 1280 Blue Hills Ave., Bloomfield, Conn. 06002) that was preheated to 500° C. After several seconds, a reaction commenced at the surface of the sponge with the evolution of red-brown fumes characteristic of $NO_{x(g)}$. As the reaction proceeded from the surface to the interior of the sponge block, $NO_{x(g)}$ evolution continued and some reactant liquid exuded from the sponge and accumulated at the bottom of the Pt plate as a crusty white mass of solid. The cellulose sponge itself was consumed as the reaction progressed and the reactant mass attained the oven temperature. After thermal treatment at 500° C. for 45 minutes, the sample was removed from the lab furnace. The sample had been converted to an inorganic replica of the original organic sponge structure. The vestigial structure represented a positive version of the original sponge structure with faithful replication of the cellular elements, porosity, and macrostructure. The vestigial mass was mottled gray suggesting the presence of some residual carbon in the structure due to incomplete burnout of the combustion products from the cellulose sponge matrix. The vestigial mass was fragile with very low apparent density, but it was robust enough to be handled as a coherent block of highly porous solid once it was removed from the exudate material.

Figure 11:
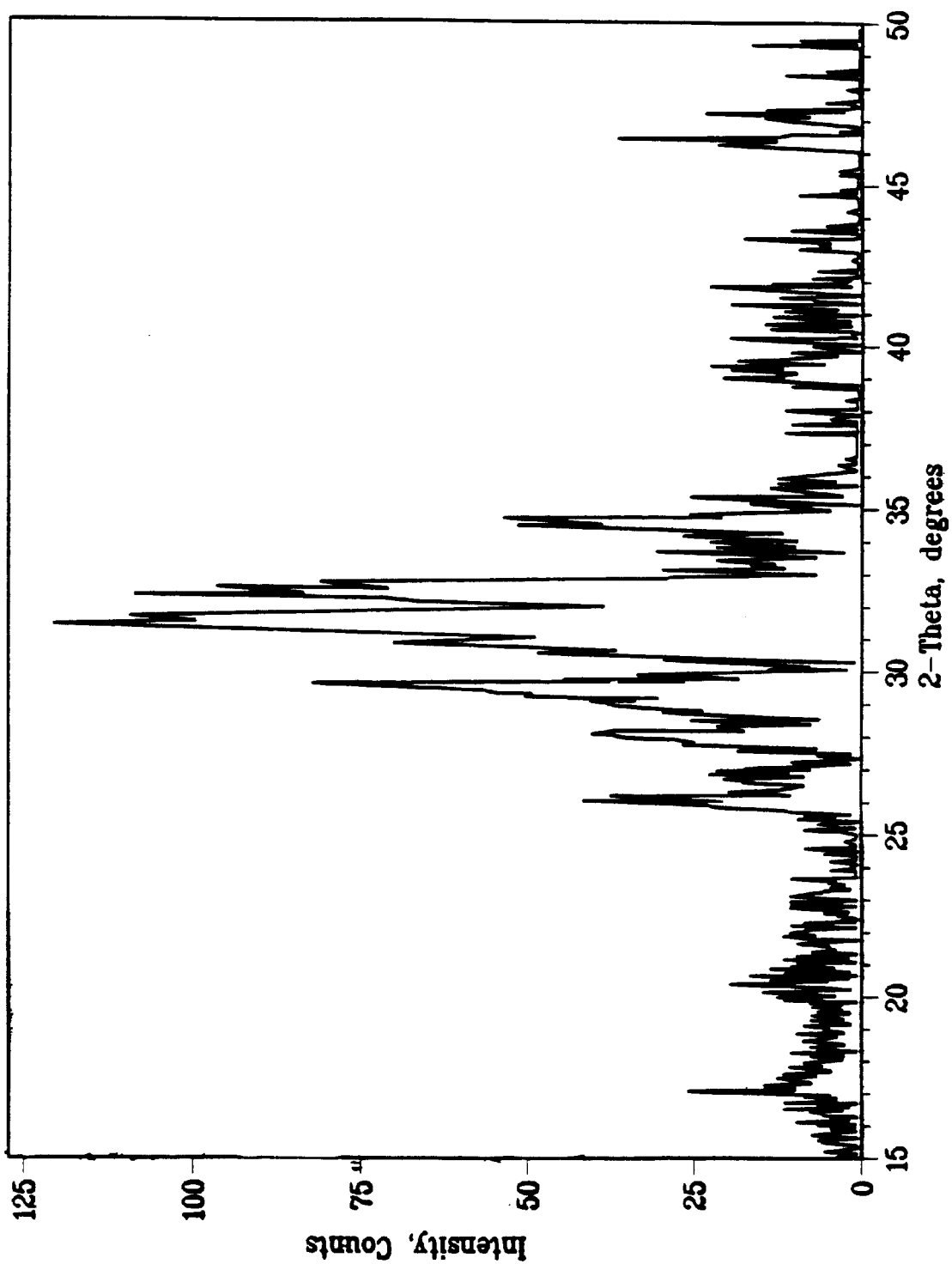
FIG. 11 is an X-ray diffraction (XRD) plot of a pulverized sample of porous calcium phosphate material fired at 500° C. in accordance with one embodiment of this invention. The sample consists of a biphasic mixture of whitlockite $Ca_3(PO_4)_2$ (PDF 09-0169) and hydroxyapatite $Ca_5(PO_4)_3(OH)$ (PDF 09-0432).

An X-ray diffraction (XRD) pattern was obtained from a packed powder sample of the inorganic sponge material pulverized in a mortar and pestle. The pattern was obtained using a Rigaku MiniFlex instrument (Rigaku/USA, Inc., Northwoods Business Park, 199 Rosewood Dr., Danvers, Mass. 01923) running JADE pattern processing software (Materials Data, Inc., P.O. Box 791, Livermore, Calif. 94551) using a 2 degree/minute scan rate over the 2 theta angular range from 15–50°. The XRD pattern for this material is shown in FIG. 11. Peak analysis indicated the solid to consist of whitlockite $Ca_3(PO_4)_2$ (PDF 09-0169) and hydroxyapatite $Ca_5(PO_4)_3(OH)$ (PDF 09-0432).

Figure 12:
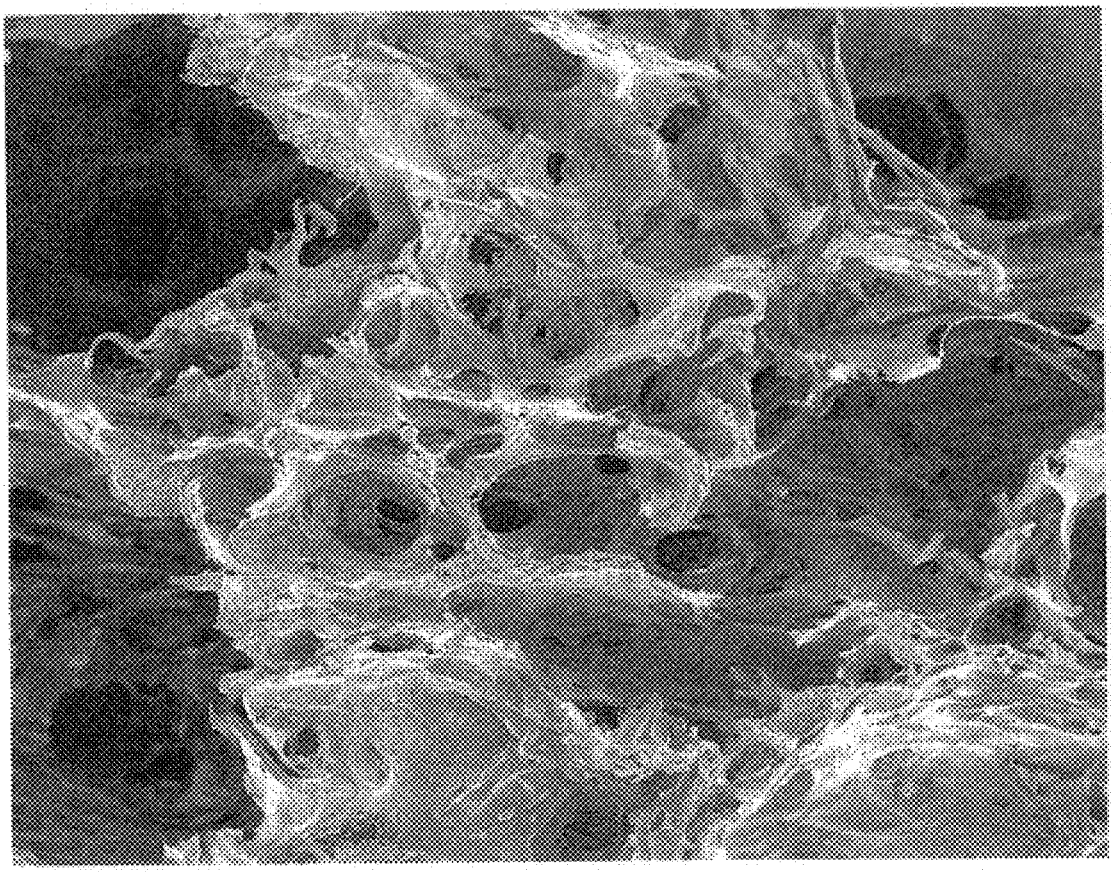
FIG. 12 is a 50×magnification scanning electron micrograph of a virgin cellulose sponge material used to prepare several of the embodiments of this invention.
Figure 13:
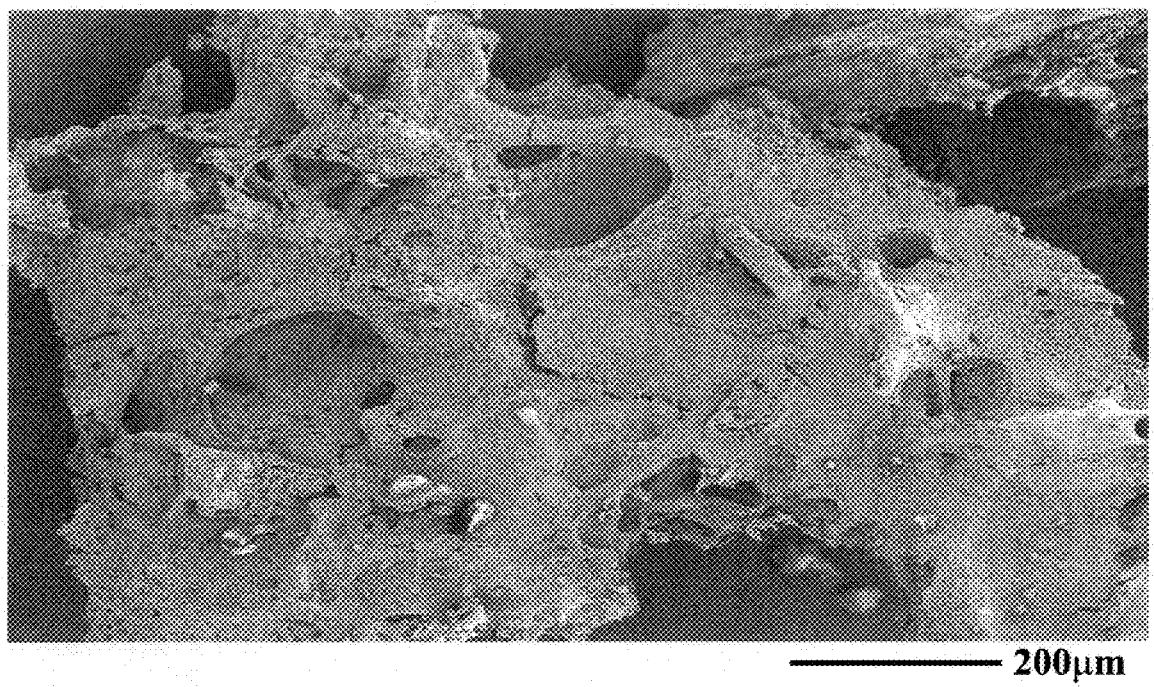
FIG. 13 is a 100×magnification scanning electron micrograph of porous calcium phosphate material fired at 500° C. in accordance with one embodiment of this invention.

A sample of the O-Cel-O™ cellulose sponge was prepared for scanning electron microscopy by sputter coating with Pt using a Hummer 6.2 Sputtering System (Anatech, Inc., 6621-F Electronic Drive, Springfield, Va. 22151). SEM examination was performed using a JEOL model JSM-840A microscope (JEOL USA, Inc., 11 Dearborn Road, P.O. Box 6043, Peabody, Mass. 01961). FIG. 12 shows a SEM image of the virgin cellulose sponge. FIG. 13 shows a SEM image of the calcium phosphate material prepared from the cellulose sponge.

Example 40

Transformed Shaped Bodies of Calcium Phosphate

Figure 14:
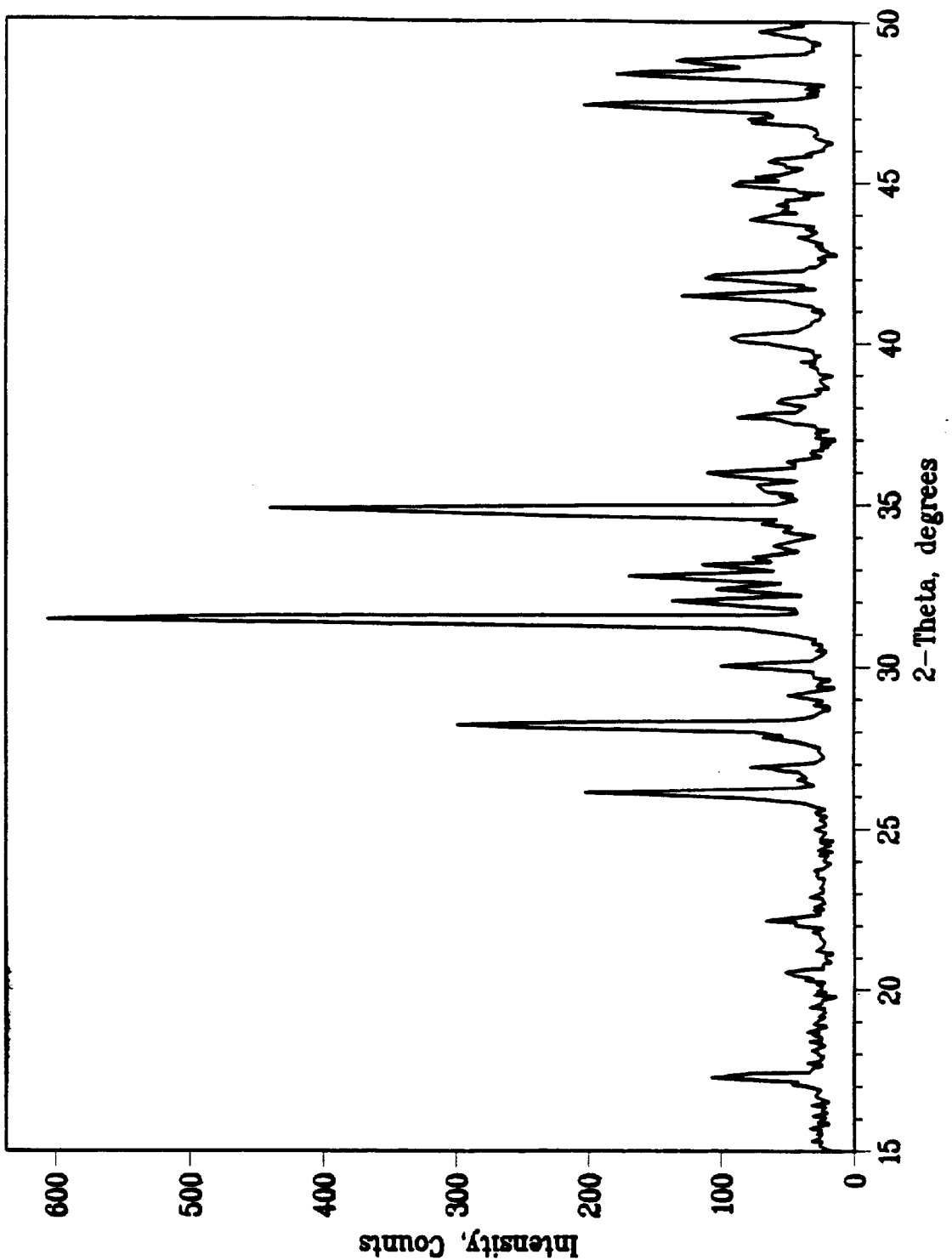
FIG. 14 is an X-ray diffraction (XRD) plot of a pulverized sample of porous calcium phosphate material fired at 1100° C. in accordance with one embodiment of this invention. The sample consists of whitlockite $Ca_3(PO_4)_2$ (PDF 09-0169).
Figure 15:
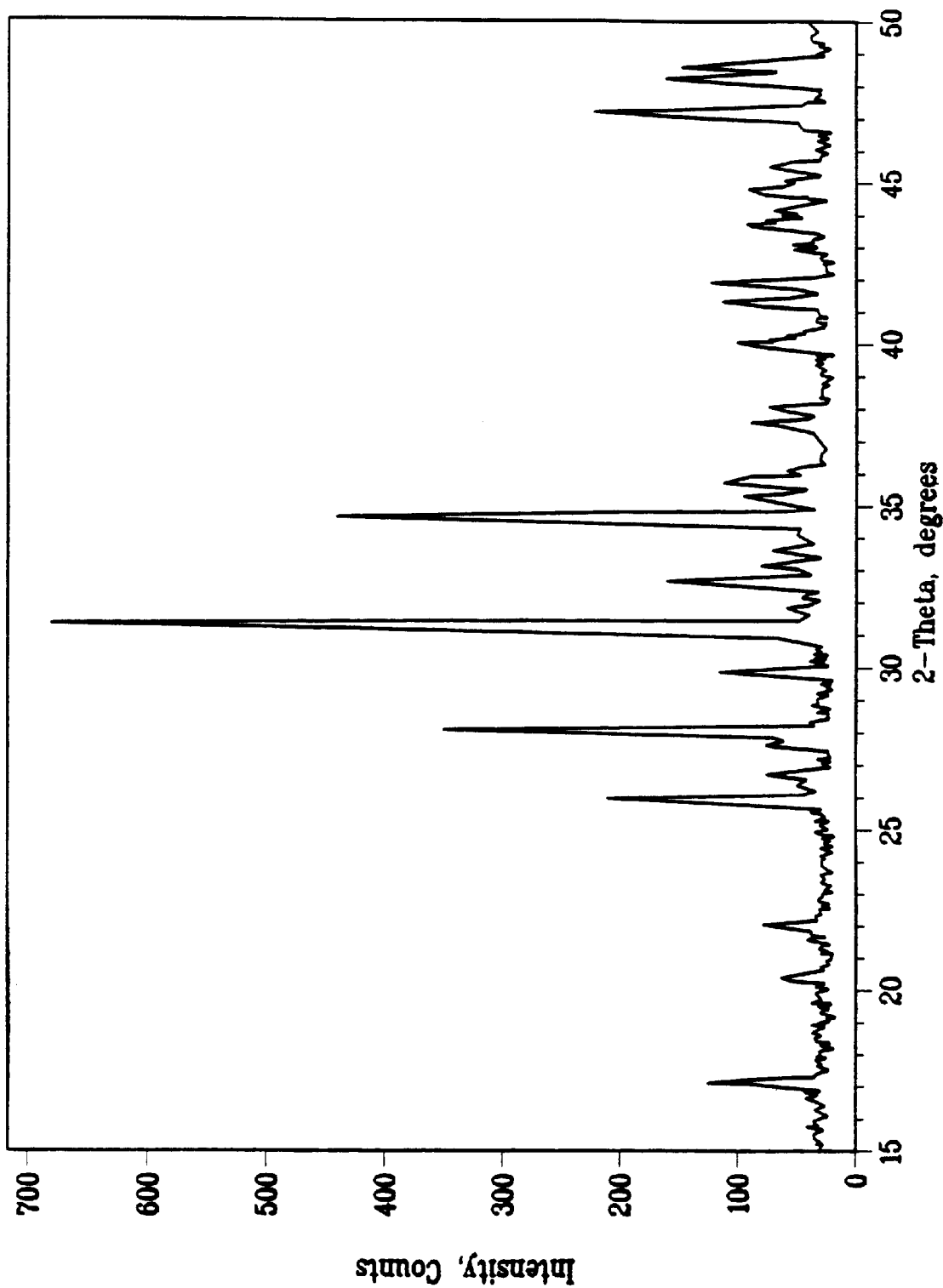
FIG. 15 is an X-ray diffraction (XRD) plot of a pulverized sample of porous calcium phosphate material fired at 1350° C. in accordance with one embodiment of this invention. The sample consists of whitlockite $Ca_3(PO_4)_2$ (PDF 09-0169).

The material from Example 39 was fired under a variety of conditions in order to (1) eliminate residual carbon from the structure and (2) attempt to promote sintering reactions in order to strengthen the inorganic sponge matrix. The samples were fired on Pt plates in a Lindberg model 51333 box furnace (Lindberg/Blue M, Inc., 304 Hart St., Watertown, Wis. 53094) equipped with a Lindberg series 59000 control console. The following table summarizes these results:

| Temp./time | | Observations | XRD |
|---|---|---|---|
| 900° C. | 15 minutes | Snow white mass | |
| 1000° C. | 1 hour | Snow white mass | |
| 1100° C. | 1 hour | Snow white mass | |
| 1100° C. | 13 hours | Snow white mass | Whitlockite (FIG. 14) |
| 1200° C. | 13 hours | Snow white mass | |
| 1350° C. | 1 hour | Snow white mass | Whitlockite (FIG. 15) |

A subjective assessment of the strength of these heat treated specimens showed no apparent changes. There was no indication that sintering occurred even at temperatures up to 1350° C.

Example 41

Shaped Bodies

Figure 16:
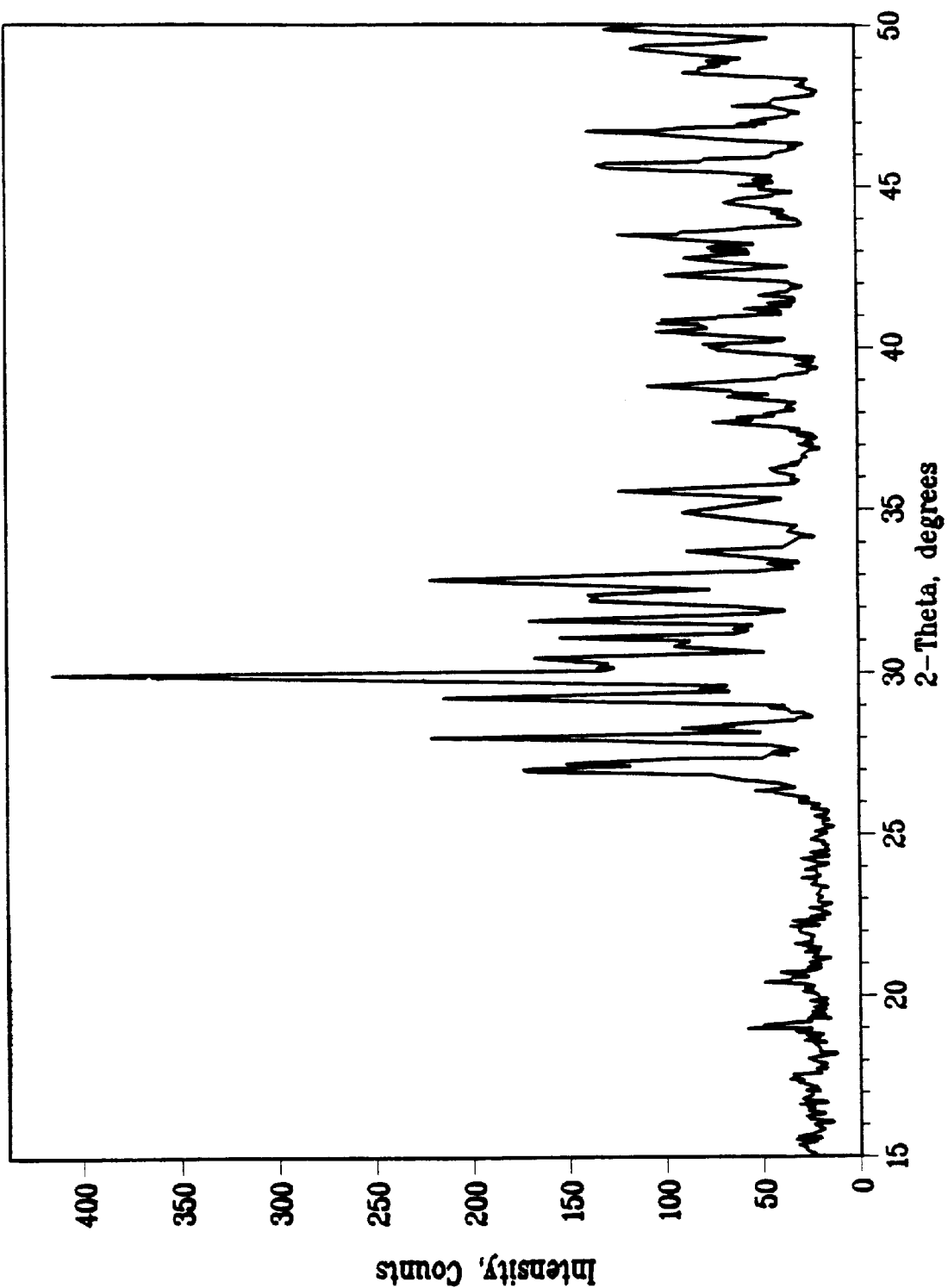
FIG. 16 is an X-ray diffraction (XRD) plot of a pulverized sample of porous calcium phosphate material fired at 800° C. in accordance with one embodiment of this invention. The sample consists of calcium pyrophosphate, $Ca_2P_2O_7$ (PDF 33-0297).

A solution was prepared as described in Example 39 using 9.70 g 50 wt % $H_3PO_2$, no deionized water, and 17.38 g $Ca(NO_3)_2 4H_2O$ to obtain a molar ratio of $[Ca]^{2+}/[PO_4]^{-3}$ of 1.0 and an equivalent solids level [as $CaHPO_4$] of 36.92 wt %. A small block of damp O-Cel-O™ sponge (as removed from the packaging) was fully imbibed with the reactant solution, set in a porcelain crucible, and placed into a Vulcan lab oven preheated to 500° C. After 1 hour at 500° C., the mottled gray sample was refired at 800° C. (Vulcan furnace) for 15 minutes. The final inorganic sponge sample was completely white indicating complete carbon burnout. An XRD pattern (FIG. 16) was obtained from a packed powder sample prepared as described in Example 39. Peak analysis indicated the solid to consist of calcium pyrophosphate, $Ca_2P_2O_7$ (PDF 33-0297).

Example 42

Shaped Bodies of Zinc Phosphate

An aqueous solution of 13.67 g 50 wt % $H_3PO_2$ was combined with 5.00 g deionized water to form a clear, colorless solution contained in a 250 ml Pyrex beaker. To this solution was added 46.23 g zinc nitrate hexahydrate salt, $Zn(NO_3)_2.6H_2O$ (Aldrich Chemical Co., Inc. #22,873-7, CAS #10196-18-6), equivalent to 21.97 wt. % Zn. The molar ratio of $[Zn]^{2+}/[PO_4]^{-3}$ in this mixture was 3/2 and the equivalent solids level [as $Zn_3(PO_4)_2$] was 27.5 wt. %.

Figure 17:
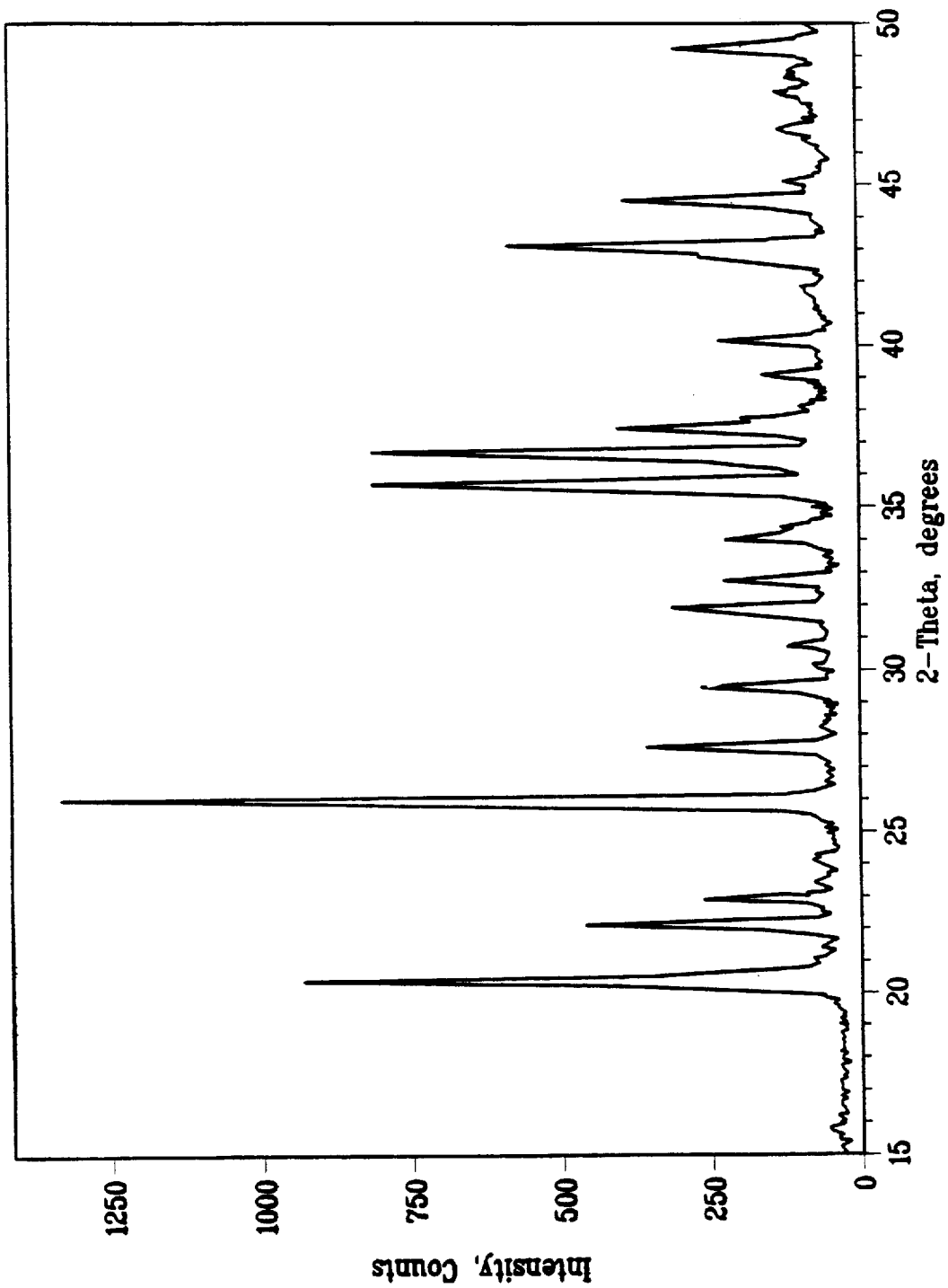
FIG. 17 is an X-ray diffraction (XRD) plot of a pulverized sample of porous zinc phosphate material fired at 500° C. in accordance with one embodiment of this invention. The sample consists of zinc phosphate, $Zn_3(PO_4)_2$ (PDF 30-1490).

Endothermic dissolution of the zinc nitrate hexahydrate proceeded under ambient temperature conditions, eventually forming a homogeneous solution. A block of O-Cel-O™ sponge was fully imbibed with this reactant solution as described in Example 39. The sample was first fired at 500° C. for 1 hour and then at 800° C. for 15 minutes. The inorganic sponge sample was light gray in color (due to residual carbon) and it was robust enough to be handled as a coherent block of low density, highly porous material. An XRD pattern (FIG. 17) was obtained from a packed powder sample prepared as described in Example 39. Peak analysis indicated the solid to consist of zinc phosphate, $Zn_3(PO_4)_2$ (PDF 30-1490).

Example 43

Neodymium Phosphate Bodies

Figure 18:
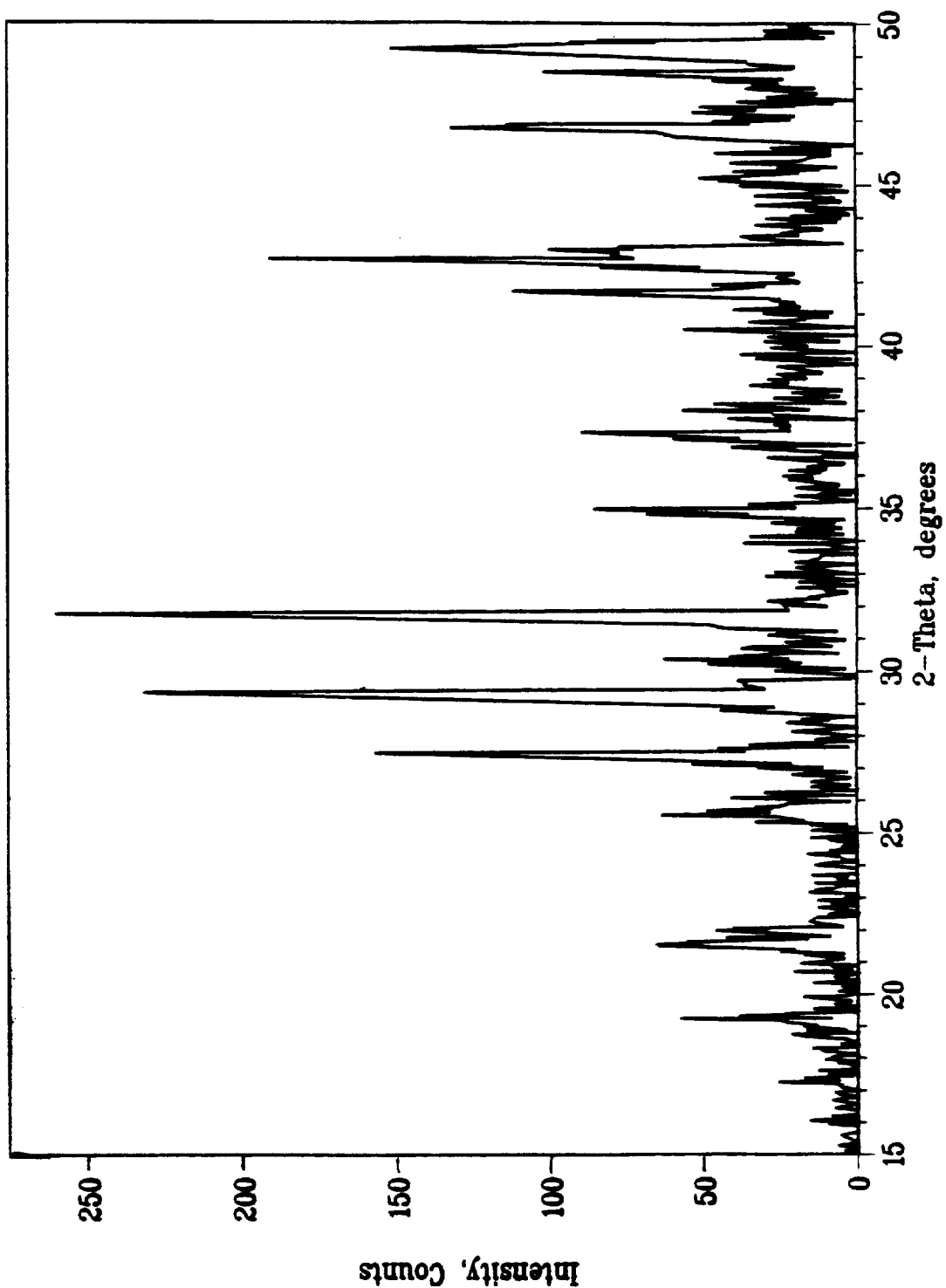
FIG. 18 is an X-ray diffraction (XRD) plot of a pulverized sample of porous neodymium phosphate material fired at 500° C. in accordance with one embodiment of this invention. The sample consists of neodymium phosphate, $NdPO_4$ (PDF 25-1065).

An aqueous solution of 11.04 g 50 wt % $H_3PO_2$ was combined with 5.00 g deionized water to form a clear, colorless solution contained in a 250 ml Pyrex beaker. To this solution was added 36.64 g neodymium nitrate hexahydrate salt, $Nd(NO_3)_3.6H_2O$ (Alfa/Aesar reagent #12912, CAS #16454-60-7), equivalent to 32.90 wt % Nd. Endothermic dissolution of the neodymium nitrate hexahydrate proceeded under ambient temperature conditions, eventually forming a pale lavender homogeneous solution. A block of O-Cel-O™ sponge was fully imbibed with this reactant solution as described in Example 39. The sample was first fired at 500° C. for 1 hour and then at 800° C. for 15 minutes. The inorganic sponge sample was pale lavender in color at the outside of the inorganic sponge mass and light gray in the interior (due to residual carbon). The inorganic sponge mass was very fragile, but it was robust enough to be handled as a coherent block of low density, highly porous material. An XRD pattern (FIG. 18) was obtained from a packed powder sample prepared as described in Example 39. Peak analysis indicated the solid to consist of neodymium phosphate, $NdPO_4$ (PDF 25-1065).

Example 44

Aluminium Phosphate Bodies

Figure 19:
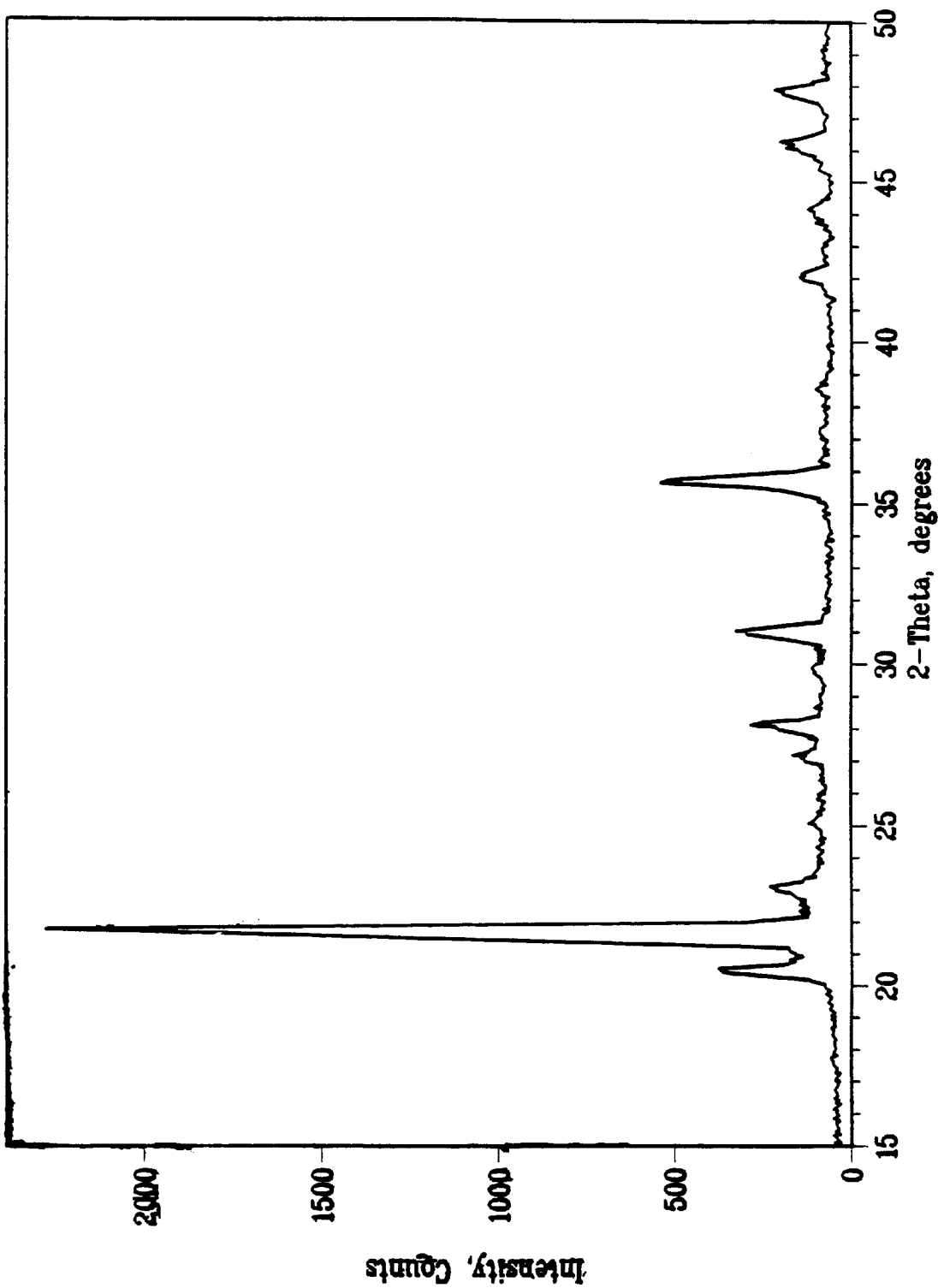
FIG. 19 is an X-ray diffraction (XRD) plot of a pulverized sample of porous aluminum phosphate material fired at 500° C. in accordance with one embodiment of this invention. The sample consists of aluminum phosphate, $AlPO_4$ (PDF 11-0500).

An aqueous solution of 21.65 g 50 wt % $H_3PO_2$ was combined with 5.00 g deionized water to form a clear, colorless solution contained in a 250 ml Pyrex beaker. To this solution was added 61.56 g aluminum nitrate nonahydrate salt, $Al(NO_3)_3.9H_2O$ (Alfa/Aesar reagent #36291, CAS #7784-27-2), equivalent to 7.19 wt. % Al. Endothermic dissolution of the aluminum nitrate hexahydrate proceeded under ambient temperature conditions, eventually forming a homogeneous solution. A block of O-Cel-O™ sponge was fully imbibed with this reactant solution as described in Example 39. The sample was first fired at 500° C. for 1 hour and then at 800° C. for 15 minutes. The inorganic sponge sample was white at the outside of the inorganic sponge mass and light gray in the interior (due to residual carbon). The inorganic sponge mass could be handled as a coherent block of low density, highly porous material. An XRD pattern (FIG. 19) was obtained from a packed powder sample prepared as described in Example 39. Peak analysis indicated the solid to consist of aluminum phosphate, $AlPO_4$ (PDF 11-0500).

Example 45

Modified Porous Structures

A piece of the inorganic sponge material from Example 39 was immersed in molten paraffin wax (CAS #8002-74-2) (Northland Canning Wax, Conros Corp., Detroit, Mich. 48209) maintained at >80° C. so as to imbibe the porous structure. The inorganic sponge, wetted with molten wax, was removed from the molten wax and allowed to cool at room temperature. The wax solidified on cooling and imparted additional strength and improved handling properties to the inorganic sponge material such that the paraffin wax-treated material could be cut and shaped with a knife. Most of the formerly open porosity of the inorganic sponge material was filled with solidified paraffin wax.

Example 46

Gelatin Modification

A piece of the inorganic sponge material from Example 39 was immersed in a solution prepared by dissolving 7.1 g food-grade gelatin (CAS #9000-70-0) (Knox Unflavored Gelatin, Nabisco Inc., East Hanover, N.J. 07936) in 100.0 g deionized water at approximately 90° C. The inorganic sponge material readily imbibed the warm gelatin solution and, after several minutes, the largely intact piece of inorganic sponge material was carefully removed from the solution and allowed to cool and dry overnight at room temperature. The gelatin solution gelled on cooling (bloom strength unknown) and imparted additional strength and improved handling properties to the inorganic sponge material. Although no pH or electrolyte/nonelectrolyte concentration adjustments were made to the system described in this example, it is anticipated that such adjustments away from the isoelectric point of the gelatin would impart additional rigidity to the gelatin gel and, thereby, to the gelatin-treated inorganic sponge material. Significant additional strength and improved handling properties were noted in the gelatin-treated inorganic sponge material after the gelatin was allowed to thoroughly dry for several days at room temperature. Some shrinkage of the gelatin-treated inorganic sponge materials was noted on drying. The shrinkage was nonuniform with the greatest contraction noted near the center of the body. This central region was, of course, the last area to dry and, as such, was surrounded by hardened inorganic sponge material which could not readily conform to the contraction of the core as it dehydrated. The material exhibited considerable improvement in compression strength and a dramatically reduced tendency to shed particulate debris when cut with a knife or fine-toothed saw. It is presumed that the film-forming tendency of the gelatin on drying induced compressive forces on the internal cellular elements of the inorganic sponge material, thereby strengthening the overall structure.

Cylindrical plugs could be cored from pieces of the air dried gelatin-treated inorganic sponge material using hollow punch tools ranging from ½ inch down to ⅛ inch in diameter.

Figure 20:
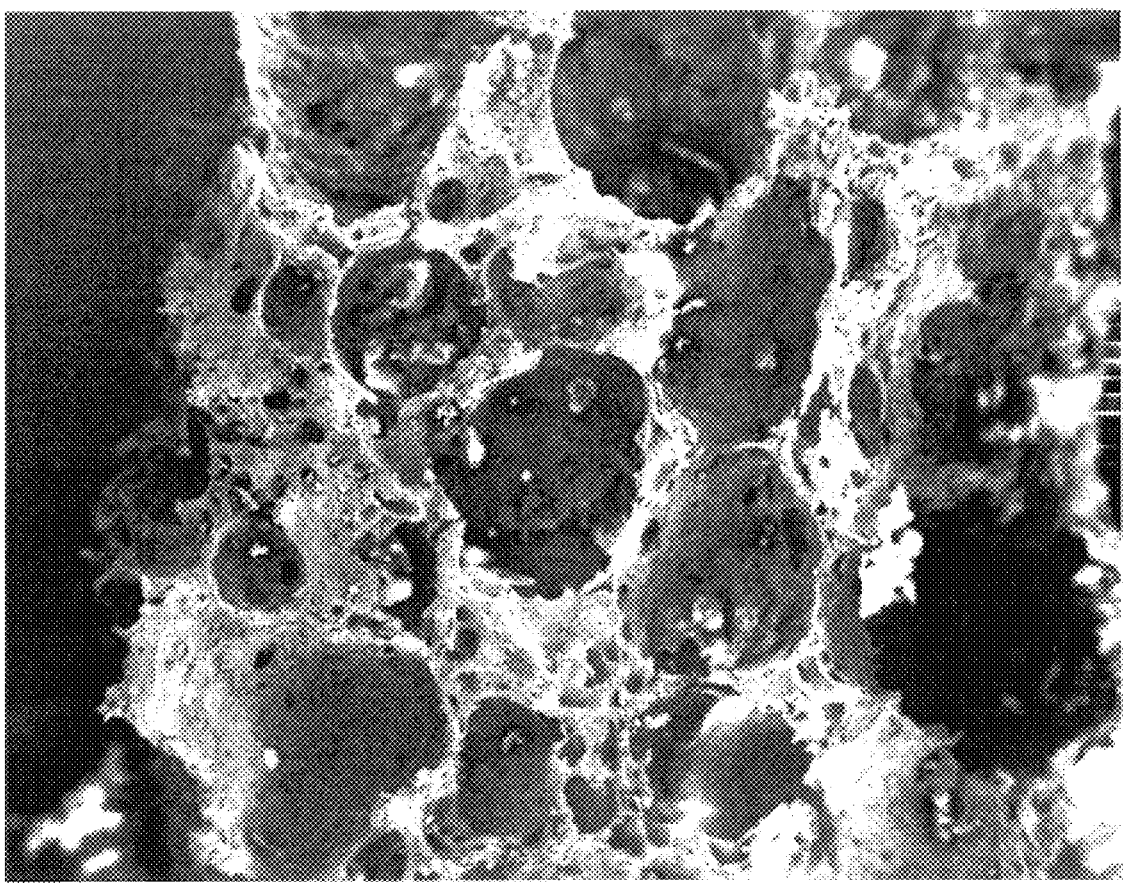
FIG. 20 is a 23×magnification scanning electron micrograph depicting the macro- and meso-porosity of porous calcium phosphate material fired at 500° C. and reinforced with gelatin in accordance with one embodiment of this invention.
Figure 21:
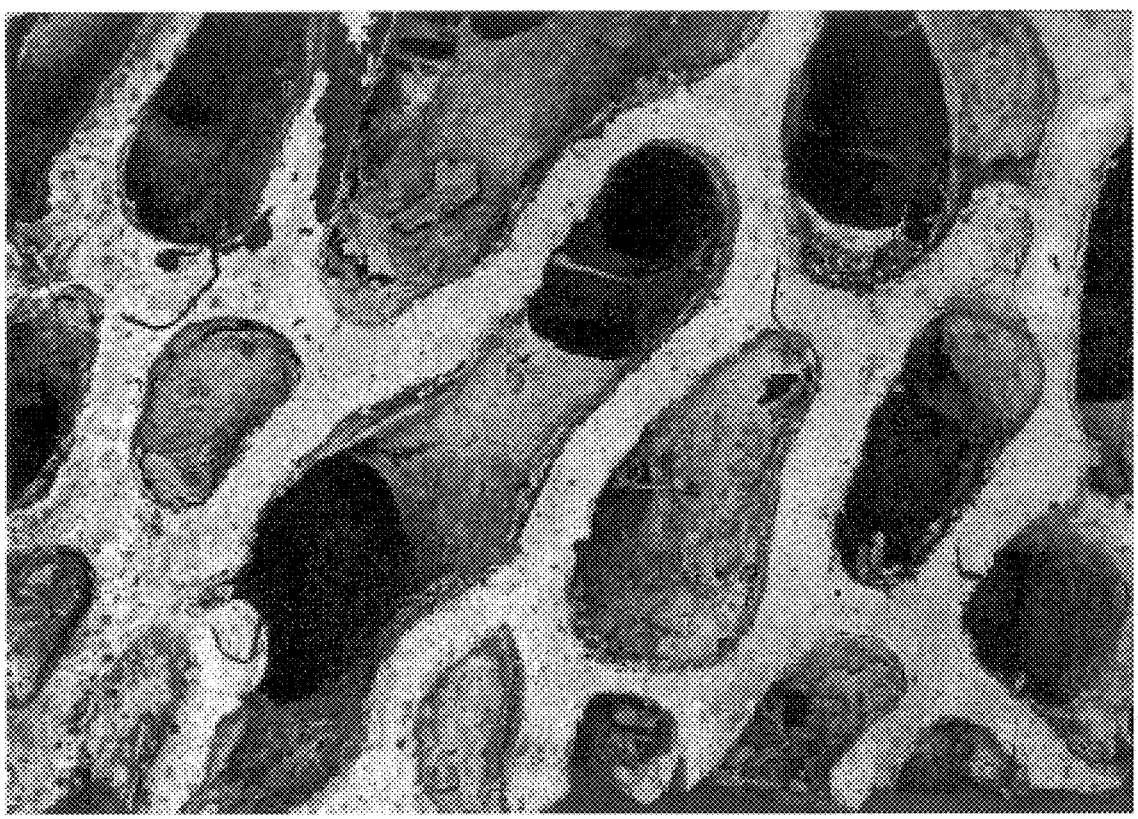
FIG. 21 is a 25×magnification scanning electron micrograph of sheep trabecular bone for comparative purposes.
Figure 22:
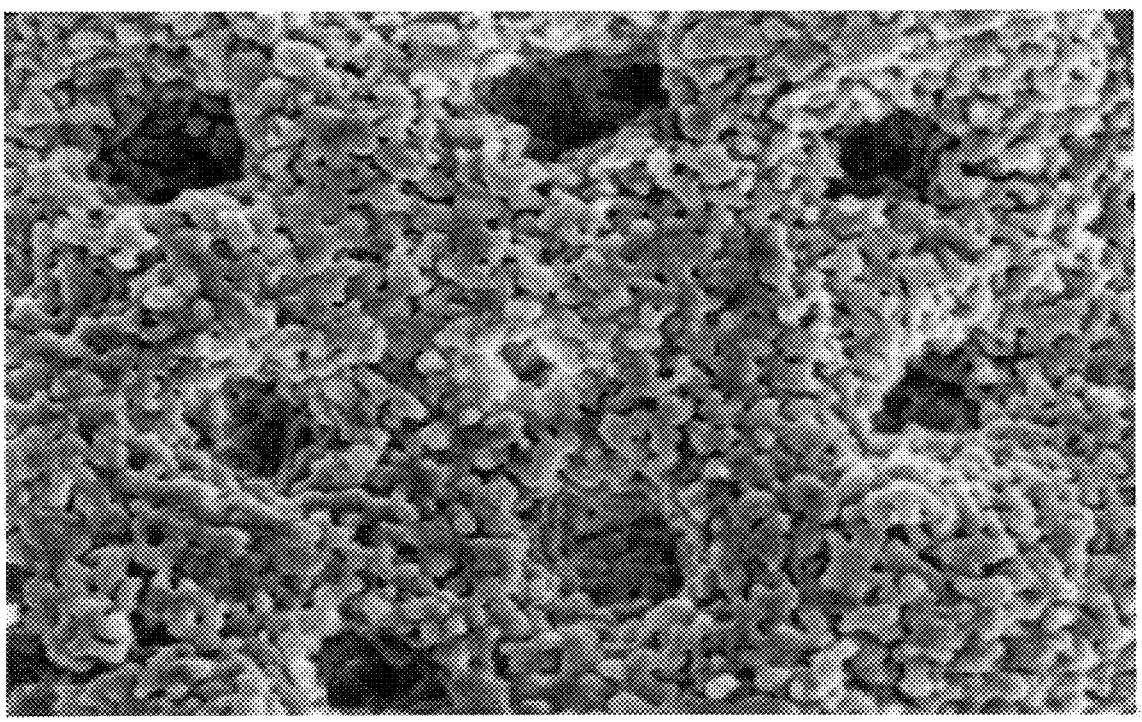
FIG. 22 is a 2000×magnification scanning electron micrograph of the air-dried gelatin treated inorganic sponge depicted in FIG. 20 which exhibits meso- and microporosity in the calcium phosphate matrix.

FIG. 20 is a SEM of the air-dried gelatin treated inorganic sponge, which was prepared as described in Example 39. A comparison of this SEM with that of the initial cellulose sponge material (FIG. 12) shows how faithfully the sponge micro- and macrostructure has been replicated in the inorganic sponge material. FIG. 21 is a SEM of sheep trabecular bone. The highly porous macrostructure of sheep trabecular bone is representative of the anatomical structure of cancellous bone of higher mammals, including humans. The sample of sheep trabecular bone was prepared for SEM analysis by sputter coating (as described in Example 39) a cross-sectional cut from a desiccated sheep humerus. FIG. 22 is a higher magnification SEM of the air-dried gelatin treated inorganic sponge depicted in FIG. 20. From this SEM micrograph, the presence of meso- and microporosity in the calcium phosphate matrix is readily apparent.

Example 47

Implant Cages

A rectangular block approximately ¼ inch×½ inch x 3/4 inch was cut from a piece of damp (as removed from the packaging) O-Cel-O™ cellulose sponge. This sponge piece was trimmed as necessary so to completely fill the internal cavity of a titanium nitride (TiN)-coated box-like spinal implant cage (Stratech Medical, Inc.). The sponge insert was intentionally made slightly oversized to ensure good fit and retention in the cage assembly. The cellulose sponge block was fully imbibed with a reactant solution prepared as described in Example 39. The solution-saturated sponge insert was then inserted through the open side of the spinal cage assembly and manipulated to completely fill the interior cavity of the implant assembly. Despite the compliance of the solution-saturated sponge, there was almost no penetration of the sponge into the fenestrations of the implant. The sponge-filled cage assembly, sitting on a Pt plate, was placed in a laboratory oven preheated to 500° C. and held at that temperature for 1 hour. After cooling to room temperature, the implant assembly was removed from the small amount of crusty white solid resulting from reactant solution which had exuded from the sponge insert and coated the surface of the implant. The TiN coating on the cage appeared unaffected by the treatment, and the internal chamber was filled with inorganic sponge material having a mottled gray appearance. The filled cage assembly was refired at 800° C. for 30 minutes in an attempt to eliminate residual carbon from the inorganic sponge material. After cooling, examination of the implant assembly revealed that the TiN coating had been lost via oxidation, while the inorganic sponge material was completely white. There was excellent retention of the inorganic sponge material in the chamber of the spinal cage assembly.

Example 48

Orthopaedic Implants

Two cylindrical plugs of approximately ⅜ inch diameter and ½ inch length were cut from a piece of damp (as removed from the packaging) Marquis™ cellulose sponge (distributed by Fleming Companies, Inc., Oklahoma City, Okla. 73126) using a hollow punch (Michigan Industrial Tools, P.O. Box 88248, Kentwood, Mich. 49518) of the appropriate size. These cellulose sponge plugs were then trimmed to the necessary length so to completely fill the bicompartmental central cavity of a 13 mm×20 mm (diameter×length) BAK threaded cylindrical interbody implant (SpineTech, Inc., 7375 Bush Lake Road, Minneapolis, Minn. 55439). The plugs were intentionally made slightly oversized to ensure good fit and retention in the two chambers of the titanium spinal fusion cage assembly. The cylindrical sponge plugs were fully imbibed with a reactant solution prepared as described in Example 39 and the solution saturated sponge plugs were inserted through the open ends of the spinal cage assembly and manipulated to completely fill both of the internal chambers of the implant assembly. Despite the compliance of the solution-saturated sponge, there was almost no penetration of the sponge into the fenestrations of the implant. The sponge-filled cage assembly sitting on a Pt plate was placed in a laboratory oven preheated to 200° C. Immediately, a temperature ramp to 500° C. was begun (duration of 16 minutes) followed by a 30 minute hold at 500°. After cooling to room temperature, the implant assembly was removed from the small amount of crusty white solid resulting from reactant solution which had exuded from the sponge pieces and coated the surface of the implant. The titanium cage appeared unaffected by the treatment, and the chambers were filled with inorganic sponge material having a mottled gray appearance. The filled cage assembly was refired at 700° C. for 10 minutes in an attempt to eliminate residual carbon from the inorganic sponge material. After cooling, examination of the implant assembly revealed that the surface of the titanium cage appeared to have undergone some oxidation as evidenced by its roughened texture, while the inorganic sponge material was white at the surface but still gray at the center of the mass. Obviously, further heat treatment would be necessary to fully oxidize the residual carbon in the interior of the inorganic sponge masses in each chamber of the implant assembly. There was excellent retention of the inorganic sponge material in both of the chambers of the spinal cage assembly.

Example 49

Sterilization

Samples of gelatin-treated inorganic sponge material were prepared as described in Example 46 and allowed to thoroughly dry at room temperature for longer than one week. Pieces of this dry gelatin-treated material were subjected to prolonged oven treatments in an air atmosphere within a Vulcan model 3-550 oven (see Example 39) to simulate conditions typically encountered in "dry heat" sterilization procedures. The these experiments:

| Temperature (° C.) | Time (h) | Observations |
|---|---|---|
| 130 | 3 | No color change |
| 130 | 6 | Very slight yellowing |
| 130 | 15 | Very slight yellowing |
| 150 | 4 | Very slight yellowing |
| 170 | 1 | Very slight yellowing |
| 170 | 3.5 | Pale yellow at surface, white interior |

It was assumed that temperature equilibration between the samples and the oven was rapidly attained due to the significant porosity and low thermal mass of the materials. Clearly, there was no significant degradation of the gelatin under these heat treatment regimens. Furthermore, a subjective assessment of the strength of these dry heat treated specimens showed no apparent changes.

Example 50

Template Residues

A block of damp (as removed from the packaging) O-Cel-O™ brand cellulose sponge with a weight of 7.374 g, setting on a platinum plate, was placed into a Vulcan model 3-550 oven preheated to 500° C. and held at that temperature for 1 hour. At the conclusion of the burnout cycle, 0.073 g of fluffy gray ash was collected representing approximately 0.99 wt % of the original cellulose sponge mass.

Figure 23:
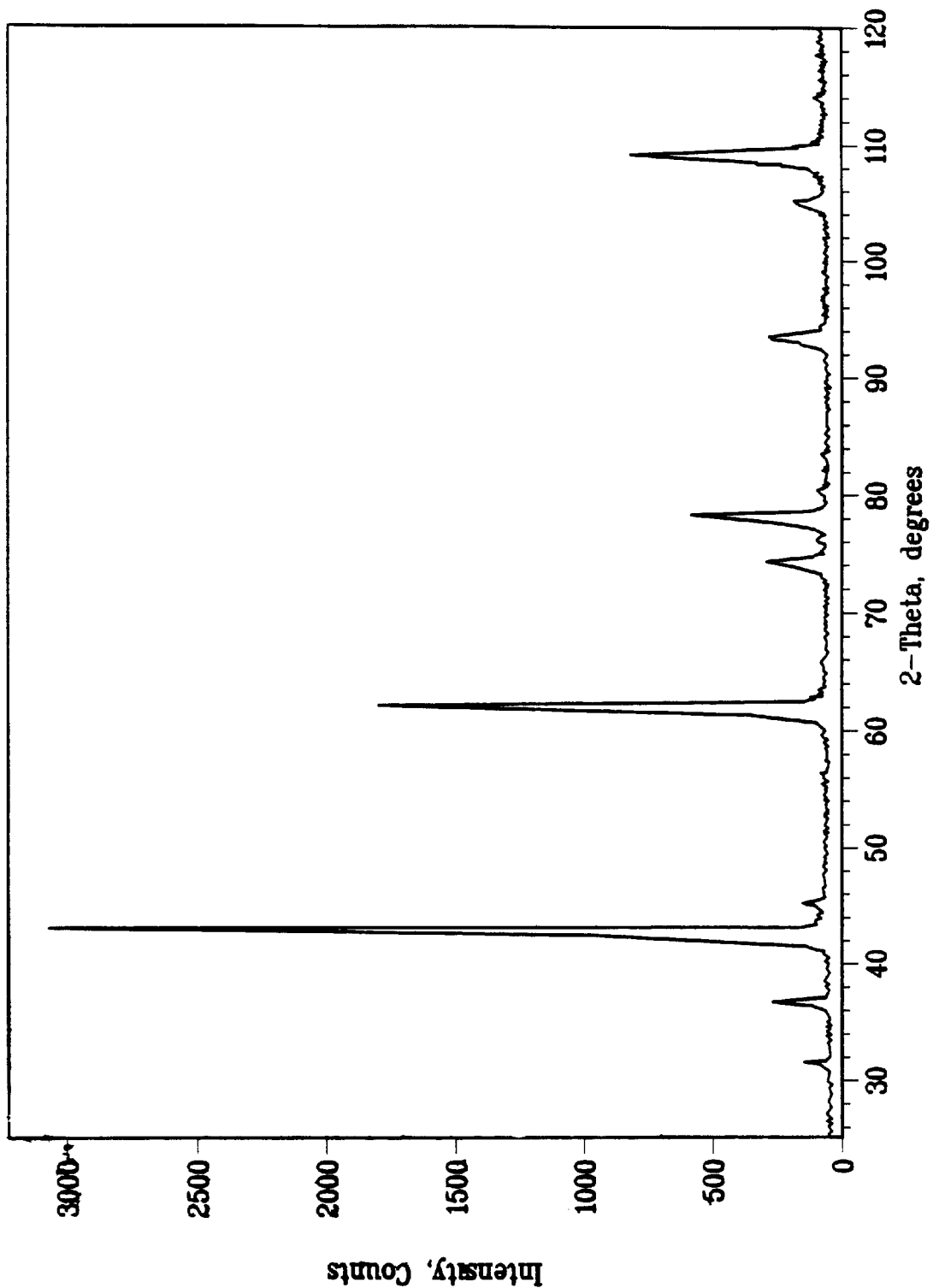
FIG. 23 is an X-ray diffraction (XRD) plot of a pulverized sample of the ash remaining after firing at 500° C. of the virgin cellulose sponge starting material used to prepare several of the embodiments of this invention. The ash sample consists of a biphasic mixture of magnesium oxide, MgO (major) (PDF 45-0946) and sodium chloride, NaCl (minor) (PDF 05-0628).

A block of damp (as removed from the packaging) Marquis™ brand cellulose sponge with a weight of 31.089 g, setting on a platinum plate, was placed into a Vulcan model 3-550 oven preheated to 500° C. and held at that temperature for 1 hour. At the conclusion of the burnout cycle, 1.84 g of fluffy gray ash was collected representing approximately 5.9 wt % of the original cellulose sponge mass. An XRD pattern obtained from this ash residue (FIG. 23) indicated the simultaneous presence of magnesium oxide, MgO (major) (PDF 45-0946) and sodium chloride, NaCl (minor) (PDF 05-0628) both phases resulting from the corresponding chloride salts used in the manufacturing process of the cellulose sponge. The presence of these two salts, in particular the MgO, may account for the "incomplete" burnout of the inorganic sponge material at 500 to 800° C. as noted in Examples 39, 41–44, 47, and 48.

Another block of the Marquis™ brand cellulose sponge was extensively washed in deionized water by repetitive kneading and multiple water exchanges. This thoroughly washed sponge was allowed to dry in air at room temperature for two days, after which it was cut into two blocks. The density of the washed and air-dried sponge comprising each of these two blocks was calculated to be approximately 1.03 g/inch$^3$. Each of these blocks of washed and air dried sponge was burned out according to the aforementioned procedure. An insignificant amount of ash was collected from each sample, indicating the efficacy of the washing procedure for removing salt contaminants.

Example 51

Alternative Templates

A reactant solution was prepared as described in Example 39. A variety of shapes, including disks, squares, and triangles, were cut from a sheet of 3/32 inch thick "Normandy compressed sponge" (Spontex, Inc., P.O. Box 561, Santa Fe Pike, Columbia, Tenn. 38402) using either scissors or hollow punches. This compressed cellulose sponge is manufactured to have a smaller median pore size and a narrower pore size distribution than either of the commercially available household sponges (O-Cel-O™ or Marquis™) used in Examples 39–50. This compressed sponge also has low ash levels (<0.1 wt % when burned out according to the procedure mentioned in Example 50) indicating that it is washed essentially free of salts during fabrication. The sponge is compressed into a sheet which, upon rewetting, expands to restore the original cellular sponge structure which, in the case of this particular example, is approximately 1 inch thick. Imbibation of water into the compressed sponge to saturation levels results in a weight increase of approximately 28 times over the dry sponge weight. The cut pieces of compressed sponge were fully imbibed with the reactant solution after which they swelled to form cylinders, cubes, and wedges. These solution saturated sponge articles, setting on Pt plates, were placed into a Vulcan model 3-550 oven preheated to 500° C. and held at that temperature for 1 hour. After cooling, the inorganic sponge pieces were carefully removed from the considerable amount of crusty white solid resulting from the exudate material. All samples had been converted to an inorganic replica of the original organic sponge structures. The vestigial structures represented positive versions of the original sponge structures with faithful replication of the cellular elements and porosity. The vestigial masses were fragile with very low apparent density, but they were robust enough to be handled as coherent blocks of highly porous solid once they were removed from the exudate material. The inorganic sponge material was mottled gray, suggesting the presence of some residual carbon in the structure. After refiring the samples at 800° C. (Vulcan furnace) for 15 minutes, the final inorganic sponge samples were completely white. The integrity of the various samples made from the controlled porosity cellulose sponge was improved over corresponding samples prepared from the commercial cellulose sponge materials.

Figure 24:
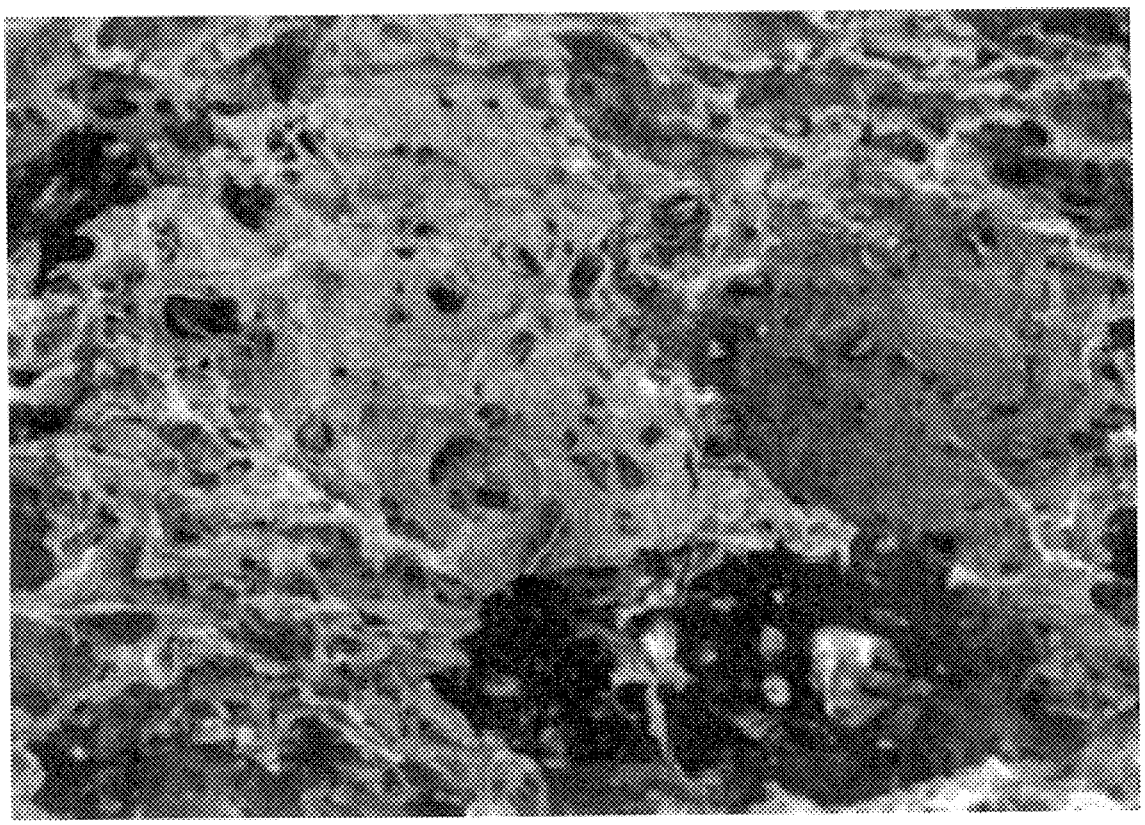
FIG. 24 is a 20×magnification scanning electron micrograph of a virgin cellulose sponge starting material, expanded from its compressed state, used to prepare several of the embodiments of this invention.

FIG. 24 is a SEM of the Normandy compressed sponge expanded in deionized water and prepared for microscopy as described in Example 39.

Example 52

Modified Templates

Pieces of the inorganic sponge material from Example 51 were immersed in a gelatin solution prepared as described in Example 46 except that 7.1 g of Knox gelatin was dissolved in 200 g deionized water rather than 100 g of deionized water. The inorganic sponge material readily imbibed the warm gelatin solution and, after several minutes, the largely intact pieces of inorganic sponge material were carefully removed from the solution and allowed to cool and dry at room temperature. Significant additional strength and improved handling properties were noted in the gelatin-treated inorganic sponge material after the gelatin was allowed to thoroughly dry for several days. The material exhibited considerable improvement in compression strength and a dramatically reduced tendency to shed particulate debris when cut with a knife or fine-toothed saw.

Several pieces of gelatin treated sponge which had been drying in air for >1 week were subjected to a burnout of the organic material at 800° C. (Vulcan furnace) for 30 minutes. The snow white inorganic sponge samples were weighed after firing and it was determined that the level of gelatin in the treated samples was 13.8+/−1.0 wt % (with respect to the inorganic sponge material).

Figure 25:
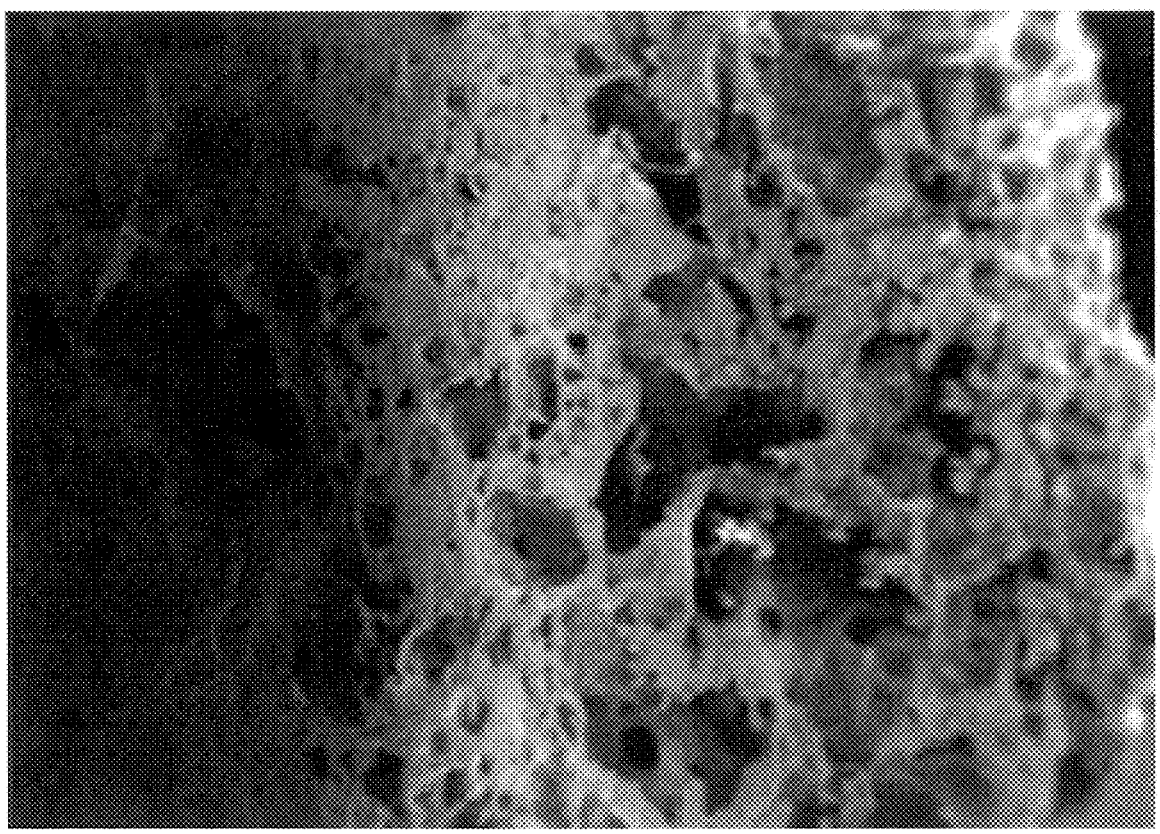
FIG. 25 is a 20×magnification scanning electron micrograph of porous calcium phosphate material fired at 800° C. and reinforced with gelatin in accordance with one embodiment of this invention.

FIG. 25 is a SEM of the air-dried gelatin treated inorganic sponge which was prepared as described above. A comparison of this SEM with that of the initial cellulose sponge material (FIG. 24) shows how faithfully the sponge micro- and macrostructure has been replicated in the polymer coated inorganic sponge material.

Example 53

Rewetting

Several pieces of air-dried gelatin-treated inorganic sponge material from Example 46 were placed in deionized water to assess the rewetting/rehydration behavior. Initially, the pieces floated at the water surface but, after approximately 2 hours, the sponge pieces began to float lower in the water indicating liquid uptake. After 24 hours, the samples were still floating, but >50% of the sponge volume was below the liquid surface. After 48 hours, the inorganic sponge samples were completely submerged suggesting complete rehydration of the gelatin and complete water ingress into the structure via interconnected porosity.

Example 54

Shaped Calcium Phosphates

Several pieces of the inorganic sponge material from Example 39 were immersed in a 50 wt % solution of disodium glycerophosphate hydrate prepared by dissolving 10.0 g $C_3H_7O_6PNa_2$ (Sigma Chemical Co. reagent G-6501, CAS #154804-51-0), equivalent to 65.25 wt % as "$Na_2PO_4$", in 10.0 g deionized water. The inorganic sponge material readily imbibed the disodium glycerophosphate solution and, after several minutes, the largely intact pieces of saturated inorganic sponge material were carefully removed from the solution. The wetted pieces, setting on a Pt plate, were placed in a Vulcan model 3-550 oven preheated to 150° C. Immediately, a temperature ramp to 850° C. was begun (duration of 50 minutes) followed by a 60 minute hold at 850° C. After cooling to room temperature, the surface of the treated inorganic sponge material had a glassy appearance, and significant additional strength and improved handling properties were noted. Upon examination of the pieces with a Leica zoom stereo microscope, the presence of a glassy surface was confirmed and rounding of the features was evident indicating that some level of sintering had occurred. Considerable shrinkage of the pieces was also noted.

An XRD pattern was obtained from a packed powder sample prepared as described in Example 39. Peak analysis indicated the solid to consist, in part, of Buchwaldite, sodium calcium phosphate, $NaCaPO_4$ (PDF 29-1193 and 29-1194).

Example 55

Discoid Bodies

A reactant solution was prepared as described in Example 39. Disks were cut from a sheet of 3/32 inch thick Normandy compressed sponge using a 3/8 inch diameter hollow punch and a model no. 3393 Carver hydraulic press (Carver Inc., 1569 Morris St., P.O. Box 544, Wabash, Ind. 46992) to ensure uniform sizing. The disks were distended by immersion in deionized water and the resulting sponge cylinders, each approximately 3/8 inch diameter by 1 inch length, were then blotted on paper towel to remove as much excess water as possible. The damp sponge cylinders were then imbibed with approximately seven times their weight of the reactant liquid. Nine of the solution imbibed pieces were placed horizontally and spaced uniformly in a 100×20 mm Pyrex petri dish. Two petri dishes, containing a total of 18 imbibed sponge cylinders, were positioned in the center of the cavity of a microwave oven (Hotpoint model no. RE963-001, Louisville, Ky. 40225) and the samples were irradiated at full power for a total of two minutes. After 30 seconds of exposure, the microwave oven cavity was full of NOx(g) and the reactant liquid which had exuded from the sponge cylinders had reacted/dehydrated to form a crusty white deposit in the petri dishes. The oven was opened to vent the cavity, then full power irradiation was resumed. After another 30 seconds of exposure, the oven cavity was again full of $NO_x(g)$ and steam. After venting the cavity once more, full power exposure was resumed for an additional 60 seconds, after which the fully dry sponge cylinders were removed. The sponge cylinders retained the orange color of the original cellulose material and a considerable fraction of the pores were filled with white solid. The pieces were very robust at this point, there was little or no warpage or slumping, and they could be handled and even abraded to shape the pieces and to remove asperities and any adherent solid resulting from the exuded liquid. The dried, solid-filled cylindrical sponge pieces were arrayed in a rectangular alumina crucible (2½" W×6" L×½" D) and placed in a furnace preheated to 500° C. The furnace temperature was ramped at 40° C./minute to 800° C. and held at 800° C. for 45 minutes. The resultant cylindrical white porous inorganic sponge samples were robust and exhibited strengths qualitatively similar to those attained from the fully dried gelatin-treated samples prepared as described in Example 52.

An XRD pattern was obtained from a packed powder sample prepared from the material fired at 800° C. Peak analysis indicated the solid to consist solely of whitlockite, beta-$Ca_3(PO_4)_2$ (PDF 09-0169).

Example 56

Implantation of Calcium Phosphate Shaped Plug into Canine Metaphyseal Bone

The porous calcium phosphate scaffolds, prepared as described in Example 55, are instantly wetted by water, aqueous solutions, alcohols, and other hydrophilic liquids in distinct contrast to the gradual rewetting of the gelatin-treated scaffold structure (Example 53). Blood readily wicks into the porous calcium phosphate bodies without obvious detrimental effects. It is believed that cells, e.g., fibroblasts, mesenchymal, stromal, marrow, and stem cells, as well as protein-rich plasma and combinations of the aforementioned cells can also be imbibed into the porous structures.

Highly porous calcium phosphate cylindrical plugs were prepared as described in Example 55 starting with 10 mm discs punched from Normandy compressed sponge. The cylindrical porous bodies were dry heat sterilized in DualPeel™ self seal pouches (distributed by Allegiance Healthcare Corp., McGaw Park, Ill. 60085) at 125° C. for 8 hours.

An animal experiment was initiated at Michigan State University, whereby a 10.3 mm×25 mm defect was drilled into the right shoulder (greater tubercle) of mongrel dogs. The site was cleaned of bone fragments and the site filled with blood (and marrow cells) as the site was centered in metaphyseal bone. The scaffold implants were removed from their sterile pouch and inserted into the defect site. Initial penetration to half of the 25 mm depth was easily achieved with little resistance. Slight pushing was required to insert the remainder of the implant into the site, such that the top of the scaffold was flush with the cortical bone surface. During insertion, blood could be seen readily wicking up the porous scaffold. After complete insertion of the implant, blood could be seen flowing throughout and around the scaffold. The implant intergrity was maintained with no fragmentation or breakage. The compatibility with blood and marrow was evident. The surgical site was then closed.

Figure 26:
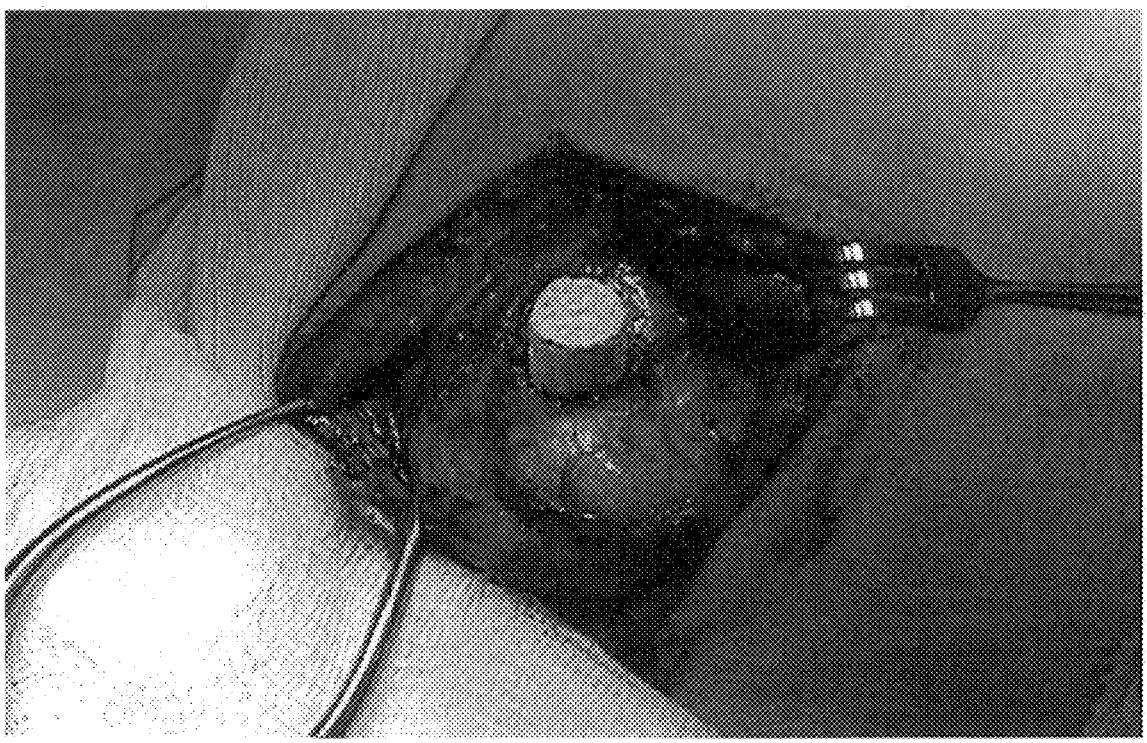
FIG. 26 depicts a calcium phosphate porous body, produced in accordance with one embodiment of this invention partially wicked with blood.
Figure 27:
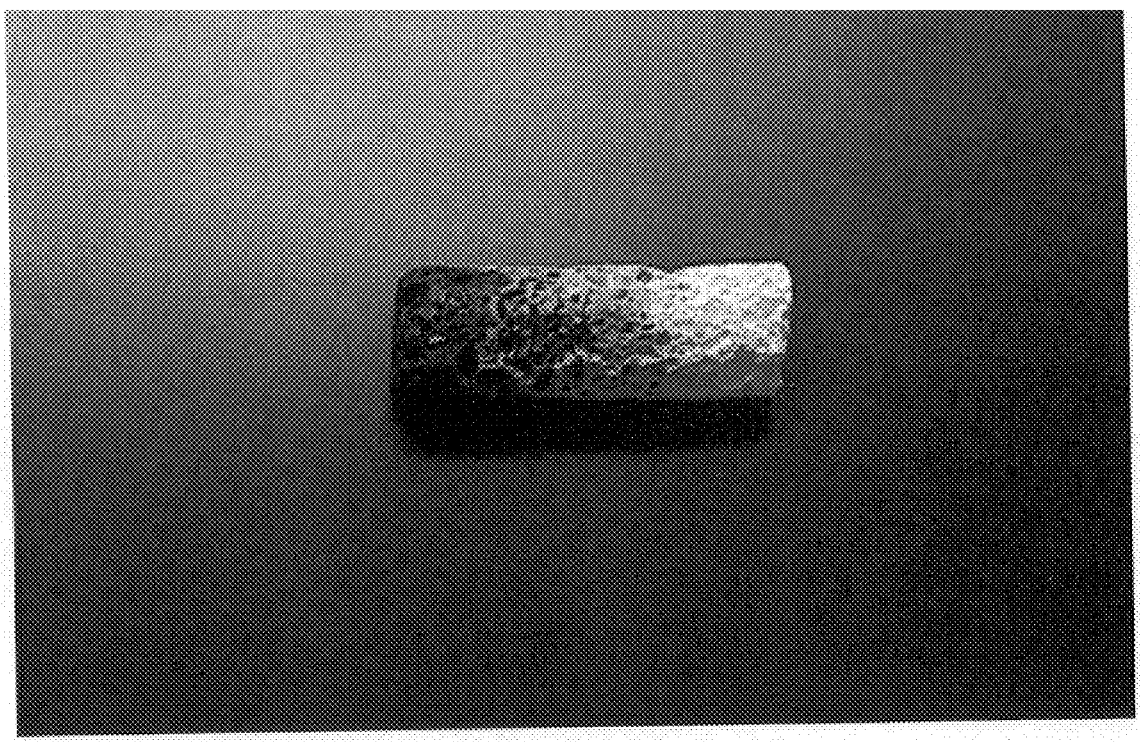
FIG. 27 shows a cylinder of calcium phosphate prepared in accordance with one embodiment of this invention, implanted into the metaphyseal bone of a canine.

FIG. 26 shows the cylindrical implant with initial wicking of blood. FIG. 27 depicts implantation of the cylinder into the canine bone.

Example 57

Porous Shaped Bodies of Hydroxyapatite

The mineral phase of human bone consists primarily of compositionally modified, poorly crystalline hydroxyapatite, $Ca_5(PO_4)_3(OH)$. The hydroxyapatite crystallographic structure is partially substituted by carbonate anions (7.4 wt. %) as well as by metal cations present at fractional wt. % levels. Analysis of human bone [R. Z. LeGeros, "Calcium Phosphates in Oral Biology and Medicine," Monographs in Oral Science, Vol. 15 (H. M. Myers, Ed.), p 110, Karger Press (1991)] indicates, for example, that the principal trace cationic constituents are as follows: $Na^+$ (0.9 wt. %), $Mg^{2+}$ (0.72 wt. %), and $Zn^{2+}$ (trace, assumed as 0.05 wt. %). Heretofore, it has been difficult, if not impossible, to synthesize hydroxyapatite mineral doped with cations to the appropriate levels so as to approximate bone mineral. A unique capability and distinct advantage of the RPR method is the facile manner in which precursor solutions containing mixed metal ions can be prepared and converted into solid phases via the redox precipitation reaction and subsequent thermal processing.

A reactant solution was prepared by combining 7.88 g 50 wt. % hypophosphorous acid, $H_3PO_2$, with 5.00 g deionized water in a 250 ml Pyrex beaker. To this solution was added 22.51 g calcium nitrate tetrahydrate salt, $Ca(NO_3)_2.4H_2O$; plus 0.33 g sodium nitrate salt, $NaNO_3$ (Fisher Certified ACS reagent #S343-500, CAS #7631-99-4), equivalent to 27.05 wt. % Na; plus 0.74 g magnesium nitrate hexahydrate salt, $Mg(NO_3)_2.6H_2O$ (Alfa/Aesar reagent #11564, CAS 13446-18-9), equivalent to 9.48 wt. % Mg; plus 0.046 g $Zn(NO_3)_2.6H_2O$ (ACS reagent, Aldrich Chemical Co., Inc. #22,873-7, CAS 10196-18-6), equivalent to 21.97 wt. % Zn. Endothermic dissolution of the salts proceeded with stirring and gradual warming on a laboratory hot plate to approximately 20° C., eventually forming a homogeneous solution with a water-like viscosity despite the high salt concentration. The equivalent solids level (as cation substituted hydroxyapatite) was 27.39 wt. % and the target solid composition was 38.19 wt. % Ca, 0.90 wt. % Na, 0.70 wt. % Mg, 0.10 wt. % Zn, 56.72 wt. % $PO_4$, and 3.39 wt. % OH.

Eighteen ⅜-inch diameter×1-inch length cylinders of Normandy sponge were imbibed with this reactant liquid to approximately seven times their initial weight and microwave processed as described in Example 55. The dried, solid-filled cylindrical sponge pieces were then fired according to the procedure described in Example 55. The resultant cylindrical white porous inorganic scaffold samples were robust and subjectively equivalent in strength to the articles produced in Example 55.

Figure 28:
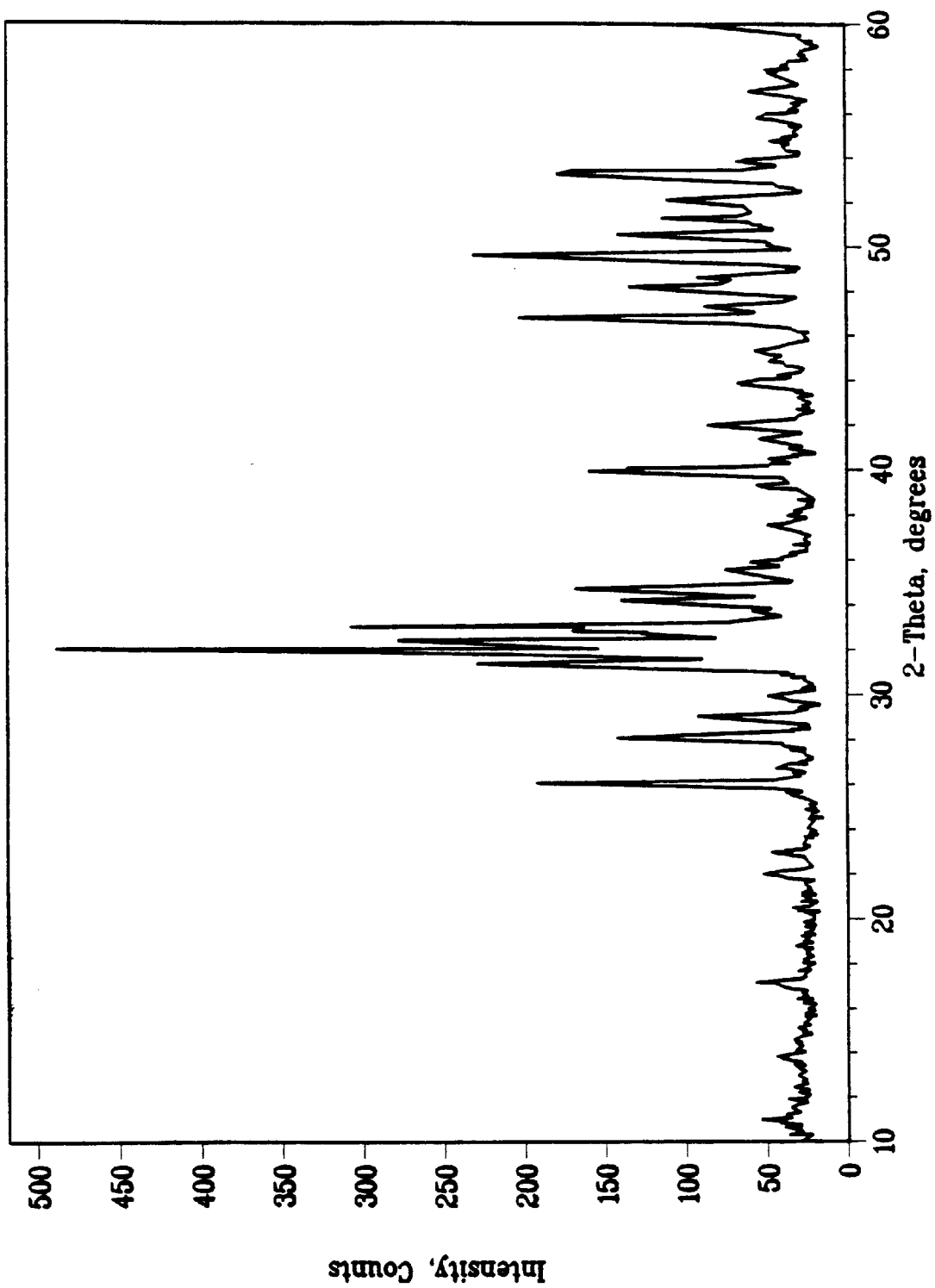
FIG. 28 is an X-ray diffraction plot of a pulverized sample of a cation substituted hydroxyapatite material processed in accordance with the methods described in this invention.

An XRD pattern, FIG. 28, was obtained, as described in Example 39, from a packed powder sample of the material fired at 800° C. Analysis of both peak position and relative intensities over the angular range from 10 to 60 degrees (2-theta) indicated the solid to consist of hydroxyapatite (PDF 09-0432). Additionally, four unassigned peaks at 29.9, 31.3, 34.7, and 47.4 degrees (2-theta) were observed in this sample. These are, presumably, due to the cationic substitutions leading to a distorted hydroxyapatite lattice structure.

The inorganic porous material prepared in Examples 39 through 57, derived from the precursor aqueous solutions involving the minerals or materials described in the preceding Examples 1 though 38, can be utilized in a variety of applications. These applications include, but are not limited to: bone or teeth replacement, filters, catalytic converters, catalytic substrates, bioseparations media, pharmaceutical excipients, gas scrubber media, piezoelectric ceramics, pharmaceutical drug delivery systems, or aerators. As the examples illustrate, the composition can be easily tailored to accommodate the particular end use without the concerns of extensive material preparation such as purification or particle size treatment. Further, the porous inorganic material can be formed into a variety of practical shapes without elaborate tools or machining.

Example 58

Composite Members for Reconstructive Use

A composite structure in accordance with this invention can be formed from an RPR material and from polymerizable material. A shaped structure is molded from an RPR material, especially one which gives rise to calcium phosphate. Any of the foregoing methods for preparing shaped bodies of RPR can be used in this context. Thus, for example, an RPR calcium phosphate is molded in the shape of an elongated rectangular prism. The shape is preferably purged of any cellulosic or other material used in its formation and is rinsed of acidic residues and rendered sterile.

The shaped calcium phosphate is then coated with hardenable material such as any of the polymerizable systems described heretofore. It is preferred that the polymerizable material be an acrylic system having inorganic fillers, especially where such fillers comprise at least a portion of Combeite to render the same bioactive. The hardenable material is then hardened either through thermal or photochemical mechanisms or otherwise.

The resulting composite structure has a core of RPR material surrounded by a layer of hard polymer, preferably a polymer exhibiting bioactivity. As will be apparent, this structure mimics e mammalian bone, having a trabecular internal structure surrounded by a cancellous, hard exterior. Such structures may be elaborated in a very wide array of shapes for use in orthopaedic and other surgical restorations and reconstructions. On particular use is in the preparation of vertebral appliances such a cages, rings spacers and spinal devices of many kinds. An additional use is in the preparation of materials for structural bone repair and te like. Thus, it can be seen that the RPR material which forms the overall shape of the structure can be molded or otherwise formed into a wide variety of shapes and, indeed, may be formed "to order" in an operating room. Thus, RPR materials can be milled or carved from a preformed block to precisely match a prepared location for surgical reconstruction. The shaped RPR material may then be coated with polymerizable material in any number of ways and the polymer cured, especially via actinic light. The coating with polymerizable material may be accomplished via dipping, spraying, painting, extrusion, sculpting, or, in short, in any convenient way amenable to the polymerizable material being used.

While the polymerizable material can be thermally cured, such as when two-paste systems are employed, actinic light curing systems are preferred. Such actinic light curing is widely practiced in dental restoration and its techniques are well-known and can be easily modified to the practice of this invention. The preparation of the restoration can be accomplished in a matter of minutes, minimizing operative time. The restoration comprising the composite structures of this invention is applied to a prepared site and preferably adhered therein. For this purpose, polymerizable adhesives in the form of pastes, putties or liquids are employed, especially those formed from acrylic systems. Most preferred are acrylic cements and putties including fillers having bioactive fillers, especially Combeite. In accordance with some preferred embodiments, cement access orifices are provided in the composite shaped bodies of the invention. Such holes permit good penetration of adhesive or cements and may offer superior performance.

It will be appreciated that the polymerizable material coated upon the RPR material may be all or partially polymerized in situ to either serve the adhesive function or to assist therein. It can be convenient to apply two or more layers of polymerizable material to the RPR structure for diverse purposes. Indeed, several different polymerizable systems may be employed. Thus, one layer or coating may be applied for strength, another for biocompatibility and a third for adhesive purposes. Other functions or combinations may be employed.

The composite structures of this invention can mimic natural bone structure. It is believed that the presence of an open trabecular structure provided by the RPR material together with the hard, strong structure mimicking cancellous bone as can be provided by acrylic polymers gives rise to superior results in use. Thus, the restorative composite structures are immediately weight bearing, while their trabecular structure provides less mass and confers some resilience to the restoration. This composite structure provides restorations which are easily accepted by natural bone and which does not overly stress natural structures.

It will be appreciated that the methods for accomplishing the particular steps described above are well known to persons of ordinary skill in the art in view of the present specification, of U.S. Pat. Nos. 5,681,872 and 5,914,356 and the specifications of U.S. Ser. Nos. 784,439 filed Jan. 16, 1997; 011,219 filed Dec. 12, 1997; and 253,556 filed Feb. 19, 1999; incorporated herein by reference.

Example 59

Reinforced Composite Members

A composite member for reconstructive use can be prepared in accordance with the previous example, but with the inclusion of reinforcements. Thus, an RPR shape is molded, extruded, or otherwise formed surrounding or substantially surrounding one or more rods or other reinforcements. The resulting structure is, itself, a composite structure in accordance with the invention. It is preferred, however, to further elaborate upon the structure by applying to it polymerizable material for subsequent curing and use. It will be understood that reinforcement may take the form of metallic, ceramic, glass, polymeric or other structures within or upon one of the portions of the composite structures of this invention and that such reinforcement may be included for purposes of strength, durability, biostimulation, biocompatibility, drug delivery, biopharmaceutical delivery or many other functions.

Example 60

Complex Composite Members

A shape is molded from acrylic polymer filled with silanated microfine silica in accordance with conventional techniques. The shape is selected to closely mimic a lachrymal bone in an adult human. The molded shape is coated with calcium phosphate RPR precursor material, including a cellulosic material to form a viscous putty-fluid. The RPR reaction is caused to occur and the resulting RPR material is heated, washed and otherwise treated as the practitioner may desire. The resulting structure comprises the acrylic shape coated with RPR materia, the whole taking the overall shape of the original acrylic body. A plurality of holes are drilled in the body (or were present in the original molded form). A further polymer-forming mixture is then applied to the shaped body to coat all or a portion of it. The same is polymerized yielding a "three layer sandwich" arrangement of polymer core, RPR layer and polymer top coating. The materials are selected such that the overall structure is strong, but somewhat flexible. Upon application of crushing force, the structure crushes rather than shatters. Accordingly, when used in facial reconstruction, the bone replacement thus formed will crush and deform, rather than shatter into potentially lethal shards.

Example 61

Composite Catalytic Structures

Helices, tori, Raschig rings, microtubes and other structures for use in packing chemical processing vessels, columns and the like can be formed in accordance with the invention. Thus, metallic shapes are formed in the desired configuration and coated with RPR material. Since RPR materials can be formed in a very wide variety of chemical forms and structures, extraordinary flexibility in the provision of such structures can be accomplished. Thus, structures having platinum, nickel, nickel alloys, palladium, copper, iron and many other chemical moieties may be exposed to chemical processes in a solid, easily filterable or, indeed, stationary form. Diverse catalytic and separatory functions may be accomplished with such structures.

The present invention may be embodied in other specific forms without departing from the spirit or essential attributes thereof and, accordingly, reference should be made to the appended claims rather than to the foregoing specifications, as indicating the scope of the invention.

What is claimed is:

1. A shaped body comprising
   a first solid portion and
   a second portion on the first solid portion comprising the oxidation-reduction reaction product of a blend comprising at least one metal cation;

at least one oxidizing agent; and at least one precursor anion oxidizable by said oxidizing agent to form an oxoanion;

said reaction having given rise to at least one gaseous product.

2. The shaped body of claim 1 wherein said oxidizing agent is nitrate.

3. The shaped body of claim 1 wherein said gaseous product is a nitrogen oxide.

4. The shaped body of claim 1 wherein said reaction has been conducted at temperatures up to about 250° C.

5. The shaped body of claim 1 wherein said reaction has been conducted at temperatures up to about 800° C.

6. The shaped body of claim 1 wherein said reaction has been conducted at temperatures up to about 1400° C.

7. The shaped body of claim 1 wherein said reaction has been conducted at temperatures below the melting temperature of said reaction product.

8. The shaped body of claim 1 wherein said reaction product is a calcium phosphate.

9. The shaped body of claim 1 wherein said blend comprises an alcohol.

10. The shaped body of claim 1 wherein said metal cation forms part of the oxidizing agent.

11. The shaped body of claim 1 wherein said oxidizing agent and metal cation comprise a metal nitrate.

12. The shaped body of claim 1 wherein said metal cation is at least one of Li, Na, K, Rb, Cs, Cu, Ag or Hg.

13. The shaped body of claim 1 wherein said metal cation is at least one of divalent Be, Cr, Mn, Fe, Co, Ni, Cu, Zn, Rh, Pd, Cd, Sn, Hr or Pb.

14. The shaped body of claim 1 wherein said metal cation is at least one of tri- or tetravalent Al, Cr, Mn, Fe, Co, Ni, Ga, As, Y, Nb, Rh, In, La, Tl, Bi, Ac, Ce, Pr, Nd, Sm, Eu, Gd, Tb, Dy, Ho, Er, Tm, Yb, Lu, U, or Pu.

15. The shaped body of claim 1, wherein said metal cation comprises Ca.

16. The shaped body of claim 1 having a preselected shape.

17. The shaped body of claim 2 wherein said preselected shape mimics a bony structure on the human body.

18. The shaped body of claim 2 wherein said preselected shape is adapted to fit a bone excavation.

19. The shaped body of claim 1 wherein said preselected shape is in the form of a rod, screw, pin, dowel, vertebra, vertebral segment, intervertebral disk, intervertebral disk segment or spacer, orthopaedic cage, orthopaedic block, vertebral ring, interbody fusion device, tri-cortical device, crouton, or splint.

20. The shaped body of claim 1 having a plurality of orifices in at least one exterior surface thereof.

21. The shaped body of claim 1 wherein said first solid portion comprises a polymer.

22. The shaped body of claim 21 wherein said polymer is formed from a polymerized matrix and at least one inorganic filler.

23. The shaped body of claim 22 wherein said polymer comprises at least one acrylic species.

24. The shaped body of claim 22 wherein said polymer further comprises at least one organic filler.

25. The shaped body of claim 24 wherein said organic filler comprises fibers, a web or particulate material.

26. The shaped body of claim 22 wherein said inorganic filler comprises combeite.

27. The shaped body of claim 26 wherein said combeite is present in an amount of at least about 2 percent by weight of the inorganic filler.

28. The shaped body of claim 26 wherein said combeite is in the form of heterogeneous particles.

29. The shaped body of claim 26 wherein said particles have particle sizes greater than about 0.1 micron.

30. The shaped body of claim 29 wherein at least 95 percent by weight of said particles have particle sizes between 0.2 and 100 microns.

31. The shaped body of claim 26 wherein said inorganic filler further comprises at least one of hydroxyapatite, fluorapatite, oxyapatite, Wollastonite, anorthite, calcium fluoride, agrellite, devitrite, canasite, phlogopite, monotite, brushite, octocalcium phosphate, Whitlockite, tetracalcium phosphate, cordierite, Berlinite or mixtures thereof.

32. The shaped body of claim 21 wherein said polymer comprises a bisphenol-A dimethacrylate.

33. The shaped body of claim 32 wherein said dimethacrylate is a diglycidyl methacrylate.

34. The shaped body of claim 21 wherein said polymer has been hardened through the activity of a heat or actinic light.

35. The shaped body of claim 1 wherein said second portion is spongiform.

36. The shaped body of claim 1 in combination with a hardenable fluid material.

37. The shaped body of claim 36 wherein said fluid material is a liquid, paste, putty or gel.

38. The shaped body of claim 36 wherein said fluid material is polymerizable.

39. The shaped body of claim 36 wherein said fluid material is acrylic.

40. The shaped body of claim 36 further comprising a plurality of orifices therein.

41. A restorative system comprising a shaped body comprising a first solid portion and a second portion on the first solid portion comprising the oxidation-reduction reaction product of a blend comprising at least one metal cation;

at least one oxidizing agent; and at least one precursor anion oxidizable by said oxidizing agent to form an oxoanion;

said reaction having given rise to at least one gaseous product; and a hardenable fluid material.

42. The restorative system of claim 41 wherein said fluid material is a liquid, paste, putty or gel.

43. The restorative system of claim 41 wherein said fluid material is polymerizable.

44. The restorative system of claim 41 wherein said fluid material is acrylic.

45. The restorative system of claim 41 further comprising a plurality of orifices therein for placement of the fluid material adjacent to the shaped body within a prepared osseous cavity.

* * * * *

UNITED STATES PATENT AND TRADEMARK OFFICE
CERTIFICATE OF CORRECTION

PATENT NO. : 6,458,162 B1
DATED : October 1, 2002
INVENTOR(S) : Antony Koblish et al.

It is certified that error appears in the above-identified patent and that said Letters Patent is hereby corrected as shown below:

<u>Title page,</u>
Item [75], Inventors, delete "Eric" and insert -- Erik --.
Item [56], References Cited, U.S. PATENT DOCUMENTS, insert
-- U.S. Patent No. 5,645,934  7/1997   Marcolongo et al.  428/357 --.

<u>Column 1,</u>
Line 45, "(PO04)" and insert -- (PO4) --;
Line 45, "(CO03)" and insert -- (CO3) --;

<u>Column 10,</u>
Line 24, delete "$(CO_3)x$" and insert -- $(CO_3)_x$ --;

<u>Column 19,</u>
Line 31, delete "$\geq$" and insert -- $>$ --;

<u>Column 20,</u>
Line 40, delete "$(NO2^-)$" and insert -- $(NO_2^-)$ --;

<u>Column 23,</u>
Line 25, delete "$(p^{+1})$" and insert -- $(P^{+1})$ --;

<u>Column 28,</u>
Line 47, delete "had" and insert -- has --;

<u>Column 30,</u>
Line 50, delete "5½" and insert -- 5-1/2 --;

<u>Column 31,</u>
Line 46, delete "$(CO_3)x$" and insert -- $(CO_3)_x$ --;
Line 54, delete "diff-use" and insert -- diffuse --;

<u>Column 37,</u>
Line 39, delete "wt" and insert -- wt% --;

<u>Column 39,</u>
Example 20, delete "15-min" and insert -- 15-18 min --;

<u>Column 49,</u>
Line 15, after "The" insert -- following table summarizes --;

UNITED STATES PATENT AND TRADEMARK OFFICE
CERTIFICATE OF CORRECTION

PATENT NO.   : 6,458,162 B1
DATED        : October 1, 2002
INVENTOR(S)  : Antony Koblish et al.

It is certified that error appears in the above-identified patent and that said Letters Patent is hereby corrected as shown below:

<u>Column 53,</u>
Line 56, delete "·6H2O" and insert -- ·6H$_2$O --;

<u>Column 54,</u>
Line 64, delete "On" and insert -- One --;
Line 67, delete "te" and insert -- the --;

<u>Column 56,</u>
Line 26, delete "materias," and insert -- material, --.

Signed and Sealed this

Twenty-seventh Day of January, 2004

JON W. DUDAS
*Acting Director of the United States Patent and Trademark Office*